(12) United States Patent
Newberry et al.

(10) Patent No.: US 10,744,261 B2
(45) Date of Patent: Aug. 18, 2020

(54) SYSTEM AND METHOD OF A BIOSENSOR FOR DETECTION OF VASODILATION

(71) Applicant: SANMINA CORPORATION, San Jose, CA (US)

(72) Inventors: Robert Steven Newberry, New Hope, AL (US); Matthew Rodencal, Huntsville, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days.

(21) Appl. No.: 16/172,661

(22) Filed: Oct. 26, 2018

(65) Prior Publication Data

US 2019/0060568 A1    Feb. 28, 2019

Related U.S. Application Data

(60) Continuation-in-part of application No. 14/866,500, filed on Sep. 25, 2015, now Pat. No. 10,321,860, and
(Continued)

(51) Int. Cl.
*A61B 5/00* (2006.01)
*A61B 5/1455* (2006.01)
(Continued)

(52) U.S. Cl.
CPC ....... *A61M 5/1723* (2013.01); *A61B 5/02007* (2013.01); *A61B 5/0295* (2013.01); *A61B 5/02416* (2013.01); *A61B 5/14551* (2013.01); *A61M 5/14248* (2013.01); *A61M 5/3298* (2013.01); *A61B 5/0077* (2013.01);
(Continued)

(58) Field of Classification Search
None
See application file for complete search history.

(56) References Cited

U.S. PATENT DOCUMENTS 4,913,150 A    4/1990  Cheung et al.
5,115,133 A    5/1992  Knudson
(Continued)

FOREIGN PATENT DOCUMENTS

CN    102609627 A    7/2012
EP    2017001250 A1    1/2017
(Continued)

OTHER PUBLICATIONS

"Jeong et al.," "Non-invasive Estimation of Systolic Blood pressure and Diastolic pressure using Photoplethysmograph Components," Younse Med J. May 1, 2010 51(3): 345-353.*
(Continued)

*Primary Examiner* — Patricia J Park
(74) *Attorney, Agent, or Firm* — Loza & Loza, LLP; Julio M. Loza; Jessica W. Smith

(57) ABSTRACT

An optical circuit detects PPG signals reflected from skin tissue at one or more different wavelengths. A processing circuit integrated in the biosensor or in communication with the biosensor processes the PPG signals to obtain a level of vasodilation or a period of vasodilation. The processing circuit may determine a circulation level using a phase offset between the PPG signals and/or a correlation value between the PPG signals.

22 Claims, 32 Drawing Sheets

Related U.S. Application Data a continuation-in-part of application No. 15/811,479, filed on Nov. 13, 2017, now Pat. No. 10,238,346, and a continuation-in-part of application No. 15/485,816, filed on Apr. 12, 2017, now Pat. No. 10,155,087, which is a continuation of application No. 15/276,760, filed on Sep. 26, 2016, now Pat. No. 9,636,457, application No. 16/172,661, which is a continuation-in-part of application No. 15/718,721, filed on Sep. 28, 2017, now Pat. No. 10,517,515, which is a continuation of application No. 15/622,941, filed on Jun. 14, 2017, now Pat. No. 9,788,767, application No. 16/172,661, which is a continuation-in-part of application No. 15/804,581, filed on Nov. 6, 2017, now Pat. No. 10,231,674, which is a continuation of application No. 15/404,117, filed on Jan. 11, 2017, application No. 16/172,661, which is a continuation-in-part of application No. 15/958,620, filed on Apr. 20, 2018, now Pat. No. 10,524,720, which is a continuation of application No. 15/680,991, filed on Aug. 18, 2017, now Pat. No. 9,968,289, application No. 16/172,661, which is a continuation-in-part of application No. 15/400,916, filed on Jan. 6, 2017, and a continuation-in-part of application No. 16/019,518, filed on Jun. 26, 2018, which is a division of application No. 15/867,632, filed on Jan. 10, 2018, now Pat. No. 10,039,500, application No. 16/172,661, which is a continuation-in-part of application No. 15/859,147, filed on Dec. 29, 2017, now Pat. No. 10,194,871, and a continuation-in-part of application No. 15/898,580, filed on Feb. 17, 2018.

(60) Provisional application No. 62/577,707, filed on Oct. 26, 2017, provisional application No. 62/613,388, filed on Jan. 3, 2018, provisional application No. 62/675,151, filed on May 22, 2018, provisional application No. 62/463,104, filed on Feb. 24, 2017.

(51) Int. Cl.
| | |
|---|---|
| *A61B 5/024* | (2006.01) |
| *A61B 5/0295* | (2006.01) |
| *A61M 5/172* | (2006.01) |
| *A61M 5/142* | (2006.01) |
| *A61M 5/32* | (2006.01) |
| *A61B 5/02* | (2006.01) |
| *A61M 5/145* | (2006.01) |
| *A61B 5/01* | (2006.01) |
| *A61B 5/08* | (2006.01) |
| *A61B 5/021* | (2006.01) |

(52) U.S. Cl.
CPC ............ *A61B 5/01* (2013.01); *A61B 5/021* (2013.01); *A61B 5/0816* (2013.01); *A61B 5/7264* (2013.01); *A61B 2503/40* (2013.01); *A61M 5/145* (2013.01); *A61M 2205/3306* (2013.01); *A61M 2205/3584* (2013.01); *A61M 2205/502* (2013.01); *A61M 2205/52* (2013.01); *A61M 2205/8206* (2013.01); *A61M 2205/8268* (2013.01); *A61M 2230/06* (2013.01); *A61M 2230/20* (2013.01); *A61M 2230/30* (2013.01); *A61M 2230/42* (2013.01); *A61M 2230/50* (2013.01); *A61M 2230/63* (2013.01)

(56) References Cited

U.S. PATENT DOCUMENTS

| | | |
|---|---|---|
| 5,269,310 A | 12/1993 | Jones et al. |
| 5,358,703 A | 10/1994 | Lai |
| 5,515,847 A | 5/1996 | Braig et al. |
| 5,673,692 A | 10/1997 | Schulze et al. |
| 5,823,966 A | 10/1998 | Buchert |
| 5,947,911 A | 9/1999 | Wong et al. |
| 5,983,121 A | 11/1999 | Tsuchiya |
| 6,087,087 A | 7/2000 | Yonetani et al. |
| 6,280,390 B1 * | 8/2001 | Akselrod ............ A61B 5/02416 600/475 |
| 6,285,896 B1 | 9/2001 | Tobler et al. |
| 6,305,804 B1 | 10/2001 | Rice et al. |
| 6,537,225 B1 | 3/2003 | Mills |
| 6,694,180 B1 | 2/2004 | Boesen |
| 6,719,705 B2 | 4/2004 | Mills |
| 6,819,950 B2 | 11/2004 | Mills |
| 6,921,367 B2 | 7/2005 | Mills |
| 6,985,763 B2 | 1/2006 | Boas et al. |
| 7,154,592 B2 | 12/2006 | Reynolds et al. |
| 7,167,736 B2 | 1/2007 | Winther |
| 7,171,251 B2 | 1/2007 | Sarussi et al. |
| 7,179,228 B2 | 2/2007 | Banet |
| 7,209,775 B2 | 4/2007 | Bae et al. |
| 7,291,497 B2 | 11/2007 | Holmes et al. |
| 7,371,562 B2 | 5/2008 | Cunningham et al. |
| 7,608,045 B2 | 10/2009 | Mills |
| 7,647,083 B2 | 1/2010 | Al-Ali et al. |
| 7,761,127 B2 | 7/2010 | Al-Ali et al. |
| 7,763,472 B2 | 7/2010 | Doctor et al. |
| 7,764,982 B2 | 7/2010 | Dalke et al. |
| 7,941,199 B2 | 5/2011 | Kiani |
| 8,224,411 B2 | 7/2012 | Al-Ali et al. |
| 8,255,027 B2 | 8/2012 | Al-Ali et al. |
| 8,328,420 B2 | 12/2012 | Abreu |
| 8,385,996 B2 | 2/2013 | Smith et al. |
| 8,401,605 B2 | 3/2013 | Huiku |
| 8,483,787 B2 | 7/2013 | Al-Ali et al. |
| 8,494,507 B1 | 7/2013 | Tedesco et al. |
| 8,597,274 B2 | 12/2013 | Sloan et al. |
| 8,652,040 B2 | 2/2014 | Leboeuf et al. |
| 8,676,284 B2 | 3/2014 | He |
| 8,730,047 B2 | 5/2014 | Ridder et al. |
| 8,868,149 B2 | 10/2014 | Eisen et al. |
| 8,888,701 B2 | 11/2014 | Leboeuf et al. |
| 8,906,693 B2 | 12/2014 | Schultz et al. |
| 8,923,918 B2 | 12/2014 | Kreger et al. |
| 8,961,932 B2 | 2/2015 | Silverman |
| 9,022,973 B2 | 5/2015 | Sexton et al. |
| 9,131,882 B2 | 9/2015 | Al-Ali et al. |
| 9,149,216 B2 | 10/2015 | Eisen et al. |
| 9,149,646 B2 | 10/2015 | Keswarpu et al. |
| 9,387,033 B2 | 7/2016 | Yodfat et al. |
| 9,442,092 B2 | 9/2016 | Lane |
| 9,521,970 B2 | 12/2016 | Hoppe et al. |
| 9,554,738 B1 | 1/2017 | Gulati et al. |
| 9,642,578 B2 | 5/2017 | Newberry |
| 9,668,701 B2 | 6/2017 | Maarek |
| 9,713,428 B2 | 7/2017 | Chon et al. |
| 9,739,663 B2 | 8/2017 | Halder et al. |
| 9,820,656 B2 | 11/2017 | Olivier |
| 9,839,381 B1 | 12/2017 | Weber et al. |
| 9,924,895 B2 | 3/2018 | Rawicz et al. |
| 9,949,675 B2 | 4/2018 | Miller |
| 9,999,355 B2 | 6/2018 | Kirenko |
| 10,028,682 B2 | 7/2018 | Thiele |
| D824,937 S | 8/2018 | Sparandara et al. |
| 10,099,554 B2 | 10/2018 | Steeg et al. |
| 10,130,285 B1 | 11/2018 | Singamsetty et al. |
| 10,153,796 B2 | 12/2018 | Fung et al. |
| 10,181,021 B2 | 1/2019 | Venkatraman et al. |
| 10,206,619 B1 | 2/2019 | Lee et al. |
| 10,215,698 B2 | 2/2019 | Han et al. |
| 10,227,063 B2 | 3/2019 | Abreu |
| 10,232,156 B2 | 3/2019 | Netzel et al. |
| 10,278,591 B2 | 5/2019 | Gil |

(56) References Cited

U.S. PATENT DOCUMENTS

| | | | |
|---|---|---|---|
| D850,316 S | 6/2019 | Ennis et al. |
| 10,314,500 B2 | 6/2019 | Olivier |
| 10,322,728 B1 | 6/2019 | Porikli et al. |
| 10,342,495 B2 | 7/2019 | Melkoniemi et al. |
| 10,349,847 B2 | 7/2019 | Kwon et al. |
| 10,420,470 B2 | 9/2019 | Kwon et al. |
| 10,420,491 B2 | 9/2019 | Rajan et al. |
| 10,433,726 B2 | 10/2019 | Ramesh et al. |
| 10,433,738 B2 | 10/2019 | Thomas et al. |
| 10,433,739 B2 | 10/2019 | Weekly et al. |
| 10,463,283 B2 | 11/2019 | Ferber et al. |
| 2002/0049389 A1 | 4/2002 | Abreu |
| 2003/0229276 A1 | 12/2003 | Sarussi et al. |
| 2004/0078219 A1 | 4/2004 | Kaylor et al. |
| 2004/0100376 A1 | 5/2004 | Lye et al. |
| 2004/0157341 A1 | 8/2004 | Reynolds et al. |
| 2005/0101841 A9 | 5/2005 | Kaylor et al. |
| 2005/0143665 A1* | 6/2005 | Huiku ............ A61B 5/14551 600/500 |
| 2005/0209516 A1 | 9/2005 | Fraden |
| 2005/0228244 A1 | 10/2005 | Banet |
| 2005/0228299 A1 | 10/2005 | Banet |
| 2005/0245831 A1 | 11/2005 | Banet |
| 2006/0009698 A1 | 1/2006 | Banet |
| 2006/0094942 A1 | 5/2006 | Winther |
| 2006/0287589 A1 | 12/2006 | Wobermin et al. |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | Leboeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0331631 A1 | 12/2010 | MacLaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1 | 1/2012 | Keswarpu et al. |
| 2012/0029363 A1* | 2/2012 | Lund ................ A61B 5/02108 600/485 |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0066176 A1* | 3/2013 | Addison ............ A61B 5/7207 600/324 |
| 2013/0110311 A1 | 5/2013 | Ver Steeg et al. |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsrporn et al. |
| 2016/0081628 A1* | 3/2016 | Melkoniemi ............ A61B 5/01 |
| 2016/0100781 A1 | 4/2016 | Bechtel et al. |
| 2016/0262707 A1 | 9/2016 | Devries |
| 2016/0367154 A1* | 12/2016 | Gladshtein ........... A61B 5/0261 |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018206875 A1 | 11/2018 |
| WO | 2019030700 A1 | 2/2019 |
| WO | 2019118053 A1 | 6/2019 |

OTHER PUBLICATIONS

"Elgendi," "On the analysis of Fingertip Photoplethysmogram Signals," Current Cardiology Reviews, 2008, 8, 14-25.*

(56) References Cited

OTHER PUBLICATIONS

PCT/US2019/032942. International Search Report & Written Opinion (dated Oct. 1, 2019).

\* cited by examiner

SYSTEM AND METHOD OF A BIOSENSOR FOR DETECTION OF VASODILATION

CROSS REFERENCE TO RELATED APPLICATIONS

The present application claims priority under 35 U.S.C. § 119(e) to U.S. Provisional Application No. 62/577,707 entitled, "SYSTEM AND METHOD FOR HEALTH MONITORING OF AN ANIMAL USING A MULTI-BAND BIOSENSOR," filed Oct. 26, 2017, and hereby expressly incorporated by reference herein.

The present application claims priority under 35 U.S.C. § 119(e) to U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 119(e) to U.S. Provisional Application No. 62/675,151 entitled, "SYSTEM AND METHOD OF A BIOSENSOR FOR DETECTION OF VASODILATION," filed May 22, 2018, and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

The present application claims priority under 35 U.S.C. § 120 as a continuation in part application to U.S. patent application Ser. No. 15/811,479 entitled, "SYSTEM AND METHOD FOR A BIOSENSOR INTEGRATED IN A VEHICLE," filed Nov. 13, 2017 and hereby expressly incorporated by reference herein.

The present application claims priority under 35 U.S.C. § 120 as a continuation in part application to U.S. patent application Ser. No. 15/485,816 entitled, "SYSTEM AND METHOD FOR A DRUG DELIVERY AND BIOSENSOR PATCH," filed Apr. 12, 2017 and hereby expressly incorporated by reference herein, which claims priority under 35 U.S.C. § 120 as a continuation application to U.S. Utility application Ser. No. 15/276,760, entitled, "SYSTEM AND METHOD FOR A DRUG DELIVERY AND BIOSENSOR PATCH," filed Sep. 26, 2016, now U.S. Pat. No. 9,636,457 issued May 2, 2017, which is hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, now U.S. Pat. No. 9,788,767 issued Oct. 17, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part application to U.S. patent application Ser. No. 15/804,581 entitled, "SYSTEM AND METHOD FOR HEALTH MONITORING INCLUDING A USER DEVICE AND BIOSENSOR," filed Nov. 6, 2017 and hereby expressly incorporated by reference herein, which claims priority as a continuation application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation in part application to U.S. Utility application Ser. No. 15/958,620 entitled, "SYSTEM AND METHOD FOR DETECTING A HEALTH CONDITION USING AN OPTICAL SENSOR," filed Apr. 20, 2018, and hereby expressly incorporated by reference herein which claims priority under 35 U.S.C. § 120 as a continuation application to U.S. Utility application Ser. No. 15/680,991 entitled, "SYSTEM AND METHOD FOR DETECTING A SEPSIS CONDITION," filed Aug. 18, 2017, and hereby expressly incorporated by reference herein and now issued as U.S. Pat. No. 9,968,289 issued May 15, 2018.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part to U.S. patent application Ser. No. 16/019,518 entitled, "SYSTEM AND METHOD FOR BLOOD TYPING USING PPG TECHNOLOGY," filed Jun. 26, 2018, and hereby expressly incorporated by reference herein, which claims priority under 35 U.S.C. § 120 as a divisional to U.S. patent application Ser. No. 15/867,632 entitled, "SYSTEM AND METHOD FOR BLOOD TYPING USING PPG TECHNOLOGY," filed Jan. 10, 2018, and hereby expressly incorporated by reference herein, and now issued as U.S. Pat. No. 10,039,500 issued Aug. 7, 2018.

The present application claims priority under 35 U.S.C. § 120 as a continuation in part to U.S. patent application Ser. No. 15/859,147 entitled, "VEHICLULAR HEALTH MONITORING SYSTEM AND METHOD," filed Dec. 29, 2017 and hereby expressly incorporated by reference herein.

The present application claims priority under 35 U.S.C. § 120 as a continuation in part to U.S. patent application Ser. No. 15/898,580 entitled, "SYSTEM AND METHOD FOR OBTAINING HEALTH DATA USING A NEURAL NETWORK," filed Feb. 17, 2018, and hereby expressly incorporated by reference herein.

FIELD

This application relates to a system and methods of non-invasive health monitoring, and in particular, a system and method for detection of vasodilation using an optical sensor.

BACKGROUND

A person's vitals, such as temperature, blood oxygen levels, respiration rate, relative blood pressure, etc., may need to be monitored periodically typically using one or more instruments. For example, instruments for obtaining vitals of a user include blood pressure cuffs, thermometers, $SpO_2$ measurement devices, glucose level meters, etc. Often, multiple instruments must be used to obtain vitals of a person. This monitoring process is time consuming, inconvenient and is not always continuous. This multitude of instruments is also not portable or readily available to operators of a vehicle.

The detection of substances and measurement of concentration level or indicators of various substances in a user's blood stream is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood or tissue pigments (DC components), to eliminate the effect of tissue absorbance to measure the oxygen saturation of arterial blood. For example, when the heart pumps blood to the body and the lungs during systole, the amount of blood that reaches the capillaries in the skin surface increases, resulting in more light absorption. The blood then travels back to the heart through the venous network, leading to a decrease of blood volume in the capillaries and less light absorption. The measured PPG waveform therefore comprises a pulsatile (often called "AC") physiological waveform that reflects cardiac synchronous changes in the blood volume with each heartbeat, which is superimposed on a much larger slowly varying quasi-static ("DC") baseline. The use of PPG techniques as heretofore been used for measurement of the oxygen saturation of blood in vessels.

As such, there is a need for a non-invasive health monitoring system and method that monitors health conditions of a user non-invasively, continuously and in real time.

In particular, there is a need for an improved system and method for detection of vasodilation and conditions affected by vasodilation.

SUMMARY

According to a first aspect, a device includes an optical circuit configured to detect photoplethysmography (PPG) signals, wherein the PPG signals include a first spectral response obtained from light reflected around a first wavelength from skin tissue of a patient and a second spectral response obtained from light reflected around a second wavelength from the skin tissue of the patient. The device further includes a processing circuit configured to determine one or more parameters from one or more of: the first spectral response or the second spectral response and determine one or more of: a vasodilation period or a level of vasodilation using the one or more parameters.

According to a second aspect, a biosensor includes an optical circuit configured to detect a first PPG signal reflected around a first wavelength from skin tissue of a patient and a second PPG signal reflected around a second wavelength from the skin tissue of the patient. The biosensor further includes a processing circuit configured to determine one or more of: a phase offset between the first and second PPG signals or a correlation value between the first and second PPG signals and determine a circulation level using one or more of: the phase offset or the correlation value.

According to a third aspect, a device includes a PPG circuit configured to obtain a first photoplethysmography (PPG) signal around a first wavelength reflected from skin tissue of a patient and a second PPG signal around a second wavelength reflected from the skin tissue of the patient. The device further includes a processing device configured to obtain a phase offset between the first and second PPG signals and determine a circulation level using the phase offset.

In one or more of the above aspects, the first wavelength penetrates the skin tissue of the patient at a greater depth than the second wavelength. The first wavelength is in a range from 650 nm to 1350 nm and the second wavelength is outside the range from 650 nm to 1350 nm.

In one or more of the above aspects, the processing device is further configured to determine a phase difference between the first spectral response and the second spectral response and determine a level of vasodilation or a period of vasodilation using the phase difference.

In one or more of the above aspects, the processing device is further configured to determine a measurement of arterial stiffness using the PPG signals detected during the period of vasodilation.

In one or more of the above aspects, the processing device is further configured to determine a change in amplitude of a low frequency component in the first spectral response or the second spectral response, wherein the low frequency component is not affected by pulsatile blood flow due to a cardiac cycle and determine a level of vasodilation or period of vasodilation using the change in amplitude of the low frequency component.

In one or more of the above aspects, the processing device is further configured to determine a change in an R value obtained using the first spectral response and the second spectral response and determine the level of vasodilation or the period of vasodilation using the change in the R value.

In one or more of the above aspects, the processing device is further configured to determine a change in optical absorption properties of the tissue using the first spectral response and the second spectral response and determine a level of vasodilation or period of vasodilation using the change in the absorption properties. The change in absorption properties is due to one or more of: an increase in blood flow in the tissue, movement of tissue due to widening of vessels or a change in tissue hue.

In one or more of the above aspects, the processing device is further configured to determine one or more indicators of an infection in the tissue of the patient using the PPG signals, wherein the one or more indicators include: the level of vasodilation in the skin tissue, the period of vasodilation or a skin temperature.

In one or more of the above aspects, the level of vasodilation includes a measurement of one or more of: a percentage of change in arterial width, diameter or planar area.

In one or more of the above aspects, the processing circuit is configured to determine that the circulation level is one of: a normal circulation level or an abnormal circulation level.

In one or more of the above aspects, the processing circuit is configured to determine a systemic circulation level or a circulation level at a tissue site.

In one or more of the above aspects, the processing circuit is configured to determine the correlation value by determining one or more of: a difference in pulse shape between the PPG signals or a temporal difference between the PPG signals.

In one or more of the above aspects, the processing device is further configured to determine one or more indicators of an infection in the tissue of the patient using the PPG signals, wherein the one or more indicators of the infection include one or more of: a circulation level or a skin temperature.

DETAILED DESCRIPTION

Figure 1:
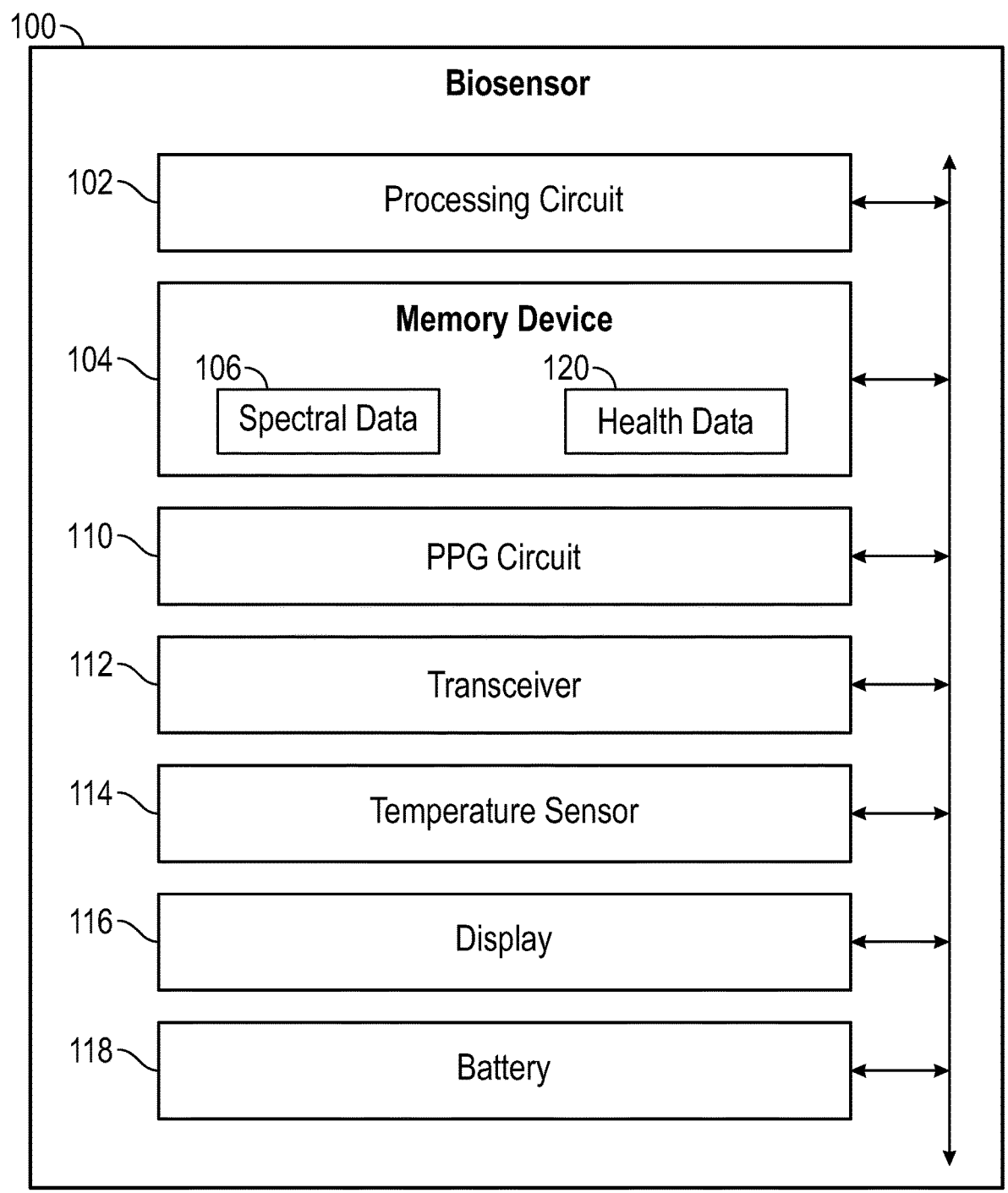
FIG. 1 illustrates a schematic block diagram of exemplary components in an embodiment of the biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

The release of the Endothelium-derived relaxing factor (EDRF) causes the arteries to expand in diameter and change elasticity, commonly referred to as vasodilation. Flow-mediated vasodilation measurements have been performed in human studies and are of diagnostic and prognostic importance. Prior techniques for measuring vasodilation require using high-frequency ultrasound to visually inspect vessels, most commonly the brachial artery. For example, one ultrasound technique evaluates flow-mediated vasodilation (FMD), an endothelium-dependent function, in the brachial artery. This process includes applying a stimulus to provoke the endothelium to release nitric oxide (NO) with subsequent vasodilation that is then imaged using high resolution ultrasonography and quantitated as an index of vasomotor function. This process of high-resolution ultrasonography of the brachial artery to evaluate vasomotor function has limitations. It must be performed in a clinical setting by a medical clinician using expensive ultrasonography equipment.

Thus, there is a need for an improved system and method for detection of vasodilation and conditions affected by vasodilation or conditions that affect vasodilation.

Vasodilation changes the way that a pressure wave in blood flow due to the heart beat propagates from deeper, larger vessels to shallower, smaller ones. In an embodiment described herein, this change in propagation of the pressure wave in vessels can be measured in the change in transfer function from a wavelength, e.g. in the near-IR window, which penetrates the tissue deeply, to a wavelength not in the near-IR window, which penetrates tissue much less deeply. This means that by measuring the change in shape and time delay of PPG signals of two or more wavelengths, where at least one is in the near-IR window and one is not, information about vasodilation and, more generally, arterial health and structure may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined include, but are not limited to, the phase delay between the systolic points and diastolic points in different wavelengths and the difference in dichroitic notch suppression between wavelengths.

In addition, because the temporal aspects of the transfer functions are not affected by respiration, blood composition, and other blood parameters, there is a high degree of signal isolation between the parameters of interest and other biological signals that are present in the amplitudes of the PPG signals. Once the temporally derived signals are determined, the new information can be used to compensate amplitude based measurements (such as R values), including but not limited to oxygen saturation SpO2. The accuracy of these amplitude based measurements may be improved by calibrating the measurements based on a level of vasodilation.

In addition, the temporally derived signals can be used to increase the signal level of previously undetectable biological signals. This detection enables the non-invasive measurement of previously difficult to measure biological parameters, including but not limited to, enhanced blood gas analysis, differential tissue composition, blood viscosity, blood pressure, general arterial health, chemical absorption rates in tissue of various foreign body compounds (like drugs, and other pharmaceuticals) and naturally occurring ones, and vasodilation, to name a few.

Embodiment of the Biosensor

In an embodiment, a biosensor includes an optical sensor or photoplethysmography (PPG) circuit configured to transmit light at a plurality of wavelengths directed at skin tissue of a user or patient. The user/patient may include any animal, human or non-human. The PPG circuit detects the light reflected from the skin tissue or transmitted through the skin tissue and generates one or more spectral responses at one or more wavelengths. A processing circuit integrated in the biosensor or in communication with the biosensor processes the spectral data to obtain a user's vitals, concentrations of substances in blood flow and/or other health information.

FIG. 1 illustrates a schematic block diagram of exemplary components in an embodiment of the biosensor 100. The biosensor 100 is configured to detect oxygen saturation (SaO2 or SpO2) levels in blood flow, as well as concentration levels of one or more other substances in blood flow of a user. In addition, the biosensor 100 is configured to detect a level of vasodilation and/or a period of vasodilation using one or more measurement techniques as described in more detail herein. The biosensor 100 includes a PPG circuit 110 as described in more detail herein.

The biosensor 100 may include one or more processing circuits 102 communicatively coupled to a memory device 104. In one aspect, the memory device 104 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board or encasement. The processing circuit 102 may also be communicatively coupled to a central control module or server in a remote location as described further herein. The biosensor 100 may be battery operated and include a battery 118, such as a lithium ion battery. The memory device 104 may store spectral data 106 or health data 120 obtained by the biosensor 100.

The biosensor 100 may include a temperature sensor 114 configured to detect a temperature of a user. For example, the temperature sensor 108 may include an array of sensors (e.g., 16×16 pixels) to detect a skin temperature of a user. The temperature sensor 114 may also be used to calibrate the PPG circuit 110, such as the wavelength output of LEDs or other light sources. The biosensor 100 may include a display 116 to display biosensor data or control interfaces for the biosensor 100.

The biosensor 100 further includes a transceiver 112. The transceiver 112 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 112 may also include a wired transceiver interface, e.g., a USB port or other type of wired connection, for communication with one or more other devices over a LAN, MAN and/or WAN. The transceiver 112 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol. The biosensor 100 may transmit health data using the transceiver 112 over a wide area network, such as a cellular network, to a third party service provider, such as a health care provider or emergency service provider.

Embodiment—PPG Circuit

Figure 2:
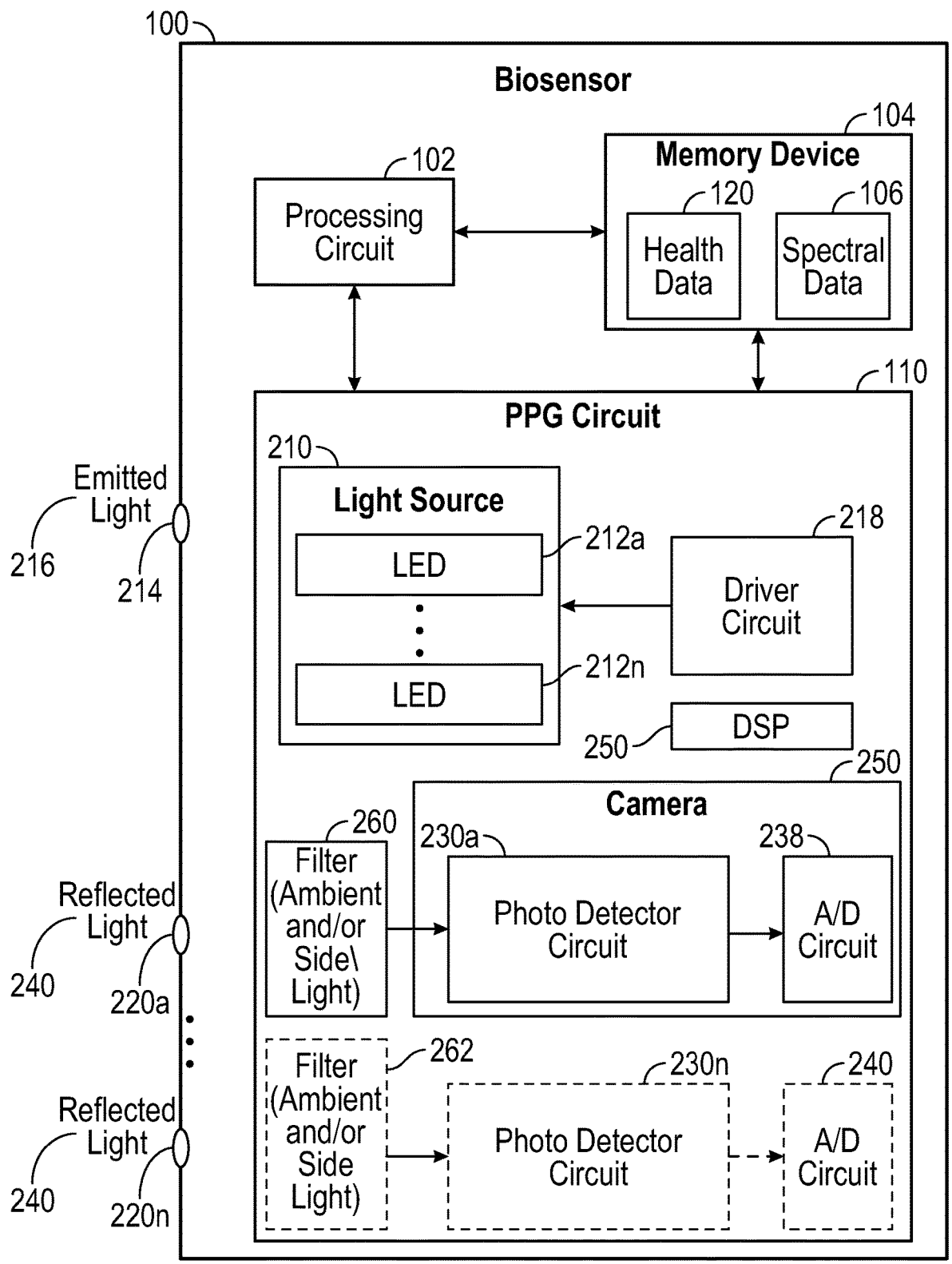
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 210 configured to emit a plurality of wavelengths of light across various spectrums. The plurality of LEDs 212a-n are configured to emit light in one or more spectrums, including infrared (IR) light, ultraviolet (UV) light, near IR light or visible light, in response to driver circuit 218. For example, the biosensor 100 may include a first LED 212a that emits visible light and a second LED 212b that emits infrared light and a third LED 212c that emits UV light, etc. In another embodiment, one or more of the light sources 210 may include tunable LEDs or lasers operable to emit light over one or more frequencies or ranges of frequencies or spectrums in response to driver circuit 218.

In an embodiment, the driver circuit 218 is configured to control the one or more LEDs 212a-n to generate light at one or more frequencies for predetermined periods of time. The driver circuit 218 may control the LEDs 212a-n to operate concurrently or consecutively. The driver circuit 218 is configured to control a power level, emission period and frequency of emission of the LEDs 212a-n. The driver circuit 218 may also tune a wavelength output of the LEDs 212a-n in response to a temperature or other feedback. The biosensor 100 is thus configured to emit one or more wavelengths of light in one or more spectrums that is directed at the surface or epidermal layer of the skin tissue of a user. The emitted light 216 passes through at least one aperture 214 and towards the surface or epidermal layer of the skin tissue of a user.

The PPG circuit 110 further includes one or more photodetector circuits 230a-n. The photodetector circuits 230 may be implemented as part of a camera 250. For example, a first photodetector circuit 230 may be configured to detect visible light and the second photodetector circuit 230 may be configured to detect IR light. Alternatively, a single photodetector 230 may be implemented to detect light across multiple spectrums. When multiple photodetectors 230 are implemented, the detected signals obtained from each of the photodetectors may be added or averaged. Alternatively, a detected light signal with more optimal signal to noise ration may be selected from the multiple photodetector circuits 230a-n.

The first photodetector circuit 230a and the second photodetector circuit 230n may also include a first filter 260 and a second filter 262 configured to filter ambient light and/or scattered light. For example, in some embodiments, only light reflected at an approximately perpendicular angle to the skin surface of the user is desired to pass through the filters. The first photodetector circuit 230a and the second photodetector circuit 230n are coupled to a first analog to digital (A/D) circuit 236 and a second A/D circuit 238. Alternatively, a single A/D circuit may be coupled to each of the photodetector circuits 230a-n. The A/D circuits convert the spectral responses to digital spectral data for processing by a DSP or other processing circuit.

The one or more photodetector circuits 230a-n include one or more types of spectrometers or photodiodes or other types of light detection circuits configured to detect an intensity of light as a function of wavelength over a time period to obtain a spectral response. In use, the one or more photodetector circuits 230a-n detect the intensity of reflected light 240 from skin tissue of a user that enters one or more apertures 220a-n of the biosensor 100. In another example, the one or more photodetector circuits 230a-n detect the intensity of light due to transmissive absorption (e.g., light transmitted through tissues, such as a fingertip or ear lobe). The one or more photodetector circuits 230a-n then obtain a spectral response (a PPG signal) of the reflected or transmissive light by measuring an intensity of the light at one or more wavelengths over a period of time.

In another embodiment, the light source 210 may include a broad spectrum light source, such as a white light to infrared (IR) or near IR LED, that emits light with wavelengths across multiple spectrums, e.g. from 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light 240 is then measured across the wavelengths in the broad spectrum, e.g. from 350 nm to 2500 nm, concurrently. In an aspect, a charge coupled device (CCD) spectrometer may be configured in the photodetector circuit 230 to measure the spectral response of the detected light over the broad spectrum.

The PPG circuit 110 may also include a digital signal processing (DSP) circuit 270 that includes signal processing of the digital spectral data. For example, the DSP circuit may determine AC or DC components from the spectral responses (PPG signals) or diastolic and systolic points or other spectral data 106. The spectral data may then be processed by the processing circuit 102 to obtain health data 120 of a user. The spectral data 106 may alternatively or in additionally be transmitted by the biosensor 100 to a central control module for processing to obtain health data 120 of a user. The spectral data 106, PPG signals, etc. may be stored in the memory device 104 of the biosensor 100.

In use, the biosensor 100 performs PPG techniques using the PPG circuit 110 to detect the concentration levels of one or more substances in blood flow. In one aspect, the biosensor 100 receives reflected light or transmissive light from skin tissue to obtain a spectral response. The spectral response includes a spectral curve that illustrates an intensity or power or energy at a frequency or wavelength in a spectral region of the detected light over a period of time. The ratio of the resonance absorption peaks from two different frequencies can be calculated and based on the Beer-Lambert law used to obtain the levels of substances in the blood flow.

For example, one or more of the embodiments of the biosensor 100 described herein is configured to detect a concentration level of one or more substances within blood flow using PPG techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level.

The spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1$, $I_1 = I_{in1} * 10^{-(\alpha_{g1}C_{gw} + \alpha_{w1}C_w)*l}$ At the second wavelength $\lambda_2$, $I_2 = I_{in2} * 10^{-(\alpha_{g2}C_{gw} + \alpha_{w2}C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I_1}{Iin_1}\right)}{\log 10\left(\frac{I_2}{Iin_2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2})*R - (\alpha_{w1} - \alpha_{gw1})}$$

The biosensor 100 may thus determine the concentration of various substances in arterial blood flow from the Beer-Lambert principles using the spectral responses of at least two different wavelengths.

Figure 3:
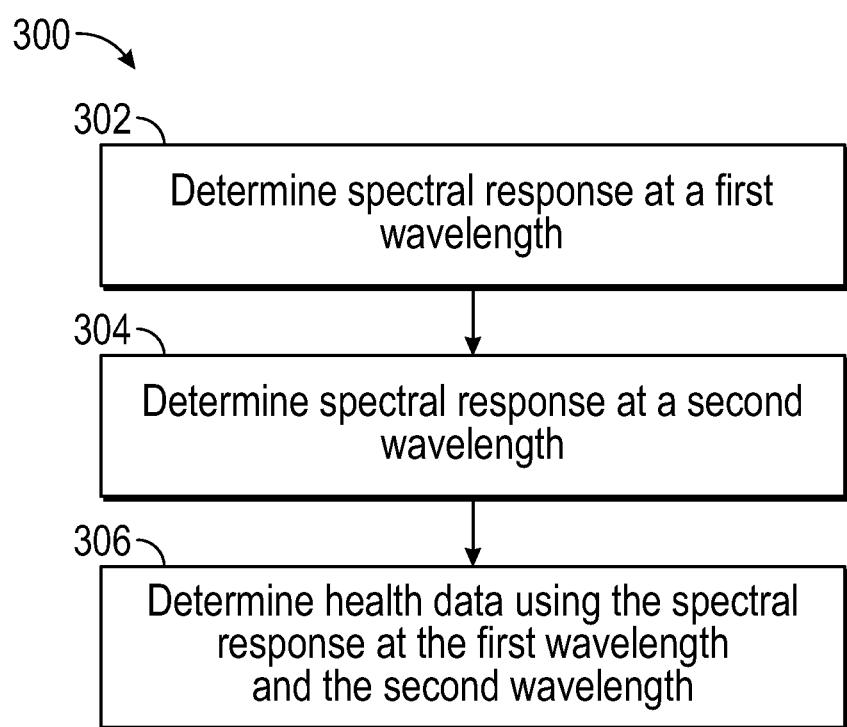
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines health data, such as an indicator or concentration level of substances in blood flow, using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of nitric oxide (NO) in blood flow using a first predetermined wavelength in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 302 and 304. The biosensor 100 analyzes the first and second spectral responses to detect an indicator or concentration level of NO in the arterial blood flow at 306. In another embodiment, using absorption coefficients for both Nitric Oxide and Hemoglobin, the concentration of Nitric Oxide can be obtained in arterial blood. A calibration table using human subjects may then correlate amounts of glucose (mG/DL) in relation to R values (NoHb) 404/940 nm.

In another example, the biosensor 100 may also detect vitals, such as heart rate, respiration rate and pulse pressure. The biosensor 100 may also determine a level of vasodilation and a period of vasodilation as described in more detail herein. Because blood flow to the skin can be modulated by multiple other physiological systems, the biosensor 100 may also be used to monitor arterial health, such as hypovolemia or other circulatory conditions.

Photoplethysmography (PPG) is used to measure time-dependent volumetric properties of blood in blood vessels due to the cardiac cycle. For example, the heartbeat affects the volume of blood flow and the concentration or absorption levels of substances being measured in the arterial blood flow. Over a cardiac cycle, pulsating arterial blood changes the volume of blood flow in a blood vessel. Incident light $I_O$ is directed at a tissue site and a certain amount of light is reflected or transmitted and a certain amount of light is absorbed. At a peak of blood flow or volume in a cardiac cycle, the reflected/transmitted light $I_L$ is at a minimum due to absorption by the increased blood volume, e.g., due to the pulsating blood in the vessel. At a minimum of blood volume during the cardiac cycle, the transmitted/reflected light $I_H$ 416 is at a maximum due to lack of absorption from the pulsating blood.

The biosensor 100 is configured to filter the reflected/transmitted light $I_L$ of the pulsating blood from the transmitted/reflected light $I_H$. This filtering isolates the light due to reflection/transmission of the pulsating blood from the light due to reflection/transmission from non-pulsating blood, vessel walls, surrounding tissue, etc. The biosensor 100 may then measure the concentration levels of one or more substances from the reflected/transmitted light $I_L$ 814 in the pulsating blood.

For example, incident light $I_O$ is directed at a tissue site at one or more wavelengths. The reflected/transmitted light I is detected by a photodetector or sensor array in a camera. At a peak of blood flow or volume, the reflected light $I_L$ 414 is at a minimum due to absorption by the pulsating blood, non-pulsating blood, other tissue, etc. At a minimum of blood flow or volume during the cardiac cycle, the Incident or reflected light $I_H$ 416 is at a maximum due to lack of absorption from the pulsating blood volume. Since the light I is reflected or traverses through a different volume of blood at the two measurement times, the measurement provided by a PPG sensor is said to be a 'volumetric measurement' descriptive of the differential volumes of blood present at a certain location within the user's vessels at different times during the cardiac cycle. These principles described herein may be applied to venous blood flow and arterial blood flow.

In general, the relative magnitudes of the AC and DC contributions to the reflected/transmitted light signal I may be determined. In general, AC contribution of the reflected light signal I is due to the pulsating blood flow. A difference function may thus be computed to determine the relative magnitudes of the AC and DC components of the reflected light I to determine the magnitude of the reflected light due to the pulsating blood flow. The described techniques herein for determining the relative magnitudes of the AC and DC contributions is not intended as limiting. It will be appreciated that other methods may be employed to isolate or otherwise determine the relative magnitude of the light $I_L$ due to pulsating blood flow (arterial and/or venous).

In one aspect, the spectral response obtained at each wavelength may be aligned based on the systolic 402 and diastolic 404 points in their respective spectral responses. This alignment is useful to associate each spectral response with a particular stage or phase of the pulse-induced local pressure wave within the blood vessel (which roughly mimics the cardiac cycle 406 and thus include systolic and diastolic stages and sub-stages thereof). This temporal alignment helps to determine the absorption measurements acquired near a systolic point in time of the cardiac cycle and near the diastolic point in time of the cardiac cycle 406 associated with the local pressure wave within the user's blood vessels. This measured local pulse timing information may be useful for properly interpreting the absorption measurements in order to determine the relative contributions of the AC and DC components measured by the biosensor 100. So, for one or more wavelengths, the systolic points 402 and diastolic points 404 in the spectral response are determined. These systolic points 402 and diastolic pointsv 404 for the one or more wavelengths may then be aligned as a method to discern concurrent responses across the one or more wavelengths.

In another embodiment, the systolic points 402 and diastolic points 404 in the absorbance measurements are temporally correlated to the pulse-driven pressure wave within the blood vessels—which may differ from the cardiac cycle.

Figure 4:
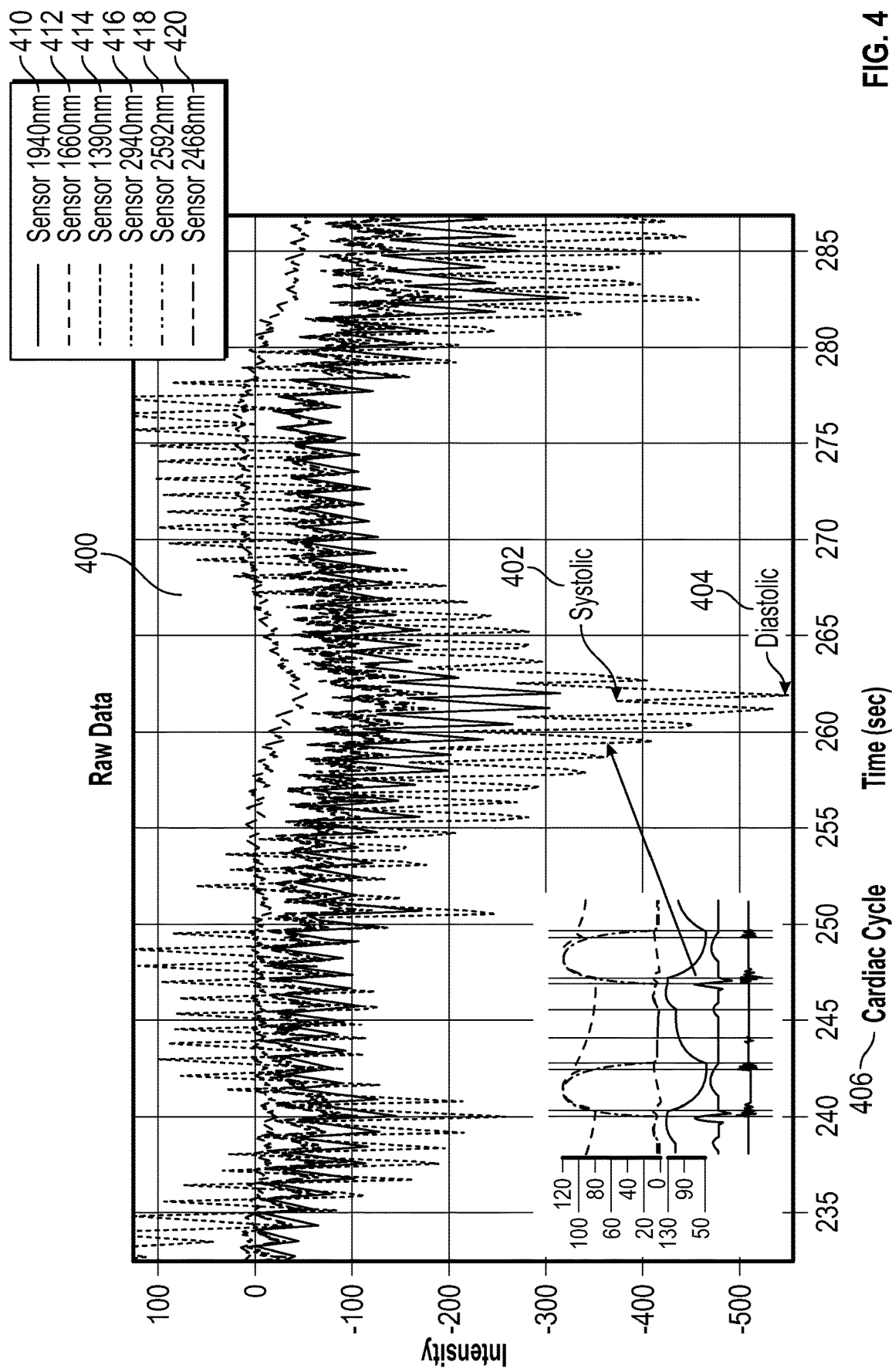
FIG. 4 illustrates the spectral response obtained at the plurality of wavelengths with the systolic points and diastolic points aligned over a cardiac cycle.

In another embodiment, the biosensor 100 may concurrently measure the intensity reflected at each the plurality of wavelengths. Since the measurements are concurrent, no alignment of the spectral responses of the plurality of wavelengths may be necessary. FIG. 4 illustrates the spectral response obtained at the plurality of wavelengths with the systolic points 402 and diastolic points 404 aligned over a cardiac cycle 406.

Figure 5:
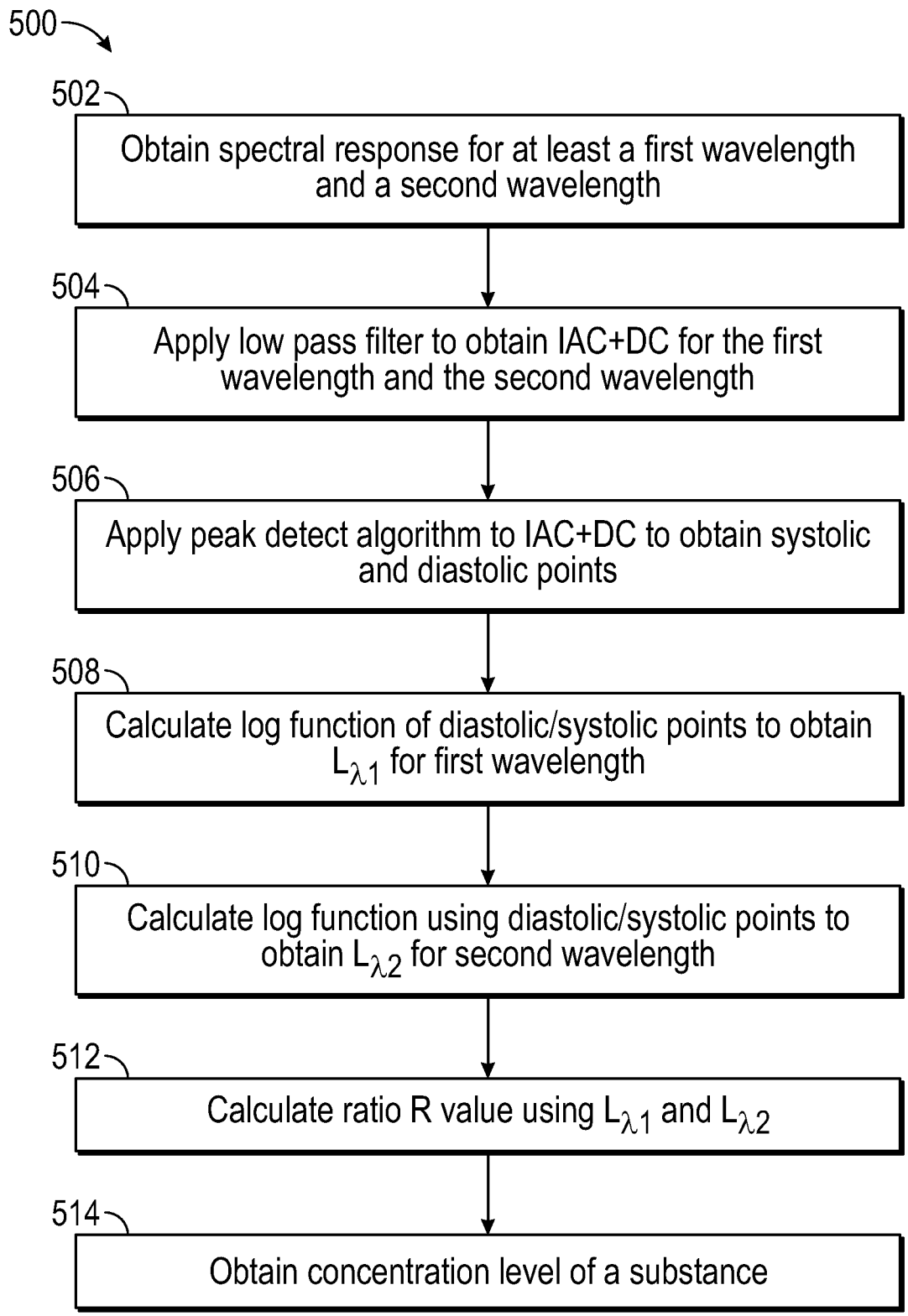
FIG. 5 illustrates a logical flow diagram of an embodiment of a method of the biosensor.

FIG. 5 illustrates a logical flow diagram of an embodiment of a method 500 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 502. The spectral responses may be measured over a predetermined period (such as 300 usec.) or at least over 2-3 cardiac cycles. This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral data obtained by the PPG circuit 110, such as the digital or analog spectral responses, may be processed locally by the biosensor 100 or transmitted to a central control module for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined. Preferably, the spectral response is obtained over at least three cardiac cycles in order to obtain a heart rate.

A low pass filter (such as a 5 Hz low pass filter) is applied to the spectral response signal at 504. The relative contributions of the AC and DC components are obtained $I_{AC+DC}$ and $I_{AC}$. A peak detection algorithm is applied to determine the systolic and diastolic points at 506. If not detected concurrently, the systolic and diastolic points of the spectral response for each of the wavelengths may be aligned or may be aligned with systolic and diastolic points of a pressure pulse waveform or cardiac cycle.

Beer Lambert equations are then applied as described herein. For example, the $L_\lambda$ values are then calculated for the first wavelength $\lambda_1$ at 508 and the second wavelength $\lambda_2$ at 510, wherein the $L_\lambda$ values for a wavelength equals:

$$L_\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC component filtered by the low pass filter. The value $L_\lambda$ isolates the spectral response due to pulsating arterial blood flow, e.g. the AC component of the spectral response.

A ratio R of the $L_\lambda$ values at two wavelengths may then be determined at 512. For example, the ratio R may be obtained from the following:

$$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The concentration level of a substance may then be obtained from the R value and a calibration database at 514. The biosensor 100 may continuously monitor a user over 2-3 hours or continuously over days or weeks.

In one embodiment, the $R_{390,940}$ value with $L_{\lambda 1=390\,nm}$ and $L_{\lambda 2=940}$ may be non-invasively and quickly and easily obtained using the biosensor 100 to determine a concentration level of nitric oxide NO in blood flow of a user. In particular, in unexpected results, it is believed that the nitric oxide NO levels in the blood flow is being measured at least in part by the biosensor 100 at wavelengths in the range of 380-410 and in particular at $\lambda_1$=390 nm. Thus, the biosensor 100 measurements to determine the $L_{390\,nm}$ values are the first time NO concentration levels in arterial blood flow have been measured directly in vivo. These and other aspects of the biosensor 100 are described in more detail herein with clinical trial results.

Figure 6:
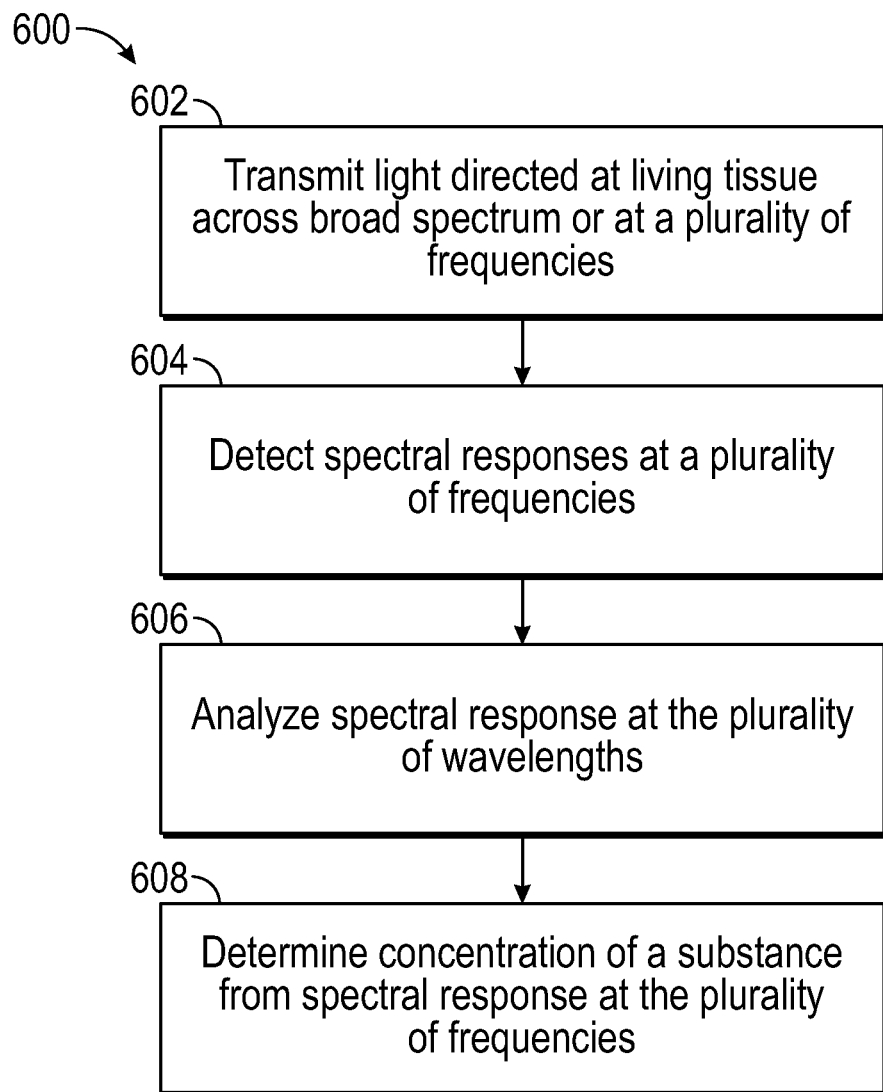
FIG. 6 illustrates a logical flow diagram of an exemplary method to determine levels of a substance in blood flow using the PPG signals at a plurality of wavelengths.

Embodiment—Determination of Concentration Level of a Substance Using PPG Signals at a Plurality of Wavelengths FIG. 6 illustrates a logical flow diagram of an exemplary method 600 to determine levels of a substance in blood flow using the PPG signals at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu_i * C_i$$

wherein,
$I_{1-n}$=intensity of light at wavelengths $\lambda_{1-n}$
$\mu_n$=absorption coefficient of substance 1, 2, . . . n at wavelengths $\lambda_{1-n}$
$C_n$=Concentration level of substance 1, 2, . . . n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 602. The spectral response of light from the skin tissue is detected at 604, and the spectral responses are analyzed at a plurality of wavelengths (and in one aspect including a range of +/−10 to 50 nm around each of the wavelengths) at 606. Then, the concentration level C of the substance may be determined using the spectral responses at the plurality of wavelengths at 608. The concentration level of the substance may be isolated from isoforms or other compounds by compensating for the concentration of the compounds. For example, using absorption coefficients for Nitric Oxide and Hemoglobin, the concentration of Nitric Oxide can be obtained in arterial blood. A calibration table using human subjects may then to correlate amounts of glucose (mG/DL) in relation to R values (NoHb) 404/940 nm.

Figure 7:
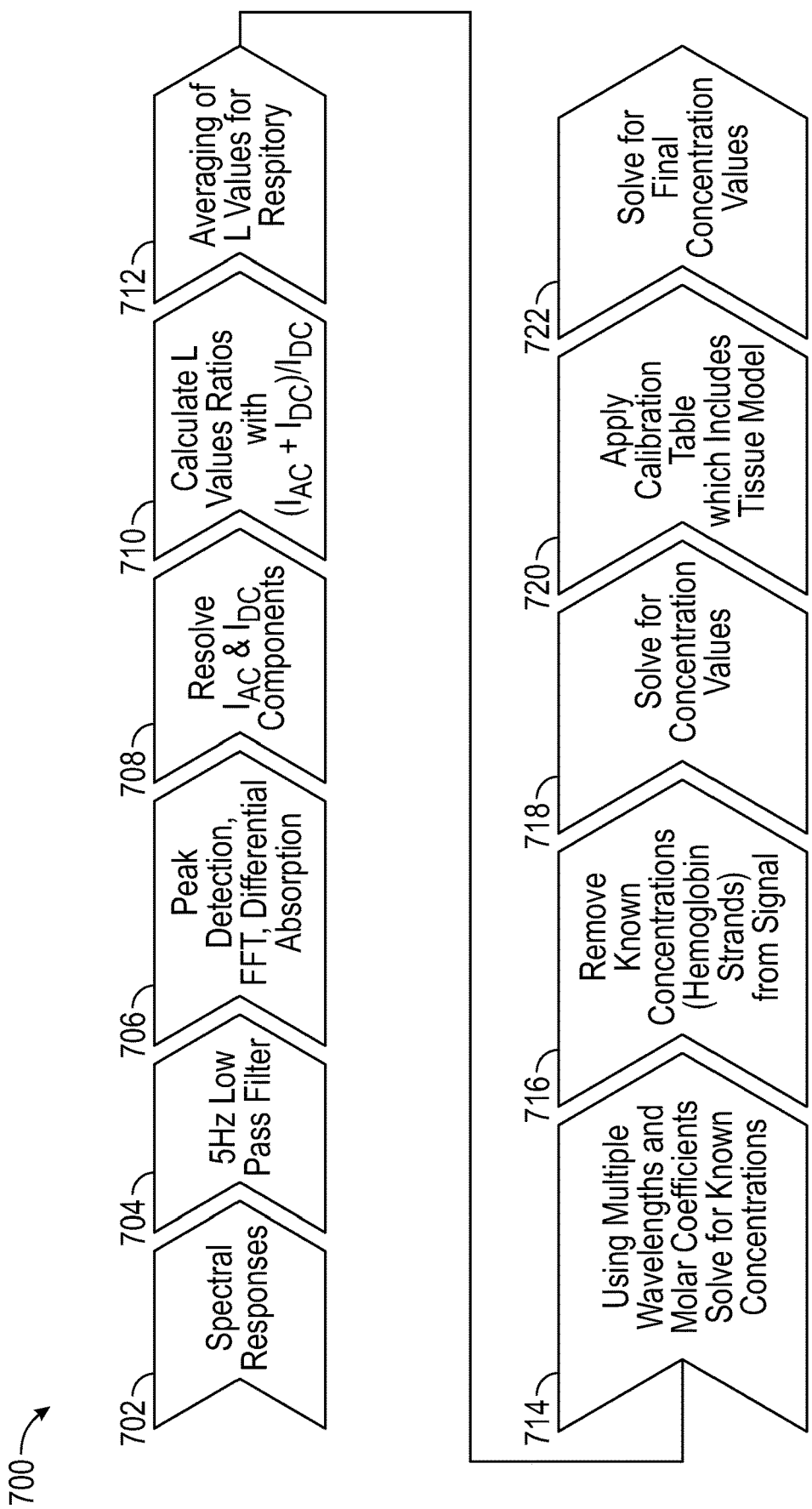
FIG. 7 illustrates a logical flow diagram of an exemplary method to determine levels of a substance using the spectral responses at a plurality of wavelengths in more detail.

FIG. 7 illustrates a logical flow diagram of an exemplary method 700 to determine levels of a substance using the spectral responses at a plurality of wavelengths in more detail. The spectral responses are obtained at 702. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 704. The AC fluctuation is due to the pulsatile expansion of the vessels due to the volume increase in pulsating blood. In order to measure the AC fluctuation, measurements are taken at different times and a peak detection algorithm is used to determine the diastolic point and the systolic point of the spectral responses at 706. A Fast Fourier transform (FFT) algorithm may also be used to isolate the DC component $I_{DC}$ and AC component of each spectral response signal at 706. A differential absorption technique may also be used as described in more detail herein. The $I_{DC}$ component is thus isolated from the spectral signal at 708.

The $I_{AC+DC}$ and $I_{DC}$ components are then used to compute the L values at 710. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 712.

In an embodiment, isoforms of a substance may be attached in the blood stream to one or more types of hemoglobin compounds. The concentration level of the hemoglobin compounds may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm (+/−20 nm) may include a concentration level of the hemoglobin compounds as well as nitric oxide. The hemoglobin compound concentration levels must thus be compensated for to isolate the nitric oxide concentration levels. Multiple wavelengths and absorption coefficients for hemoglobin are used to determine a concentration of the hemoglobin compounds at 714. Other methods may also be used to obtain a concentration level of hemoglobin in the blood flow as well. The concentration of the hemoglobin compounds is then adjusted from the measurements at 716. The concentration values of the substance may then be obtained at 718. For example, the R values are then determined at 718.

To determine a concentration level of the substance, a calibration table or database is used that associates the obtained R value to a concentration level of the substance at 720. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics. The concentration level of the substance in blood flow is then obtained using the calibration table at 722. The concentration level may be expressed as mmol/liter, as a saturation level percentage, as a relative level on a scale, etc.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

The biosensor 100 may detect nitric oxide in vivo using PPG techniques by measuring the shift in the absorbance spectra curve of reduced hemoglobin in tissue and/or arterial blood flow. The absorbance spectra curve shifts with a peak from around 430 nm to a peak around 411 nm depending on the production of methemoglobin. The greater the degree of the shift of the peak of the curve, the higher the production of methemoglobin and NO concentration level. Correlations may be determined between the degree of the measured shift in the absorbance spectra curve of reduced hemoglobin to an NO concentration level. The correlations may be determined from a large sample population or for a particular user and stored in a calibration database. The biosensor 100 may thus obtain an NO concentration level by measuring the shift of the absorbance spectra curve of reduced hemoglobin. A similar method of determining shifts in absorbance spectra may be implemented to determine a blood concentration level of other substances.

The biosensor 100 may obtain an NO concentration level by measuring the shift of the absorbance spectra curve of deoxygenated hemoglobin and/or by measuring the shift of the absorbance spectra curve of oxygenated hemoglobin in vivo. The biosensor 100 may then access a calibration database that correlates the measured shift in the absorbance spectra curve of deoxygenated hemoglobin to an NO concentration level. Similarly, the biosensor may access a calibration database that correlates the measured shift in the absorbance spectra curve of oxygenated hemoglobin to an NO concentration level.

Figure 8:
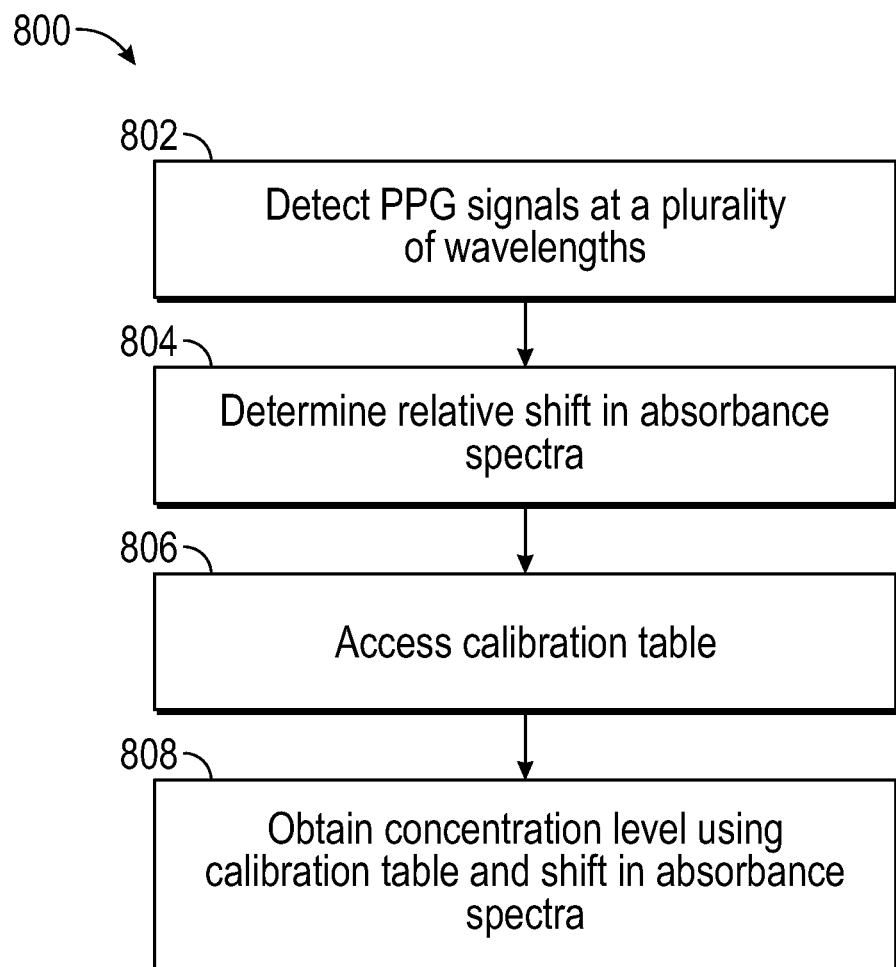
FIG. 8 illustrates a logical flow diagram of an exemplary embodiment of a method for measuring a concentration level of a substance in vivo using shifts in absorbance spectra.

FIG. 8 illustrates a logical flow diagram of an exemplary embodiment of a method 800 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects PPG signals at a plurality of wavelengths with a high absorption coefficient of the one or more substances that interact with the substance at 802. The biosensor 100 determines the relative shift in the absorbance spectra for the substance at 804. For example, the biosensor 100 may measure the absorbance spectra curve of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 806. The biosensor 100 may thus obtain a concentration level of the substance in blood flow using a calibration database and the measured relative shift in absorbance spectra at 808.

The various methods thus include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies. The biosensor 100 may use a plurality of these methods to determine a plurality of values for the concentration level of the substance. The biosensor 100 may determine a final concentration value using the plurality of values. For example, the biosensor 100 may average the values, obtain a mean of the values, etc.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Respiration Rate, Heart Rate and Pulse Pressure

Figure 9:
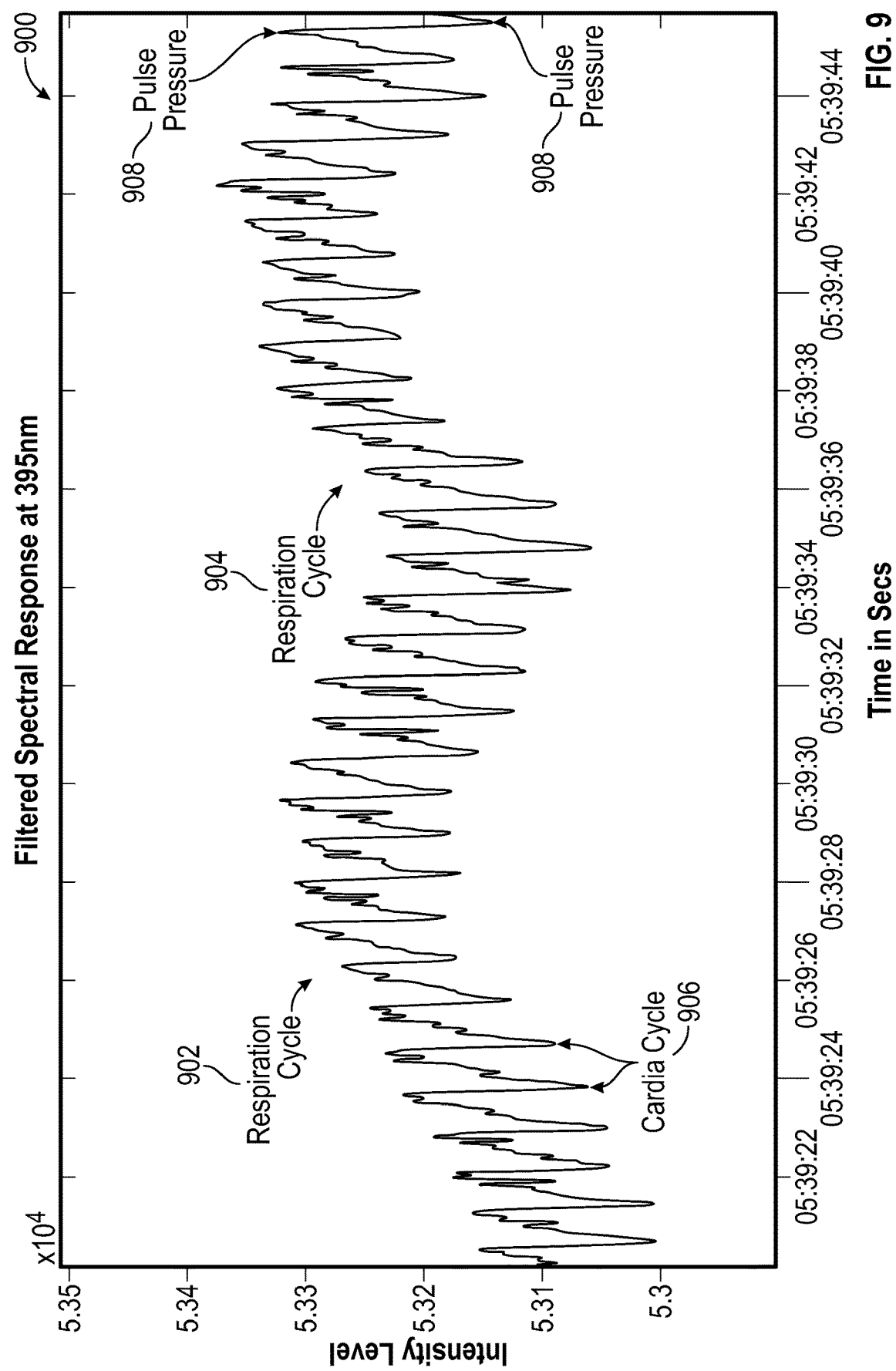
FIG. 9 illustrates a schematic drawing of an exemplary embodiment of a spectral response obtained using an embodiment of the biosensor.

FIG. 9 illustrates a schematic drawing of an exemplary embodiment of a PPG Signal 900 obtained using an embodiment of the biosensor 100 from a user. The PPG Signal 900 was obtained at a wavelength of around 395 nm and is illustrated for a time period of about 40 seconds. The PPG Signal 900 was filtered using digital signal processing techniques to eliminate noise and background interference to obtain the filtered PPG Signal 900. A first respiration cycle 902 and a second respiration cycle 904 may be obtained by measuring a low frequency component or fluctuation of the filtered PPG Signal 900. From this low frequency component, the biosensor 100 may obtain a respiratory rate of a user from the PPG Signal 900.

A heart rate may be determined from the spectral response. For example, the biosensor 100 may determine the time between diastolic points or between systolic points to determine a time period of a cardiac cycle 906. In another embodiment, to estimate the heart rate, the frequency spectrum of the PPG signal is obtained using a FFT algorithm over a predetermined period (hamming window). The pulse rate is estimated as the frequency that corresponds to the highest power in the estimated frequency spectrum. The frequency spectrum may be averaged over a time period, such as a 5-10 second window.

A pulse pressure 908 may be determined from the PPG signal 900. The pulse pressure 908 corresponds to an amplitude of the PPG signal 900 or a peak to peak value. The amplitude of the PPG signal 900 may be averaged over a time period to determine a pulse pressure 908.

Thus, a PPG signal may be used to determine heart rate, respiration rate and pulse rate. A light source in the UV range provides a PPG signal with a lower signal to noise ratio for determining heart rate and respiration rate in some tissue while a light source in the IR range provides a PPG signal with a lower signal to noise ratio in other types of tissue. The infrared range (IR) range may include wavelengths from 650 nm to 1350 nm.

Figure 10:
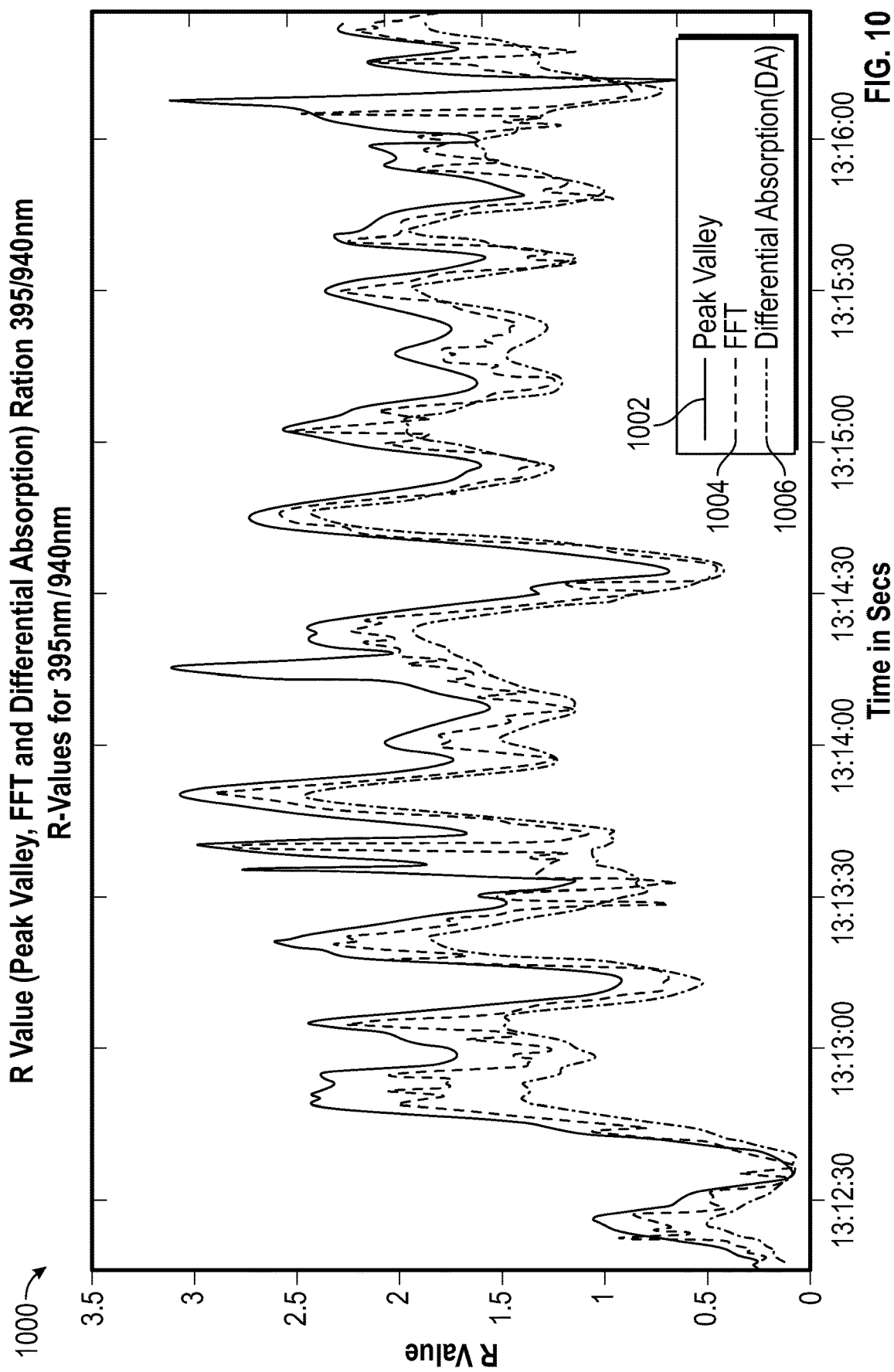
FIG. 10 illustrates a schematic drawing of an exemplary embodiment of results of R values determined using a plurality of methods.

FIG. 10 illustrates a schematic drawing of an exemplary embodiment of results of R values 1000 determined using a plurality of methods. The R values 1000 corresponding to the wavelengths of 395 nm/940 nm is determined using three methods. The R Peak Valley curve 1002 is determined using the Ratio $$R = \frac{L395}{L940}$$

as described hereinabove. The R FFT curve 1004 is obtained using FFT techniques to determine the $I_{DC}$ values and $I_{AC}$ component values of the spectral responses to determine the Ratio $$R = \frac{L395}{L940}.$$

The R differential absorption curve 1006 is determined using the shift in absorbance spectra as described in more detail in U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, and hereby expressly incorporated by reference herein.

As seen in FIG. 10, the determination of the R values using the three methods provides similar results, especially when averaged over a period of time. A mean or average of the R values 1002, 1004 and 1006 may be calculated to obtain a final R value or one of the methods may be preferred depending on the positioning of the biosensor or underlying tissue characteristics.

Figure 11A:
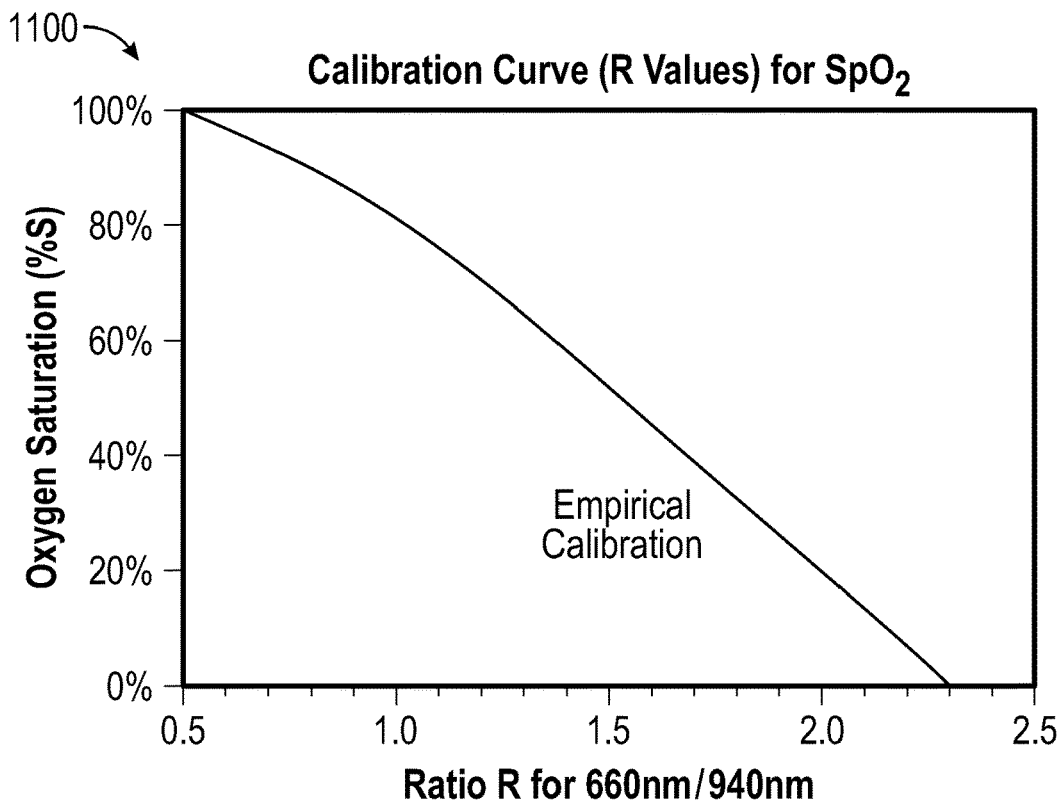
FIG. 11A illustrates a schematic drawing of an exemplary embodiment of an empirical calibration curve for correlating oxygen saturation levels ($SpO_2$) with R values.

FIG. 11A illustrates a schematic drawing of an exemplary embodiment of an empirical calibration curve 1100 for correlating oxygen saturation levels (SpO$_2$) with R values. The calibration curve 1100 may be included as part of the calibration database for the biosensor 100. For example, the R values may be obtained for $L_{660\ nm}/L_{940\ nm}$. In one embodiment, the biosensor 100 may use a light source in the 660 nm wavelength or in a range of +/−50 nm to determine SpO$_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 11B:
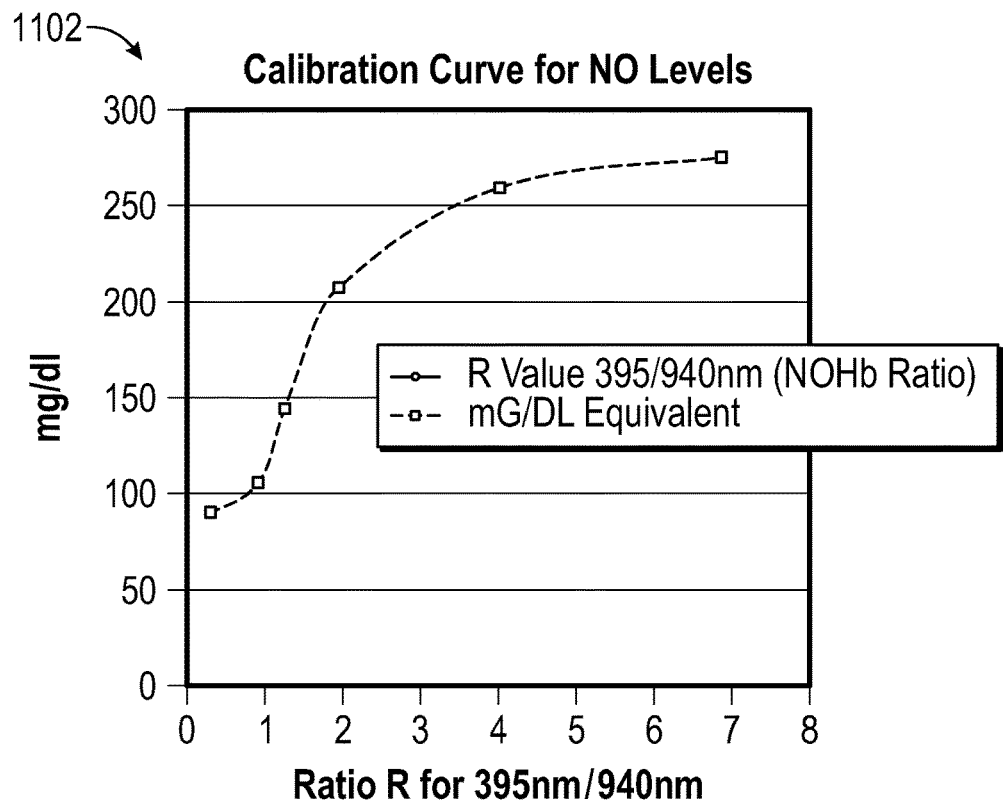
FIG. 11B illustrates a schematic drawing of an exemplary embodiment of an empirical calibration curve for correlating NO levels with R values.

FIG. 11B illustrates a schematic drawing of an exemplary embodiment of an empirical calibration curve 1102 for correlating NO levels (mg/dl) with R values. The calibration curve 1102 may be included as part of the calibration database for the biosensor 100. For example, the R values may be obtained in clinical trials from measurements of $L_{395\ nm}/L_{940\ nm}$ and the NO levels of a general sample population. The NO levels may be measured using one or more other techniques for verification to generate such a calibration curve 1102. This embodiment of the calibration curve 1102 is based on limited clinical data and is for example only. Additional or alternative calibration curves 1212 may also be derived from measurements of a general population of users at one or more different positions of the biosensor 100. For example, a first calibration curve may be obtained at a forehead, another for an abdominal area, another for a fingertip, another for a palm, etc.

From the clinical trials, the L values obtained at wavelengths around 390 nm (e.g. 380-410) are measuring nitric level (NO) levels in the arterial blood flow. The R value for L390/L940 nm may thus be used to obtain NO levels in the pulsating blood flow. From the clinical trials, it seems that the NO levels are reflected in the R values obtained from L390 nm/L940 nm and wavelengths around 390 nm such as L395 nm/L940 nm. The NO levels may thus be obtained from the R values and a calibration database that correlates the R value with known concentration levels of NO.

In other embodiments, rather than $L\lambda1=390$ nm, the L value may be measured at wavelengths in a range from 410 nm to 380 nm, e.g., as seen in the graphs wherein $L\lambda1=395$ nm is used to obtain a concentration level of NO. In addition, $L\lambda2$ may be obtained at any wavelength at approximately 660 nm or above. Thus, R obtained at approximately $L\lambda1=380$ nm-400 nm and $L\lambda2 \geq 660$ nm may also be obtained to determine concentration levels of NO.

In an embodiment, the concentration level of NO may be correlated to a diabetic risk or to blood glucose levels using a calibration database.

Embodiment—Detection of a Risk of Sepsis or an Infection Based on NO Levels

In an embodiment, the biosensor 100 may detect a risk of sepsis using NO concentration levels. In this embodiment, an R value derived from L395 and L940 is used to determine an NO measurement though other thresholds may be obtained using other NO measurements, such as R390/940 or L390. In the clinical trials herein, the R395/940 value for a person without a sepsis condition was in a range of 0.1-8. In addition, it was determined that the R395/940 value of 30 or higher is indicative of a patient with a sepsis condition and that the R395/940 value of 8-30 was indicative of a risk of sepsis in the patient. In general, the R395/940 value of 2-3 times a baseline of the R395/940 value was indicative of a risk of sepsis in the patient. These ranges are based on preliminary clinical data and may vary. In addition, a position of the biosensor, pre-existing conditions of a patient or other factors may alter the numerical values of the ranges of the R395/940 values described herein.

The R values are determined by using a wavelength in the UV range with high absorption coefficient for NO, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So, these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

A baseline NO measurement in blood vessels of a healthy general population is obtained. For example, the biosensor 100 may obtain R values or other NO measurements using the biosensor 100. For example, the biosensor 100 may measure an L395 value or determine SpNO % based on an R value for a general population over a period of time, such as hours or days. These NO measurements are then averaged to determine a baseline NO measurement. The NO measurement in blood vessels is then obtained for a general population with a diagnosis of sepsis. For example, the biosensor 100 may obtain R values or other NO measurements (such as an L395 value or SpNO %) for patients diagnosed with sepsis using traditional blood tests, such as serum lactate blood tests. The biosensor 100 may monitor the patients throughout the diagnosis and treatment stages. The NO measurements are then averaged to determine a range of values that indicate a septic condition.

Predetermined thresholds may then be obtained from the NO measurements. For example, a threshold value indicative of a non-septic condition may be obtained. A threshold value for a septic condition may also be obtained. The biosensor 100 is then configured with the predetermined thresholds for the NO measurement.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Embodiment—Detection of Other Conditions Based on NO Levels

In another embodiment, post-traumatic stress disorder (PTSD) may result in higher than normal NO levels. There are several reports that increased oxidative stress may be a factor in the evolution of some enduring neurological and psychiatric disorders and PTSD (Bremner, 2006). Stress, a risk factor for developing PTSD, evokes a sustained increase in nitric oxide synthase (NOS) activity that can generate excessive amounts of nitric oxide (Harvey et al., 2004). Oxidation of nitric oxide produces peroxynitrite that is very toxic to nerve cells (Ebadi et al., 2001), and elevated levels of peroxynitrite and its precursor nitric oxide have been observed in patients with PTSD. (Tezcan et al., 2003). The article by Kedar N. Prasad and Stephen C. Bondy, entitled, "Common biochemical defects linkage between post-traumatic stress disorders, mild traumatic brain injury (TBI) and penetrating TBI," Brain Research, Volume 1599, Pages 103-114, Mar. 2, 2015, and incorporated by reference herein, describes the elevation of nitric oxide NO that may indicate PTSD. The biosensor 100 may operate in one or more modes to detect or provide a warning of abnormal NO levels that may indicate PTSD.

In another embodiment, concussions, mild traumatic brain injury (TBI) and penetrating TBI, may also result in abnormal NO levels. The article by James H. Silver, entitled, "Inorganic Nitrite as a Potential Therapy or Biomarker for Concussion," J. Neurol Neurophysiol, Volume 7, Issue 2 (April 2016), and incorporated by reference herein, describes an abnormal pattern of nitric oxide NO levels after a concussion. For example, it has been observed that a rapid increase in nitric oxide occurs within minutes following head injury, followed by a decline to below baseline within hours. The biosensor 100 may monitor NO levels after a head trauma and detect this sudden increase and then reduction below baseline in NO levels. In use, a baseline level of NO may be determined for a user during normal conditions. After a potential head injury, the user is then monitored by the biosensor 100 for changes from this baseline level of NO. This process may be performed, e.g., for sideline evaluation of potentially concussed athletes. Thus, the biosensor 100 may operate in one or more modes to monitor NO levels and provide a warning of abnormal NO levels that may indicate a concussion or TBI.

In one or more modes of operation, the biosensor 100 may thus be configured to detect one or more of these other substances in addition to or alternatively from NO levels in blood flow.

Figure 12:
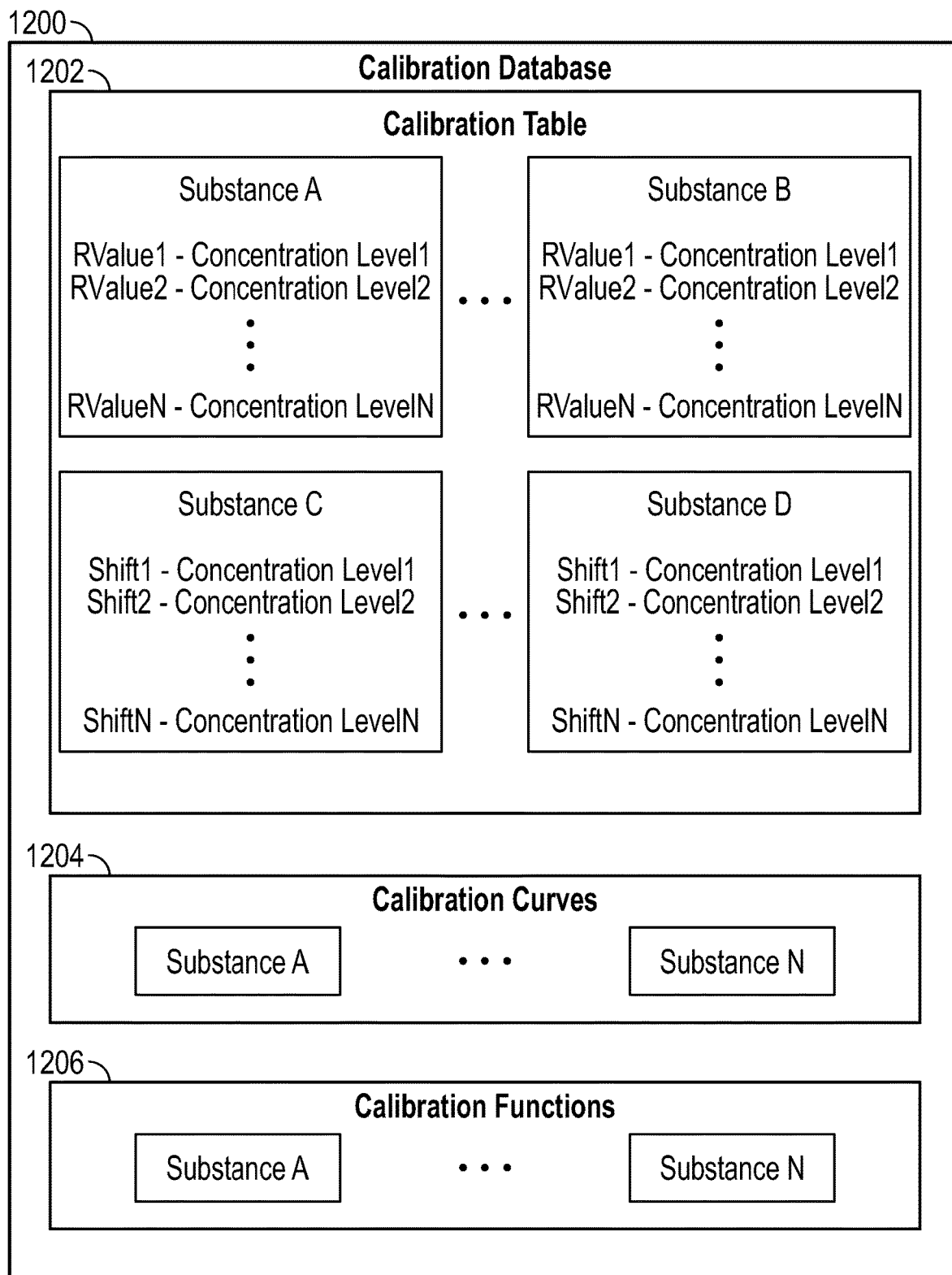
FIG. 12 illustrates a schematic block diagram of an embodiment of a calibration database.

FIG. 12 illustrates a schematic block diagram of an embodiment of a calibration database 1200. The calibration database 1200 includes one or more calibration tables 1202, calibration curves 1204 or calibration functions 1206 for correlating obtained values to concentration levels of one or more substances A-N. The concentration level of the substances may be expressed in the calibration tables 1202 as units of mmol/liter, as a saturation level percentage (SpNO %), as a relative level on a scale (e.g., 0-10), etc.

The calibration database 1200 may also include one or more calibration tables for one or more underlying skin tissue types. In one aspect, the calibration database 1200 may correlate an R value to a concentration level of a substance for a plurality of underlying skin tissue types.

In another aspect, a set of calibration tables 1202 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1202 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1200 may also include a set of calibration curves 1204 for a plurality of substances A-N. The calibration curves may correlate L values or R values or degree of shifts of spectral data to concentration levels of the substances A-N.

The calibration database 1200 may also include calibration functions 1206. The calibration functions 1206 may be derived (e.g., using regressive functions) from the correlation data from the calibration curves 1204 or the calibration tables 1202. The calibration functions 1206 may correlate L values or R values or degree of shifts in spectral data to concentration levels of the substances A-N for one or more underlying skin tissue types.

Embodiment—Neural Network

One or more types of artificial neural networks (a.k.a. machine learning algorithms) may be implemented herein to determine health data from PPG signals. For example, neural networks may be used to obtain a concentration level of NO or glucose or other health data from input data derived from PPG signals. Neural network models can be viewed as simple mathematical models defining a function $f$ wherein $f:X \rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc.). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 13:
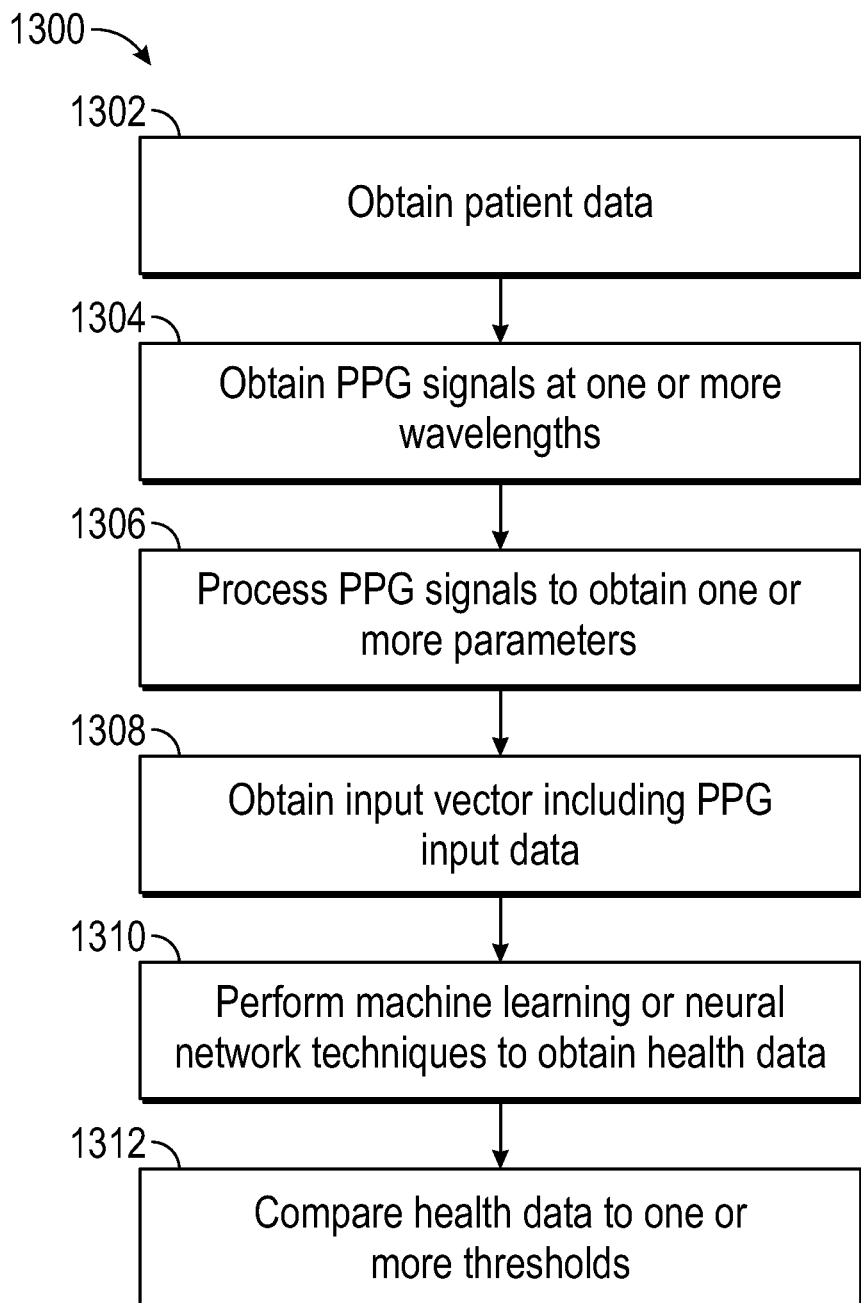
FIG. 13 illustrates a logical flow diagram of an embodiment of a method for using a machine learning neural network technique for detection of health data.

FIG. 13 illustrates a logical flow diagram of an embodiment of a method 1300 for using a machine learning neural network technique for detection of health data. In an embodiment, patient data is obtained at 1302. The patient data may include one or more of: age, weight, body mass index, temperature, blood pressure, pre-existing medical conditions, trauma events, mental conditions, injuries, demographic data, physical examinations, laboratory tests, diagnosis, treatment procedures, prescriptions, radiology examinations, historic pathology, medical history, surgeries, etc. PPG signals at one or more wavelengths are obtained at 1304.

Various parameters of the PPG signals may be determined or measured at 1306 These parameters include the diastolic and systolic points, transfer functions, timing differences between wavelengths, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. These and other parameters may be obtained using a PPG signal. The PPG input data may include the PPG signals, and/or one or more parameters derived from the PPG signals.

An input vector is obtained at 1308. The input vector includes the PPG input data, such as the PPG signals at one or more wavelengths and/or one or more parameters generated from the PPG signals at the one or more wavelengths. Since the PPG signal is of variable duration, a fixed dimension vector for a measurement of the PPG signal may be obtained. The input vector may also include patient data.

The input vector is processed by a processing device executing a neural network (aka machine learning algorithm). The processing device executes the machine learning algorithm or neural network techniques using the input vector to determine health data at 1310. The health data includes one or more of heart rate, period of vasodilation, level of vasodilation, respiration rate, blood pressure, oxygen saturation level, NO level, liver enzyme level, Glucose level, Blood alcohol level, blood type, sepsis risk factor, infection risk factor, cancer, virus detection, creatinine level or electrolyte level. The health data may also include blood viscosity, blood pressure, arterial stiffness, vascular health, cardiovascular risk, atherosclerosis, etc. The health data may be generated as an output fixed length vector.

The obtained health data may be compared to expected ranges or thresholds in a calibration table at 1312. Alarms or warnings may be issued based on the comparison.

Embodiment—Measurement of Vasodilation Using PPG Signals

Vasodilation is the widening of blood vessels. It results from relaxation of smooth muscle cells within the vessel walls, in particular in the large veins, large arteries, and smaller arterioles. The process is the opposite of vasoconstriction, which is the narrowing of blood vessels due to constriction of the smooth muscle cells within the vessels walls. The vascular endothelium is crucially involved in the fundamental regulation of blood flow matching demand and supply of tissue. After transient ischemia, arterial inflow increases. As a response to increased shear forces during reactive hyperemia, healthy arteries dilate via release of NO or other endothelium-derived vasoactive substances. This endothelium-dependent flow-mediated vasodilation (FMD) is impaired in atherosclerosis.

The capacity of blood vessels to respond to physical and chemical stimuli in the lumen confers the ability to self-regulate tone and to adjust blood flow and distribution in response to changes in the local environment. Many blood vessels respond to an increase in flow, or more precisely shear stress, by dilating. This phenomenon is designated flow-mediated vasodilation (FMD). A principal mediator of FMD is endothelium-derived NO—an example of an EDRF.

Although the precise mechanism by which vasodilation occurs during reactive hyperemia in FMD measurement has not been fully elucidated, nitric oxide (NO) has been proposed as a principal mediator of FMD. The NO, produced as a result of an increase of endothelial NO synthase activity induced by shear stress, diffuses into the tunica media, leading to relaxation of smooth muscle cells and subsequent vasodilation. The assessment of endothelial function by FMD, therefore, presupposes a normal structural condition. Impaired endothelium-independent vasodilation is thought to be associated with structural vascular alterations and alterations in smooth muscle cells, e.g. as a result of atherosclerosis.

As the presence of endothelial dysfunction is closely associated with cardiovascular risk and outcome, the measurement of FMD in the brachial artery has become a standard method for the assessment of endothelial function in patients and to evaluate therapeutic interventions targeting atherosclerosis. For example, in healthy humans, the relative increase in brachial artery diameter during vasodilation is typically in the 5% to 10% range.

The current measurement of FMD in the brachial artery requires using high-frequency ultrasound to visually inspect the brachial artery. For example, one process includes applying a stimulus to provoke the endothelium to release nitric oxide (NO) with subsequent vasodilation that is then imaged and quantitated as an index of vasomotor function. This process of high-resolution ultrasonography of the brachial artery to evaluate FMD has limitations. It must be performed in a clinical setting by a medical clinician using expensive ultrasonography equipment.

Thus, there is a need for an improved system and method for detection of vasodilation and conditions affected by vasodilation and conditions that affect vasodilation. The systems and methods used to describe detection of a level of vasodilation and periods of vasodilation may be used to determine vasoconstriction.

In various embodiments described herein, vasodilation and characteristics thereof may be measured using PPG signals obtained by the biosensor. The effects of vasodilation may be observed in PPG signals in one or more of a plurality of wavelengths across different spectrums, such as IR, visible and UV. For example, PPG signals across the spectrum may vary in shape, intensity level and timing due to vasodilation. In one example, the effect of vasodilation is observed from phase differences between PPG signals of different wavelengths, especially between wavelengths in different spectrums. Vasodilation also causes subtle skin movement which may be observed in PPG signals, especially in lower frequency components of PPG signals (e.g. frequencies that do not reflect the pulsatile blow flow). Using one or more characteristics of the PPG signals, a level of vasodilation may be obtained. The level of vasodilation may be measured as a percentage change in the size of vessels, such as percentage increase in a baseline diameter or planar area, or in a range such as 1-10, or in other manners.

In addition, an arterial stiffness or elasticity index may be obtained using the PPG signals. The PPG signals may predict vascular health, such as atherosclerosis. For example, a timing or period to change from a state of vasodilation to normal width may be obtained using phase differences between different wavelengths. The rate of change may indicate vascular stiffness and a prediction of vascular health.

In another embodiment, the level of vasodilation may be used to calibrate measurement of oxygen saturation SpO2 or other measurements of concentration of substances in blood flow. For example, measurements of oxygen saturation levels may be in error during periods of vasodilation. These measurements of oxygen saturation during vasodilation may be identified and flagged and/or the measurements may be calibrated in response to a level of vasodilation.

The biosensor described herein obtains PPG signals and measures a relative level of vasodilation of vessels and a period of vasodilation. For example, the PPG signal measures the pressure wave of blood flow through vessels. Vasodilation changes the propagation properties of blood flow through vessels, and thus the PPG signal changes. The changes in PPG signals due to the changing propagation properties is reflected in a transfer function generated from the PPG signals, e.g. time differences and wave shape differences between PPG signals. The transfer function may be measured to determine a level of vasodilation in real time.

Figure 14:
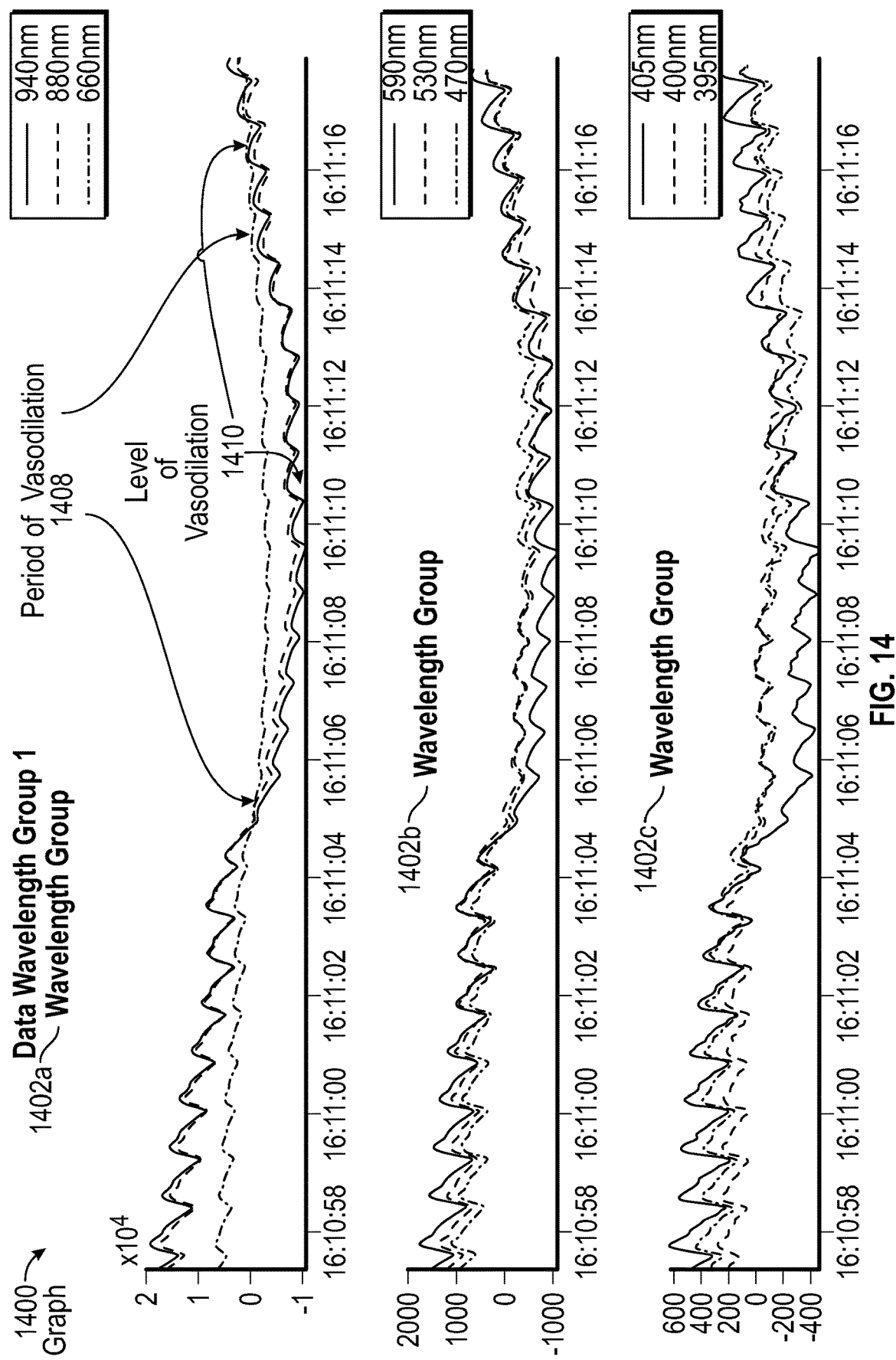
FIG. 14 illustrates a schematic diagram of a graph of PPG signals during a period of vasodilation in vessels.

FIG. 14 illustrates a schematic diagram of a graph 1400 of PPG signals during a period of vasodilation in vessels. At "rest", a body responds to caloric intake and vasodilation occurs normally as the body processes food, insulin is dispensed, and arteries expand due to Nitric Oxide (NO) causing the outer muscle of the arteries to expand temporarily. This vasodilation is reflected in the PPG signal, and highly visible in the signal to noise ratio.

The biosensor 100 obtained a PPG signal during vasodilation after caloric intake around a wavelength at 940 nm, a wavelength at 880 nm and a wavelength at 660 nm as shown in the PPG Signals for Wavelength Group 1402a. The biosensor 100 also obtained the spectral response for a wavelength at 590 nm, a wavelength at 530 nm and a wavelength at 470 nm as shown in the PPG Signals for Wavelength Group 1402b. The biosensor 100 further obtained the spectral response for a wavelength at 405 nm, a wavelength at 400 nm and a wavelength at 395 nm as shown in the PPG Signals for Wavelength Group 1402*c*.

As shown in the graphs, the PPG signals reflect a period of vasodilation 1408. The vasodilation 1304*a-c* is reflected in the PPG signals during a time period between approximately 16.11.04 secs through approximately 16.11.17 secs. In particular, a lower frequency component of the PPG signals changes during the period of vasodilation 1408. This lower frequency component of the PPG signals includes the lower frequencies not affected by the pulsating blood flow (pressure wave) due to the cardiac cycle.

During vasodilation, the arteries and other vessels widen changing the absorption properties of the vascular tissue. These changes in absorption properties are due, e.g., by the increase in blood in the vascular tissue and the compression of surrounding tissue due to the widening vessels. The PPG signals across wavelengths in the IR, visible and UV spectrums are affected by the changing absorption properties of the vascular tissue due to vasodilation.

The level of vasodilation 1410 may be obtained from the PPG signals. For example, the change in low frequency from the PPG signal may be correlated to a level of vasodilation. The level of vasodilation may be expressed as a percentage change of the diameter or planar area of the vessel or percentage increase in blood flow during the period of vasodilation. The level of vasodilation may alternatively be measured in a range such as 1-10, or in other manners.

The duration of the vasodilation may also be obtained from the PPG signals. The beginning of vasodilation and end of vasodilation may be identified from the PPG signals. For example, the vasodilation begins at approximately 16.11.04 secs and ends at approximately 16.11.17 secs in Graph 1400 and so indicates a period of vasodilation of 13 seconds.

Figure 15:
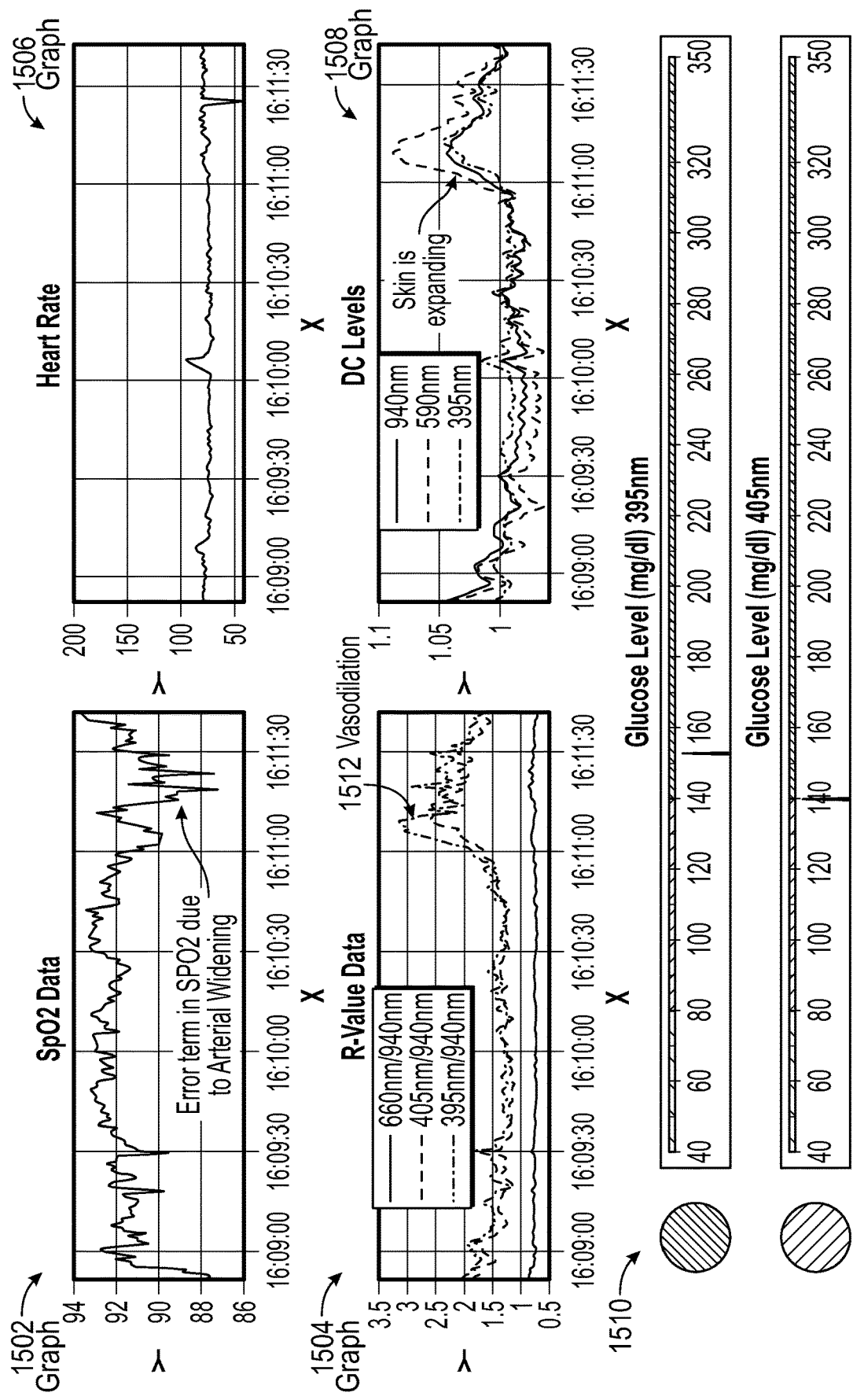
FIG. 15 illustrates a schematic diagram of a series of graphs illustrating the effects of vasodilation in PPG signals.

FIG. 15 illustrates a schematic diagram of a series of graphs illustrating the effects of vasodilation using the PPG signals shown in FIG. 14. The first graph 1502 illustrates R660/940 values that may be used to obtain a measurement of oxygen saturation SpO2. The vasodilation period 1512, seen at approximately 16.11.04 secs through approximately 16.11.17 secs, affects the R values and thus the SpO2 measurements. Other measurements based on R values or relative amplitudes of PPG signals are also affected by vasodilation. In an embodiment, an error value or calibration may be determined for measurements of oxygen saturation $SpO_2$ during a period of vasodilation. The error value or calibration may depend on the level of vasodilation or change in R values due to the vasodilation.

The second graph 1504 illustrates R values at R660/940, R405/940 and R395/940. The vasodilation period 1512, seen at approximately 16.11.04 secs through approximately 16.11.17 secs, affects the R values, especially R values using PPG signals in the UV or near UV range. The R values may be affected during the vasodilation period since the ratio of the amplitude of different wavelengths is used to obtain the R values. This may cause errors in the measurement of blood component levels. The R values and/or measurements of blood component levels may be compensated due to the effect of vasodilation to correct errors during periods of vasodilation.

For example, during the expansion of vessels during a vasodilation period (e.g., due to NO or other EDRF), it may not be practical to measure the $SpO_2$ amounts due to the error term present in the 940 & 660 nm PPG signals. This effect of vasodilation is likely being observed by current $SpO_2$ meters. Errors in the measurement of $SpO_2$ may be caused by undetected periods of vasodilation in current $SpO_2$ meters. Vasodilation may also cause errors in determinations of other blood components using PPG signals. The measurement of the respiratory cycle in a PPG signal is also affected during vasodilation.

The duration of the vasodilation effect may depend on the individual, the amount of the food ingested and the arterial rigidity. For example, the vessels of diabetic subjects are likely to expand less and have much less change in amplitude of PPG signals during vasodilation due to inelasticity of the arteries due to arterial rigidity and endothelial dysfunction.

The graph 1506 illustrates the higher frequencies of the PPG signal at 660 nm that may be used to measure the heart rate remains relatively unaffected during the period of vasodilation.

The graph 1508 illustrates the lower frequencies of PPG signals at 940 nm, 590 nm and 395 nm (e.g., the frequencies not affected by pulsatile blood flow). The characteristics of the lower frequencies of the PPG signals change during the vasodilation period. The absorption properties of the vascular tissue vary due to changes in volume of blood. In addition, the widening of the vessels compresses the surrounding tissue. And the epidermis, the upper layer of the skin, may expand in response to the widening vessels during vasodilation. The PPG signals are thus affected by this change in absorption properties of the tissue, as seen in graph 1508.

The graph 1508 also illustrates that the PPG signals in different spectrums exhibit a time or phase delay. For example, the PPG signal at 940 nm in the IR range, the PPG signal at 590 nm in the visible range, and the PPG signal at 395 nm in the UV range have timing differences. This time delay is due in part to the different penetration depths of the wavelengths. Preferably, to determine this time delay, PPG signals in an infrared range (IR) range from 650 nm to 1350 nm and PPG signals outside the IR range are compared to determine the time or phase delay.

The graph 1510 illustrates an elevated glucose level during the vasodilation period of about 140-152 mg/dl. At "rest", a body responds to caloric intake and vasodilation occurs normally as the body processes food, insulin is dispensed, and arteries expand due to Nitric Oxide (NO) causing the outer muscle of the arteries to expand temporarily. This caloric intake also elevates the glucose level temporarily. As shown in the graphs, the $SpO_2$ measurement is affected during the vasodilation period.

Vasodilation or vasoconstriction may also change the color or hue of the skin tissue due to expansion or contraction of the vessels. This increase or decrease of blood flow may change the hue of the skin. By monitoring the hue of the skin, the biosensor 100 may detect vasodilation or other changes in blood circulation in the tissue. For example, a PPG signal in a visible light range such as at a yellow (590 nm-560 nm) or Red (564 nm-580 nm) or Blue (490 nm-450 nm) wavelength may be used to detect a change in hue of the skin.

Furthermore, the PPG signals in different spectrums exhibit phase differences or timing differences that correspond to the expansion and constriction of the arteries during vasodilation or vasoconstriction. The phase differences are due in part to the different penetration depths of the wavelengths. At a same input power, light at higher wavelengths (IR light) penetrates vascular tissue deeper than light at lower wavelengths (UV light). The optical properties of the tissue are affected by many factors, including but not limited to, skin-tone, tissue hydration, and tissue chemistry. In a sensor configuration where the light from the light source is backscattered to a sensor on the same surface, the optical signal at the sensor includes a sum of all light backscattered that makes it to the focal surface after interacting with the tissue. With the optical power being the same across all wavelengths, some of the light backscattered from the IR light penetrates deeper into the tissue than the UV light does. This means that the different wavelengths of light probe different depths of tissue.

When the heart beats, the arteries swell as fluid is pushed out of the heart. The leading edge of the swelling or pressure wave moves like a "bulge" through the arterial system. This system can be thought of as an elastically dampened hydraulic system. The pressure wave or bulge in the pulsatile blood flow moves from the lower tissue to the upper tissue. Thus, the deeper penetrating wavelengths (such as IR light) detect a pressure wave first followed by the lesser penetrating wavelengths (such as visible then UV light). The time delay in the "bulge" or pressure wave moving from the lower tissue into the upper tissue thus creates a time delay in a pressure waveform seen in the PPG signals at different wavelengths. For example, as seen in FIG. 15, a waveform in the UV range has a time delay compared to a waveform in the IR range and a waveform in the visible range (390 nm to 700 nm). This time delay in the different wavelengths is thus due to the depth of penetration into the skin of each wavelength.

Vasodilation changes the propagation of the pressure wave starting in the deeper, larger arteries and then moving to the shallower, smaller ones. In an embodiment described herein, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in shape and time delay of PPG signals of two or more wavelengths with different penetration depths (e.g., wherein at least one is in the near-IR window and one is not), information about vasodilation may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined include, but are not limited to, the time delay between the systolic points and diastolic points in different wavelengths and the difference in dicrotic notch suppression between wavelengths.

Figure 16:
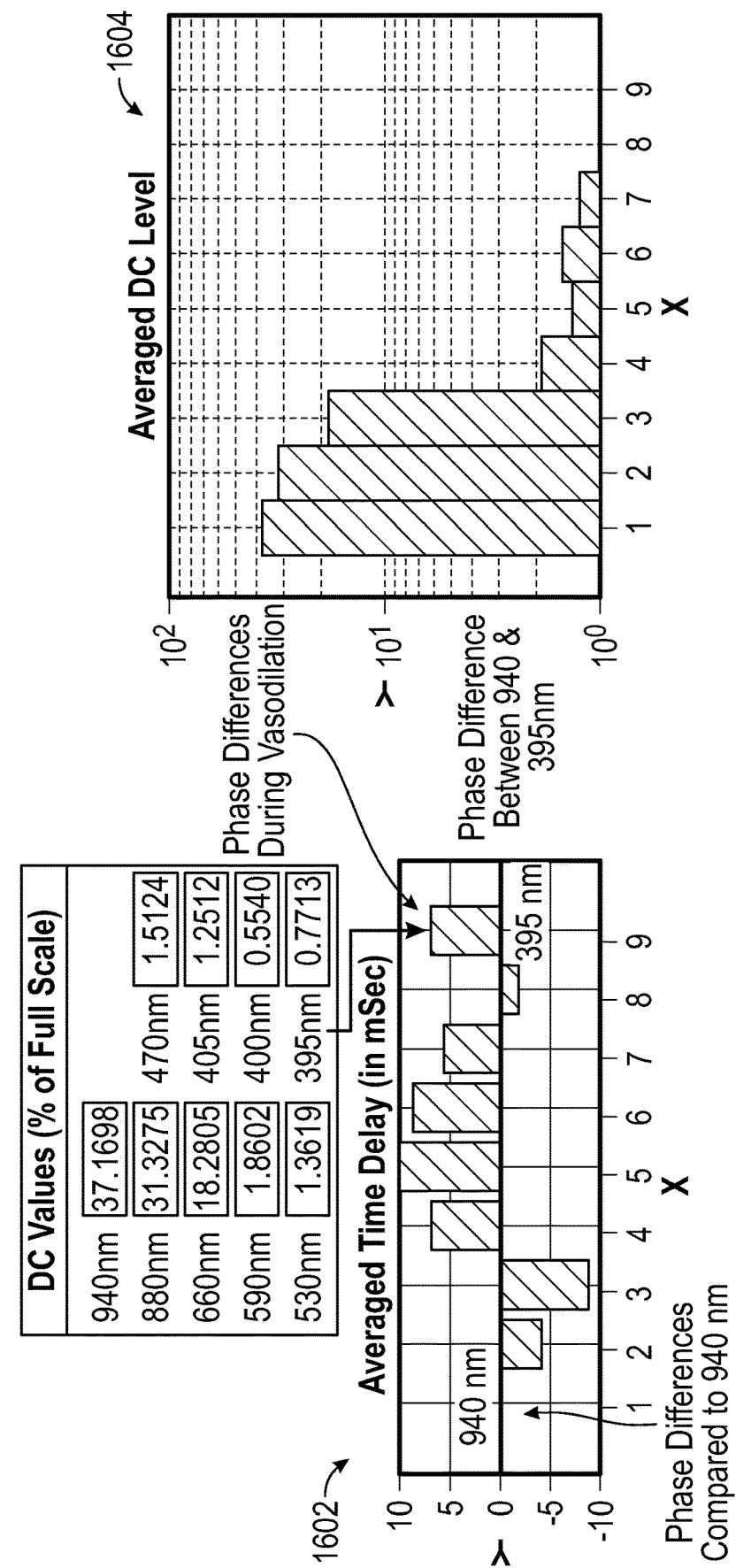
FIG. 16 illustrates a schematic diagram illustrating phase differences and average low frequency levels during vasodilation of PPG signals of various wavelengths.

FIG. 16 illustrates a schematic diagram 1600 illustrating phase differences and average low frequency levels during vasodilation using the PPG signals of various wavelengths from FIG. 14. The Graph 1602 illustrates the average phase difference between a PPG signal at 940 nm and PPG signals of various wavelengths during the period of vasodilation. The first time difference is 0 between 940 and itself. The last shown time difference is between 395 nm and 940 nm. The phase difference or the timing difference between PPG signals in graph 1602 illustrates a negative to positive timing which corresponds to the constrictions and expansion of the arteries during vasodilation. The phase delay between the PPG signals at different wavelengths is thus seen during a period of vasodilation.

The second graph 1604 illustrates the average "DC values" in PPG signals of various wavelengths during the period of vasodilation. The "DC values" include DC components and/or low frequency components not generally affected by the pulsatile blood flow. The graph 1604 illustrates that the average DC values $I_{DC}$ are above a baseline normal during the period of vasodilation. The average DC values increase due to vasodilation, tissue characteristics of contracting or expanding muscles and is proportional to the force applied to the muscle. So, the DC value (low frequencies not generally affected by the pulsatile blood flow) can be used to determine a force applied during the movement.

Figure 17:
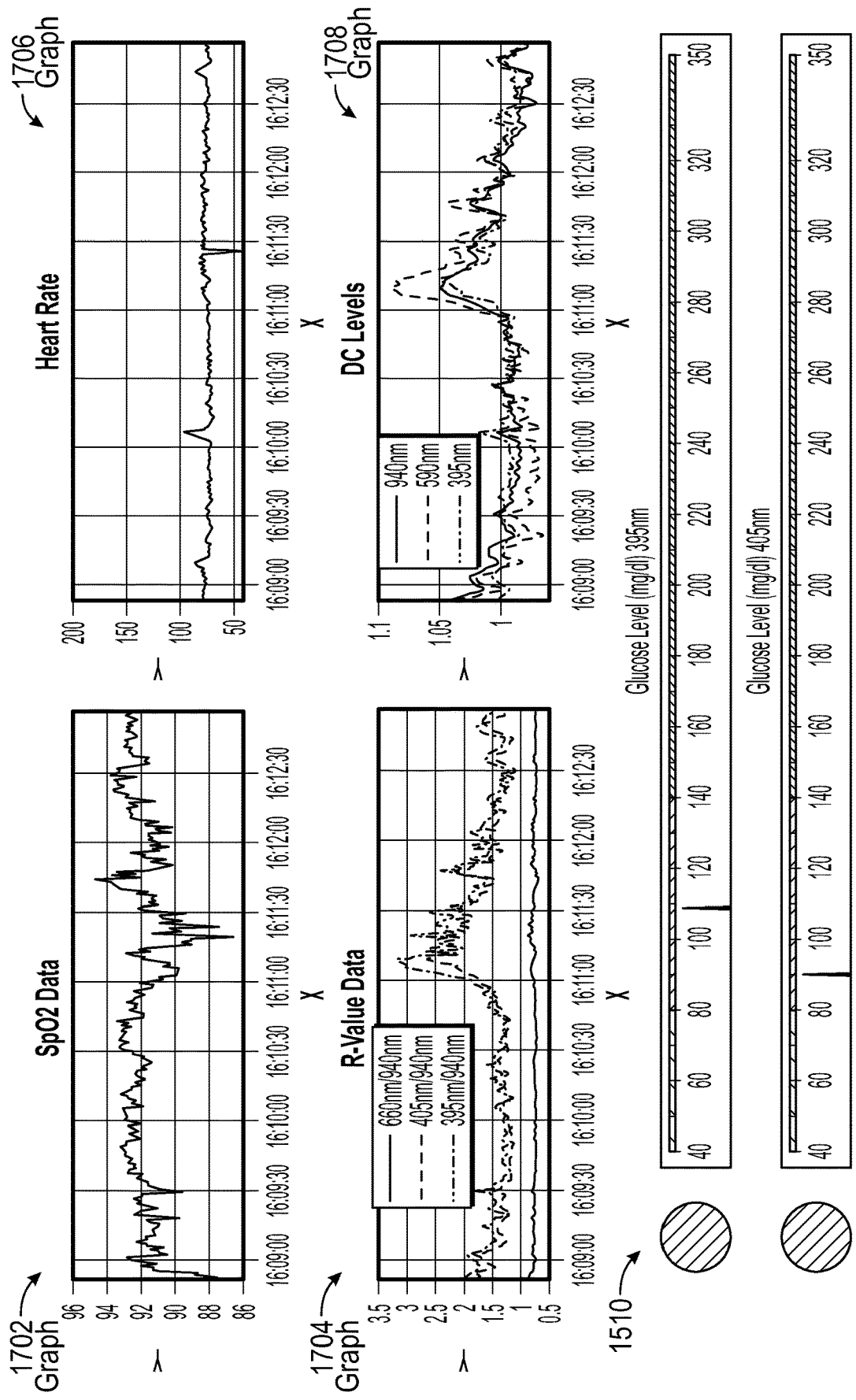
FIG. 17 illustrates a schematic diagram of a series of graphs illustrating a period after vasodilation using the PPG signals.

FIG. 17 illustrates a schematic diagram of a series of graphs illustrating a period after vasodilation using the PPG signals shown in FIG. 14. Graph 1702 illustrates $R_{660/940}$ values obtained over a period of roughly four minutes. As described with respect to FIG. 14, the subject ingested a high caloric substance to induce NO production due to insulin dispensing and glucose regulation thru the arteries and veins. As shown in the graphs, the PPG signals reflect vasodilation of vessels due to the NO production during a vasodilation period. The vasodilation period in PPG signals is seen in the graphs at approximately 16.11.04 through approximately 16.11.17. As seen in graph 1702, the $R_{660/940}$ values return to baseline after the vasodilation period. In addition, the R values at $R_{660/940}$, $R_{405/940}$ and $R_{395/940}$ in Graph 1704 also return to baseline values after the vasodilation period.

The "DC levels" or levels of the lower frequencies in the PPG signals in graph 1708 also returns to baseline values after the vasodilation period. The glucose levels shown in graph 1710 also return to baseline values between 90-110 mg/dl after the vasodilation period. The graph 1706 illustrates the higher frequencies of the PPG signal at 660 nm that may be used to measure the heart rate remains relatively unaffected during the period of vasodilation.

Figure 18:
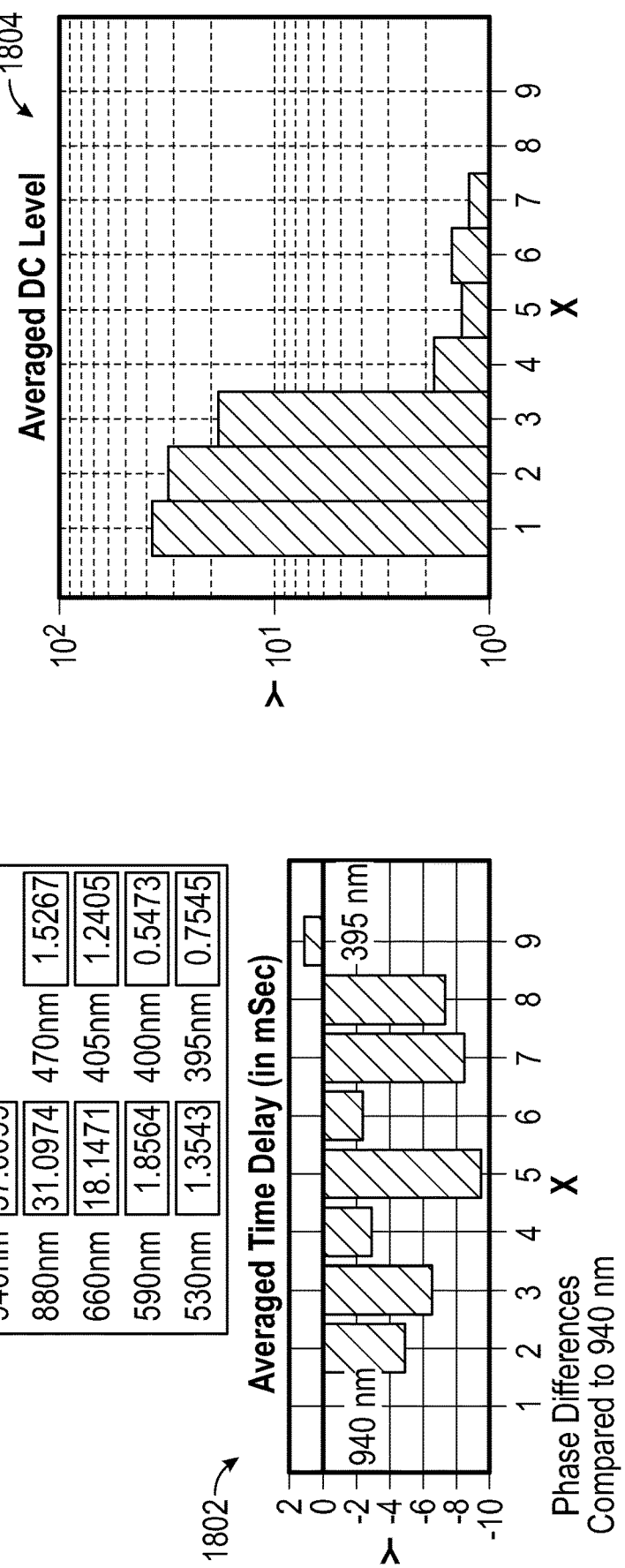
FIG. 18 illustrates a schematic diagram illustrating phase differences and average low frequency levels after the period of vasodilation of the PPG signals of various wavelengths.

FIG. 18 illustrates a schematic diagram 1800 illustrating phase differences and average low frequency levels after the period of vasodilation using the PPG signals of various wavelengths from FIG. 14. The Graph 1802 illustrates the average time or phase difference between a PPG signal at 940 nm and PPG signals of various wavelengths during the period of vasodilation. The phase difference is measured with respect to the PPG signal at 940 nm and so the phase delay shown is zero for 940 nm. The last shown time difference is between 395 nm and 940 nm. This graph 1506 illustrates that the baseline time differences return after the period of vasodilation. The change in phase differences between two or more different wavelengths may thus be used to determine a level of vasodilation and/or the period of vasodilation.

The second graph 1804 illustrates the average DC values $I_{DC}$ of PPG signals of various wavelengths after the period of vasodilation. The DC values $I_{DC}$ may include low frequencies not generally affected by the pulsatile blood flow. The graph 1804 illustrates that the average DC values $I_{DC}$ return to a baseline normal after the period of vasodilation. The change in $I_{DC}$ in one or more different wavelengths may thus be used to determine a level of vasodilation and/or the period of vasodilation.

Figure 19:
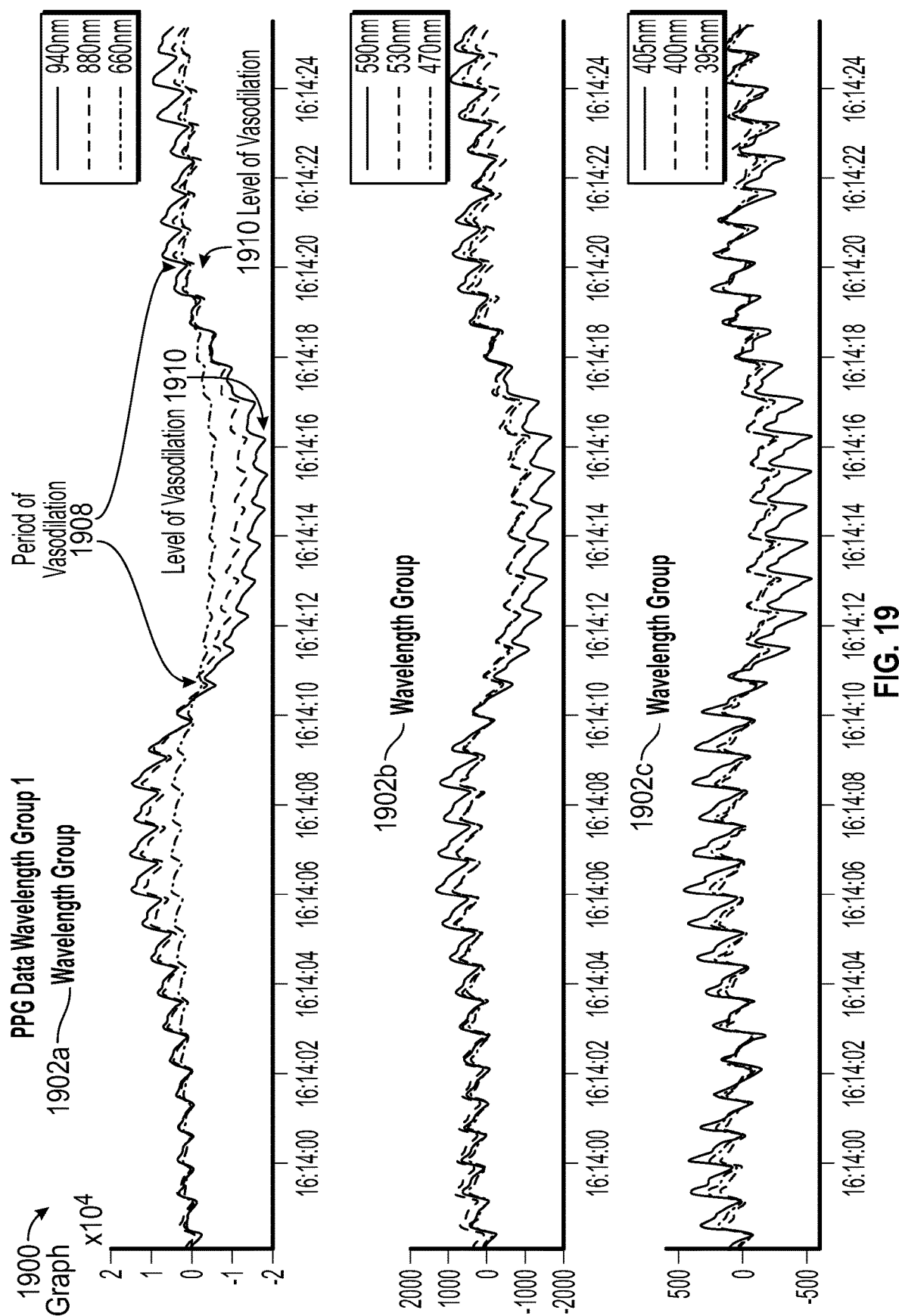
FIG. 19 illustrates a schematic diagram of a graph of PPG signals obtained during another period of vasodilation.

FIG. 19 illustrates a schematic diagram of a graph of PPG signals obtained during another period of vasodilation. The biosensor 100 obtained a PPG signal during vasodilation after caloric intake around a wavelength at 940 nm, a wavelength at 880 nm and a wavelength at 660 nm as shown in the PPG Signals for Wavelength Group 1902a. The biosensor 100 also obtained the spectral response for a wavelength at 590 nm, a wavelength at 530 nm and a wavelength at 470 nm as shown in the PPG Signals for Wavelength Group 1902b. The biosensor 100 further obtained the spectral response for a wavelength at 405 nm, a wavelength at 400 nm and a wavelength at 395 nm as shown in the PPG Signals for Wavelength Group 1902c.

The PPG signals are obtained after an approximate three minute period from the PPG signals shown in FIG. 14. A second period of vasodilation 1908 (e.g., possibly due to Phase II of digestion) is observed from approximately 16.14.11 sec to 16.14.20 sec in the PPG signals. A change in amplitude at low frequency of the PPG signals reflects the level of vasodilation 1910.

Figure 20:
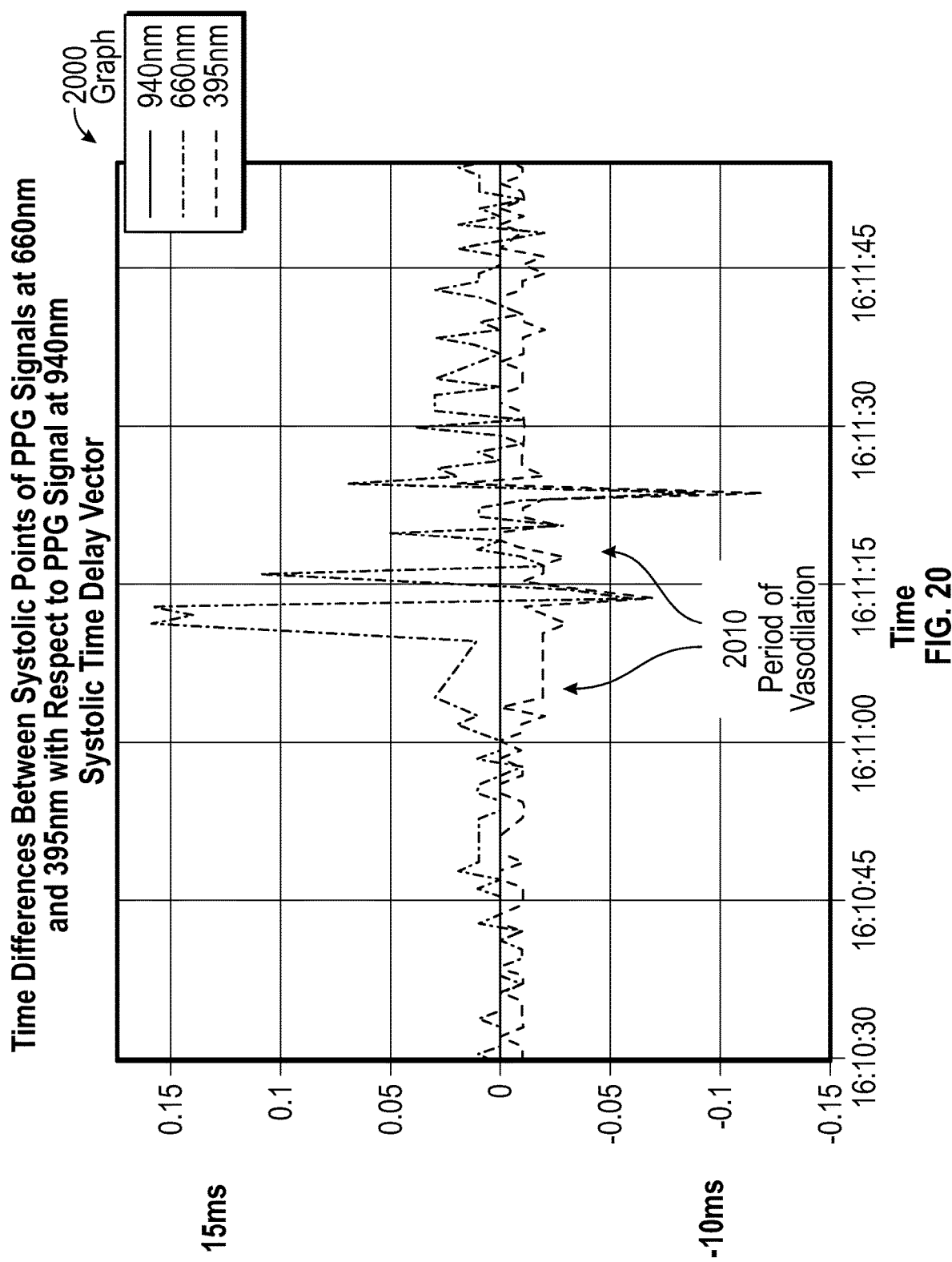
FIG. 20 illustrates a schematic diagram of a graph illustrating timing differences between systolic points of PPG signals at different wavelengths during a period of vasodilation.

FIG. 20 illustrates a schematic diagram of a graph 2000 illustrating timing differences between systolic points of PPG signals at different wavelengths (660 nm and 395 nm) with respect to 940 nm during a period of vasodilation. The first vasodilation period 2010 is seen in the graph at approximately 16.11.04 through approximately 16.11.17 when the time difference changes between the systolic points on the PPG signals at different wavelengths.

Figure 21:
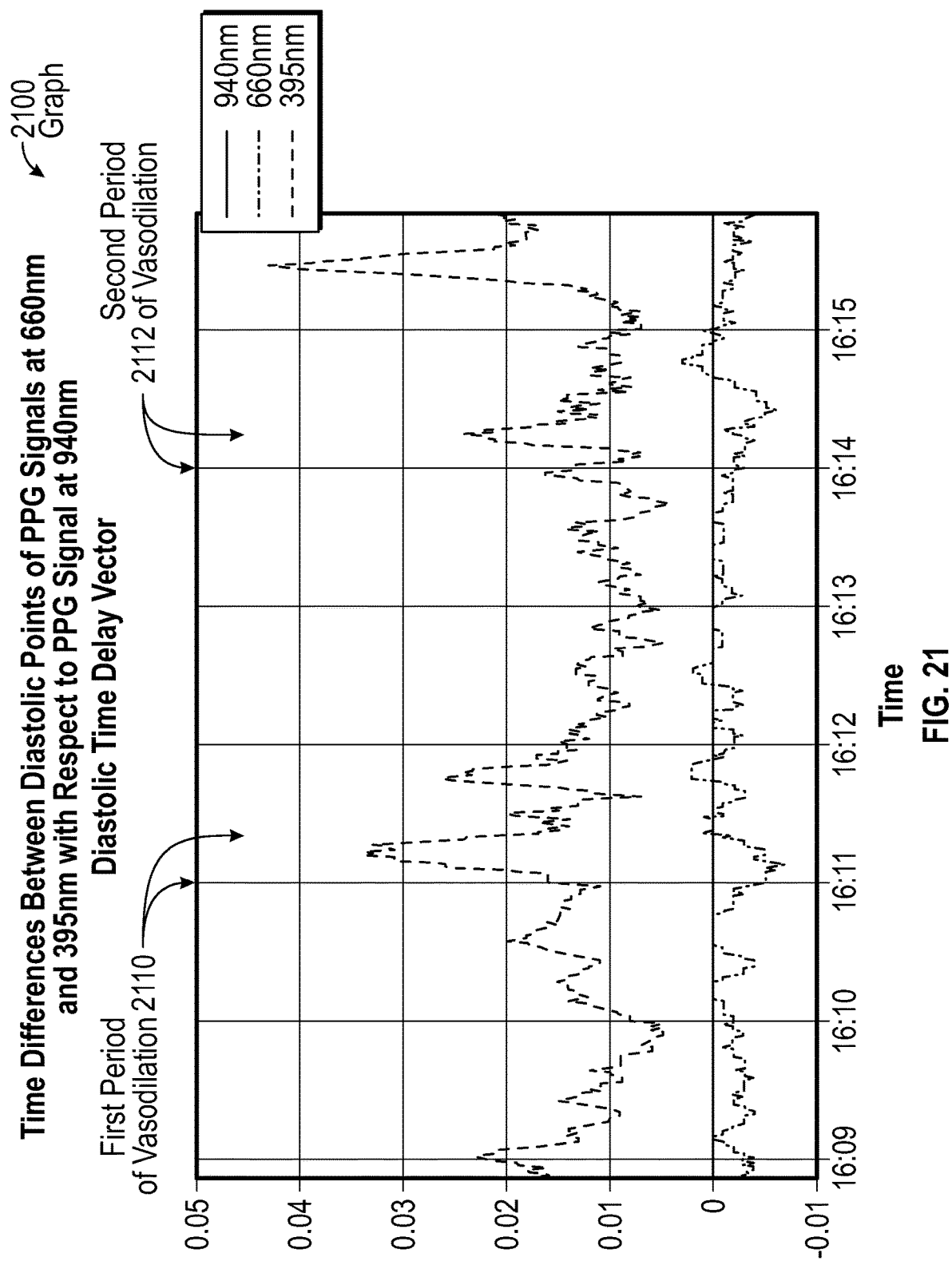
FIG. 21 illustrates a schematic diagram of a graph illustrating timing differences between diastolic points of PPG signals at different wavelengths during periods of vasodilation.

FIG. 21 illustrates a schematic diagram of a graph 2100 illustrating timing differences between diastolic points of PPG signals at different wavelengths (660 nm and 395 nm) with respect to 940 nm during periods of vasodilation. The first period of vasodilation 2110 is detected using the PPG signals at approximately 16.11.04 through approximately 16.11.17 when the time difference between the wavelengths change. A second period of vasodilation 2112 is detected using the PPG signals at approximately 16.14.00 to 16.14.24 when the time difference between the wavelengths again changes. The time difference between the PPG signals at the different wavelengths may thus be used to determine a level of vasodilation and/or a period of vasodilation.

Figure 22:
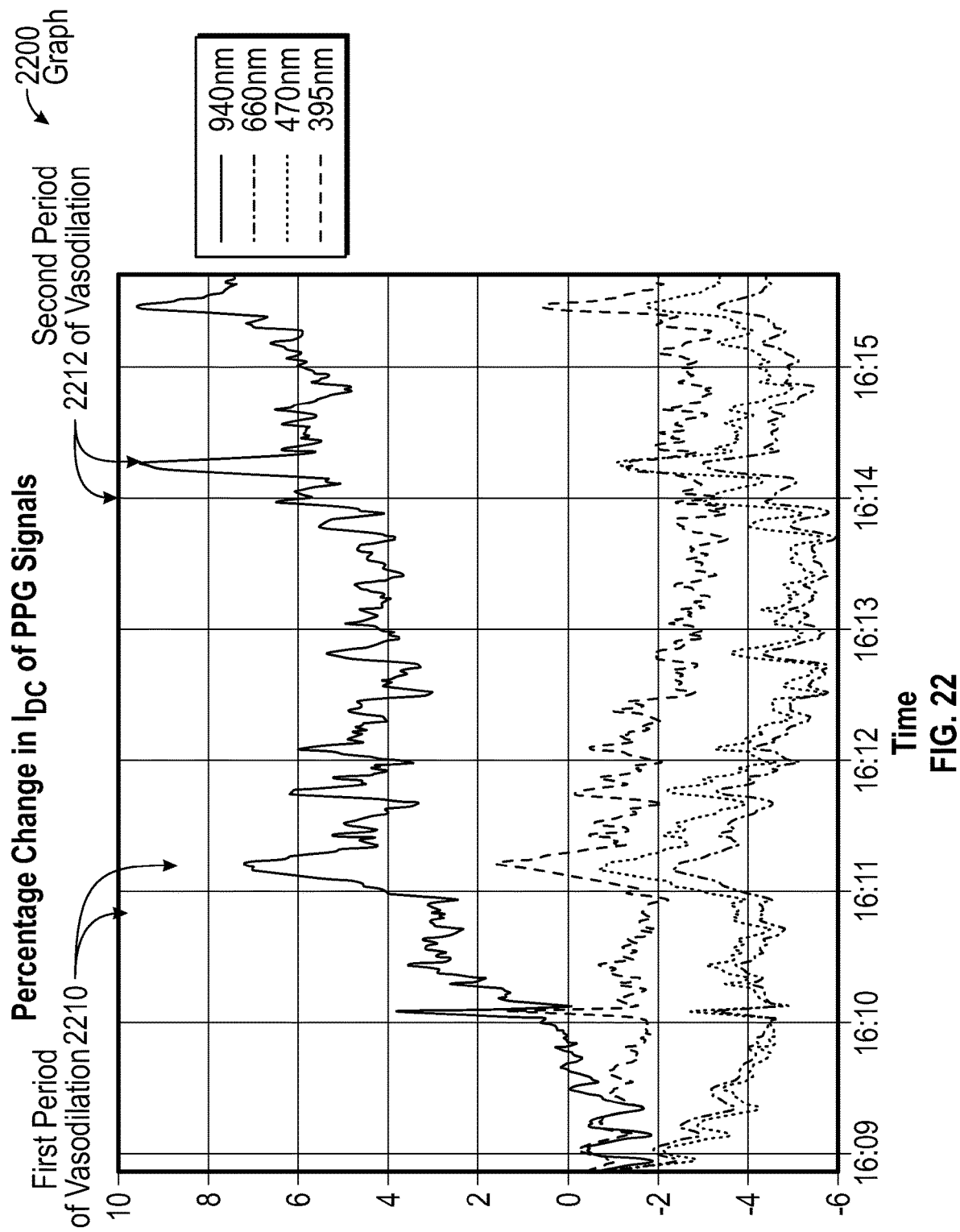
FIG. 22 illustrates a schematic diagram of a graph illustrating a percentage change in component levels $I_{DC}$ of PPG signals at different wavelengths during a period of vasodilation.

FIG. 22 illustrates a schematic diagram of a graph 2200 illustrating a percentage change in component levels $I_{DC}$ of PPG signals at different wavelengths (940 nm, 660 nm, 470 and 395 nm) during the vasodilation period. The component level $I_{DC}$ includes DC and lower frequencies of the PPG signal not affected by pulsatile blood flow. The first period of vasodilation 2210 is detected using the PPG signals at approximately 16.11.04 through approximately 16.11.17 when the percentage change in component levels $I_{DC}$ increases in the PPG signals. A second period of vasodilation 2212 is detected at approximately 16.14.00 secs to 16.14.24 secs when the percentage change in component levels $I_{DC}$ increases again in the PPG signals. The change in $I_{DC}$ in one or more different wavelengths may be used to determine a level of vasodilation and/or the period of vasodilation.

Figure 23:
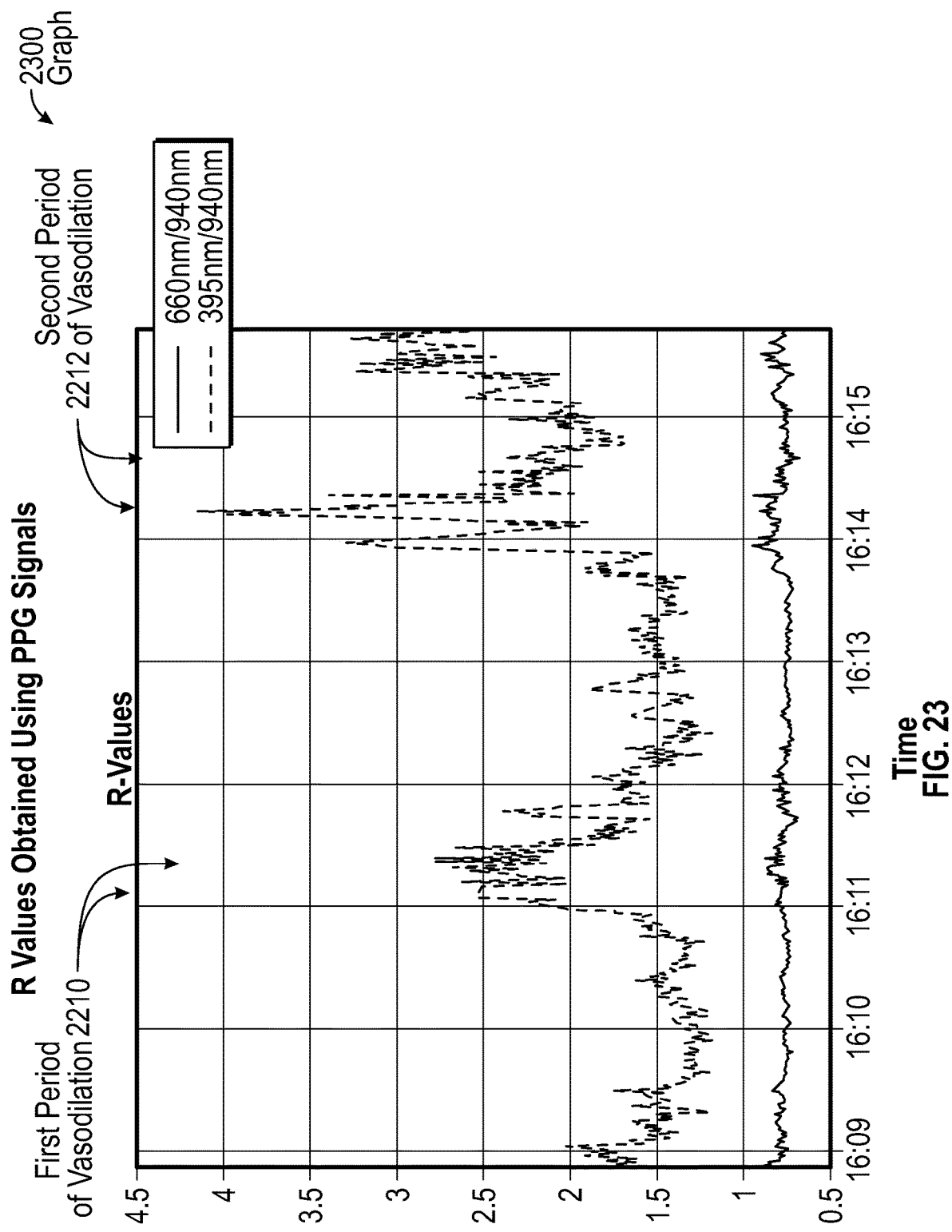
FIG. 23 illustrates a schematic diagram of a graph illustrating changes in R values during a period of vasodilation.

FIG. 23 illustrates a schematic diagram of a graph 2300 illustrating changes in R values during periods of vasodilation. The R values of 660 nm/940 nm and 395 nm/940 nm are illustrated. The R values may be affected during the vasodilation periods since the ratio of the amplitude of different wavelengths is used to obtain the R values. The first period of vasodilation 2310 is detected using the PPG signals at approximately 16.11.04 through approximately 16.11.17 using a change in R values. A second period of vasodilation 2212 is detected at approximately 16.14.00 secs to 16.14.24 secs using another change in R values. The change in R values may thus be used to determine a level of vasodilation and/or the period of vasodilation.

Figure 24:
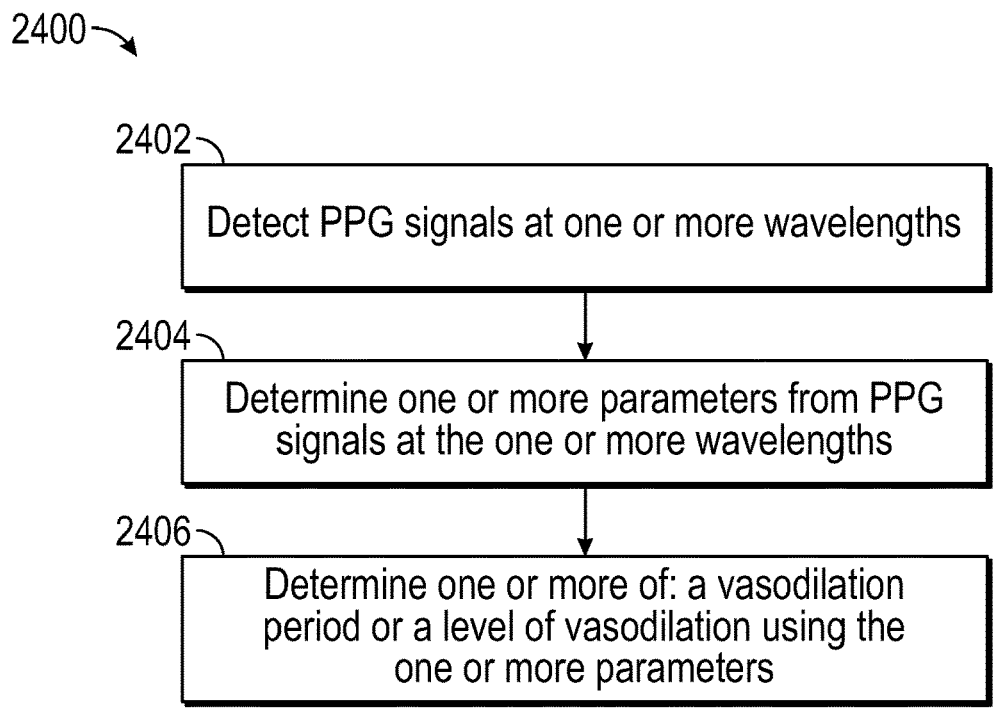
FIG. 24 illustrates a logical flow diagram of a method for determining a level of vasodilation and/or a period of vasodilation using PPG signals at one or more wavelengths.

FIG. 24 illustrates a logical flow diagram of a method 2400 for determining a level of vasodilation and/or a period of vasodilation using PPG signals at one or more wavelengths. The PPG signals reflected from skin tissue of a user are detected at one or more wavelengths at 2402. In an embodiment, the PPG signals are detected at a first wavelength and at second wavelength, wherein the first wavelength penetrates the skin tissue of the patient at a greater depth than the second wavelength. For example, the first wavelength is in an IR range and the second wavelength is in a visible range or UV range.

One or more parameters are derived using the PPG signals at 2404, and a level of vasodilation or a vasodilation period are determined using the one or more parameters at 2406. For example, in one aspect, a phase difference between the PPG signals at the first wavelength and the second wavelength are determined. Systolic points, diastolic points or other portions of the waveforms may be used to determine the phase difference between the PPG signals at the different wavelengths. A level of vasodilation and a period of vasodilation may be determined using the phase differences between the PPG signals at the different wavelengths. For example, a calibration table or function may correlate the phase difference to a level of vasodilation.

In another aspect, low frequency and/or DC components in the PPG signals at one or more wavelengths are determined, wherein the low frequency or DC components are not affected by pulsatile blood flow due to a cardiac cycle. The level of vasodilation or period of vasodilation may be determined using the change in amplitude of the low frequency components. For example, low frequency or DC levels of the PPG signals increase when arteries widen during a period of vasodilation. The increased arterial width during vasodilation affects blood volume and amplitude of the DC or low frequency components of the PPG signals. The underlying tissue characteristics affect whether PPG signals in a UV or IR range results in a better measurement.

In another aspect, R values are determined using the PPG signals at least two wavelengths, such as $R_{660\ nm/940\ nm}$ or $R_{405/940}$ or $R_{395\ nm/940\ nm}$. The level of vasodilation or period of vasodilation may be determined using changes in amplitude of one or more R values.

In another aspect, a change in hue of the bulk tissue, in the field of the sensor, is determined using the PPG signals. For example, PPG signals at one or more wavelengths with a high optical absorption coefficient for a skin hue may be used to detect vasodilation or circulation. The color or hue of the tissue may change due to expanding or contracting vessels during vasodilation or changes in circulation that change a hue of the tissue. By monitoring the hue of the skin, the biosensor 100 may detect vasodilation or other changes in blood circulation in the tissue. For example, a PPG signal in a visible light range such as at a yellow (590 nm-560 nm) or Red (564 nm-580 nm) or Blue (490 nm-450 nm) wavelength may be used to detect a change in hue of the skin. The PPG signals may thus be used to detect change in color of the tissue due to one or more of: an increase or decrease of blood circulation in the skin tissue, or a movement of bulk tissue due to widening of vessels. The level of vasodilation or period of vasodilation may be determined using changes in hue of the tissue.

The described parameters are exemplary and other parameters may be derived using the PPG signals at one or more wavelengths to determine a level of vasodilation and/or a period of vasodilation. A calibration table or function may store a mapping of one or more of the parameters to a level of vasodilation. The level of vasodilation may be represented as a measurement of one or more of: a percentage of change in arterial width, diameter or planar area or a change in blood flow or volume, etc. The above described parameters of the PPG signals may also be used to determine a level of vasoconstriction and a period of vasoconstriction using similar methods. In general, when used herein, a level of vasodilation includes a level of vasoconstriction as well.

Embodiment—Compensation of Measurement Levels During Vasodilation

Figure 25:
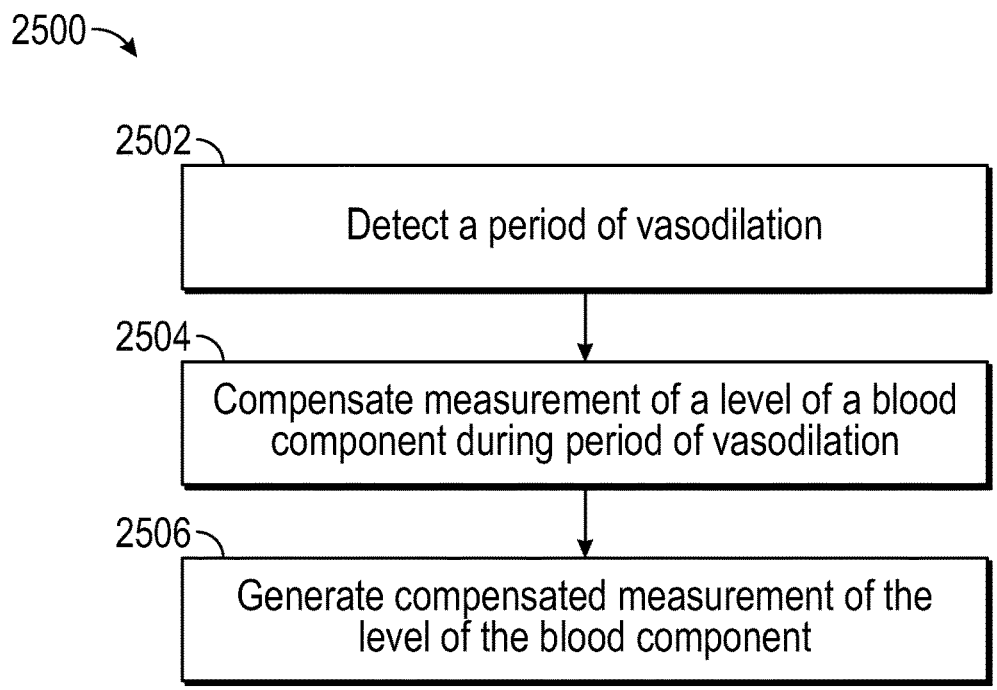
FIG. 25 illustrates a logical flow diagram of a method for compensating a level of a blood component during vasodilation.

FIG. 25 illustrates a logical flow diagram of a method 2500 for compensating a level of a blood component during vasodilation. The intensity levels of PPG signals are affected during these periods of vasodilation. This change in intensity levels of PPG signals during periods of vasodilation may create inaccurate measurements of blood component levels, such as $SpO_2$ and NO levels, obtained using these PPG signals.

A period of vasodilation is detected at 2502. The measurement of a level of a blood component is then compensated during the period of vasodilation using one or more methods at 2504. In a first method, a compensation factor is determined based on a level of vasodilation. One or more of the measurements or variables at one or more of the wavelengths is adjusted using the compensation factor. For example, an L value determined using a PPG signal at an IR wavelength may be adjusted during a period of vasodilation. In another example, an R value determined using a UV wavelength and IR wavelength may be adjusted during a period of vasodilation.

In another method, the blood component levels may be calibrated to compensate for the effect of vasodilation to correct errors in the measurements during periods of vasodilation.

The calibration of the values may be stored in a calibration table. The calibration may depend on the level of the vasodilation and the characteristics of the underlying bulk tissue. The calibration may be determined using a general sample population with measurements of the blood components measured using other methods during periods of vasodilation.

The compensated measurement of the level of the blood component is then generated at 2506 and may be displayed. Alternatively, during a period of vasodilation, an error may be returned. The measurement of the blood component may then be determined after the end of vasodilation.

Embodiment—Measurement of Arterial Stiffness

Arterial stiffness and pulse pressure have been proposed as a predictor of cardiovascular disease. Multiple cardiovascular risk factors (increased BMI, hypertension, MAP, diabetes mellitus, and smoking) have been associated with arterial stiffness and pulse pressure. In a known method, an arterial stiffness index (ASI) measures arterial stiffness by using a single PPG signal to record the volume waveform of the blood, e.g. in the finger. The shape of the waveform has been shown as directly related to the time it takes for the pulse wave to travel through the arterial tree in the lower body, and to be reflected back to the finger. The time between peaks of the waveform (the peak-to-peak time) is divided into the person's height to obtain an Arterial Stiffness Index (SI). An improved method and system for determining arterial stiffness is needed.

Figure 26:
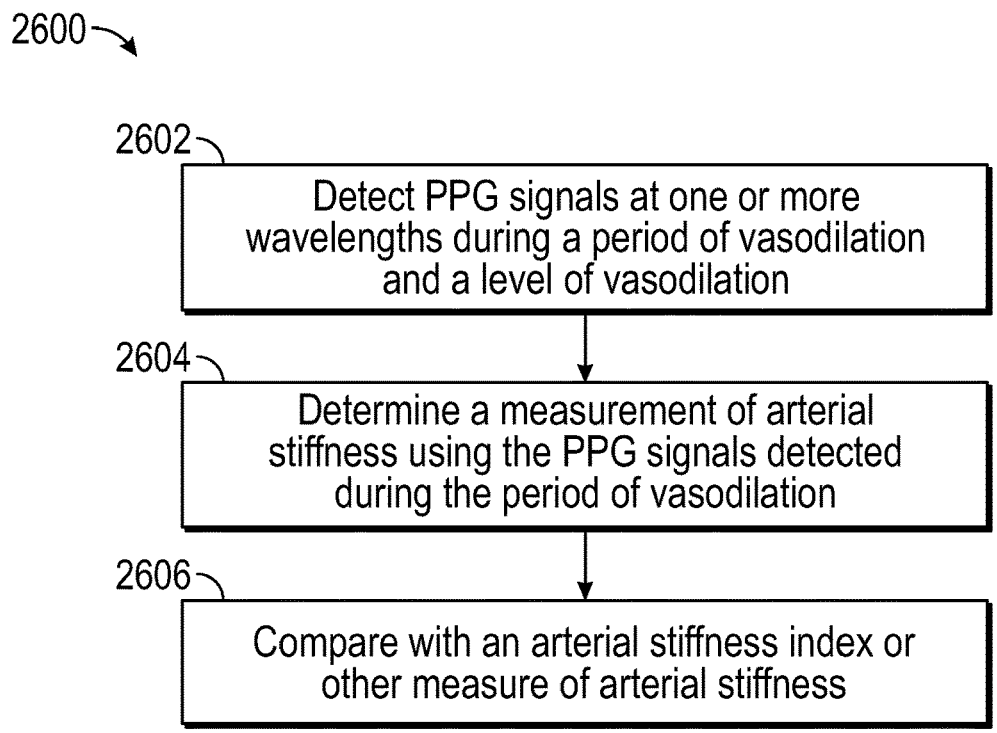
FIG. 26 illustrates a logical flow diagram of a method for determining a measurement of arterial stiffness using PPG signals detected during a period of vasodilation.

FIG. 26 illustrates a logical flow diagram of a method 2600 for determining a measurement of arterial stiffness using PPG signals detected during a period of vasodilation. PPG signals at one or more wavelengths are detected and a period of vasodilation is determined using the PPG signals at 2602. A level of vasodilation may also be determined from the PPG signals and/or a rate of change of the level of vasodilation. Arterial stiffness may decrease a relative level of vasodilation compared to an average or normal range. In addition, the rate of change of the width of the artery at a beginning or end of vasodilation may be used as an indicator of arterial stiffness. A reduction in elasticity of arteries may decrease the rate of change in the width of the artery and thus the rate of change in the level of vasodilation. One or more of these parameters may be determined using multiple PPG signals, which penetrate the tissue at different depths, detected during the period of vasodilation and used to determine a measurement of arterial stiffness at 2604.

The measurement of the arterial stiffness may be compared to the arterial stiffness index or to other measures of arterial stiffness at 2606. The comparison may be performed for verification. Alternatively, the different measurements may be averaged or added or otherwise used to determine a final arterial stiffness.

Overall cardiovascular health may be assessed using the measurement of arterial stiffness as well as a measurement of pulse pressure. Multiple cardiovascular risk factors (increased BMI, hypertension, MAP, diabetes mellitus, and smoking) have been associated with arterial stiffness and pulse pressure. Circulatory problems may also be identified using PPG signals measured at one or more extremities and comparing with normal or average levels of pulse pressure.

Embodiment—Measurement of Stress Levels

Figure 27:
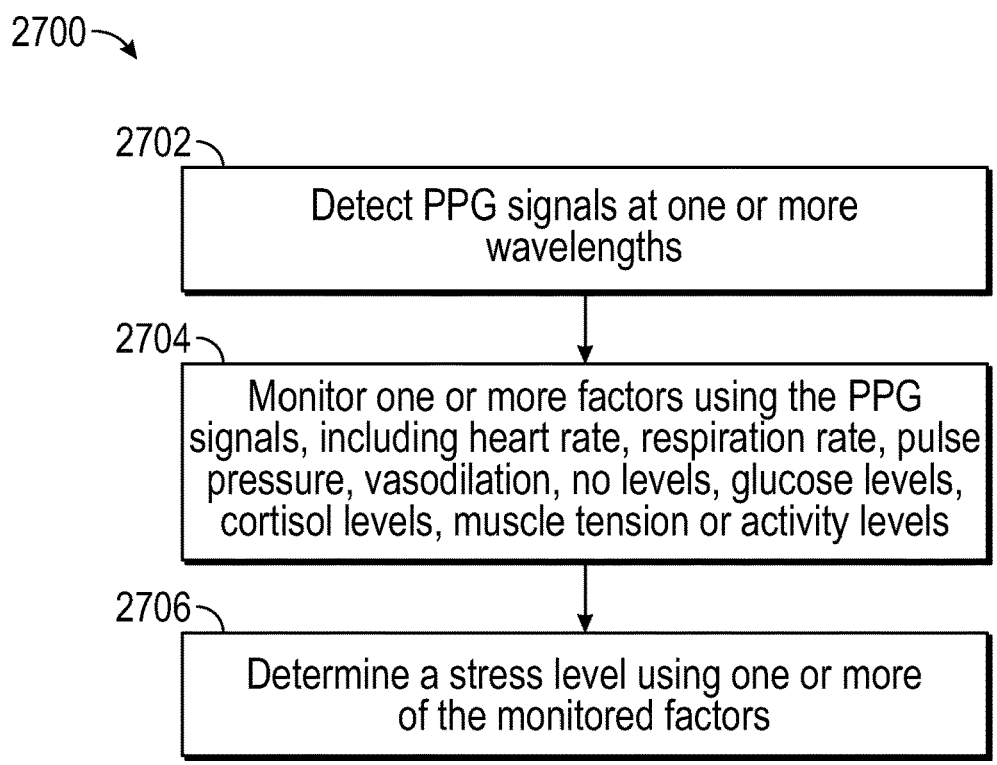
FIG. 27 illustrates a logical flow diagram of a method for determining a stress level using PPG signals.

FIG. 27 illustrates a logical flow diagram of a method 2700 for determining a stress level using PPG signals. PPG signals at one or more wavelengths are detected at 2702 and used to obtain measurements of and monitor one or more factors at 2704. The one or more factors are used to estimate a stress level of a user at 2706. The factors may include one or more of heart rate, respiration rate, pulse pressure, level of vasodilation, concentration of Nitric Oxide, cortisol levels, muscle tension or activity level. A combination of these factors may also be used to estimate a patient baseline health assessment as well as an overall stress level.

In a first aspect, a factor to monitor stress level includes muscle tension. Muscle movement causes an increase in blood flow in surrounding tissue. This increase in blood flow may be measured by an increase in the pulsatile blood flow or $I_{AC}$ component of the PPG signals. For example, the $I_{AC}$ component of PPG signals measured at a wrist of a patient increases when a fist is clenched or other surrounding muscles tense. The amplitude or intensity in the $I_{AC}$ component may be monitored as a factor to determine a muscle tension or stress level.

The heart rate and respiration rate may also increase during periods of stress. These vital signs may also be monitored by the biosensor 100 as factors to determine a stress level.

Another factor that may be monitored is vasodilation. Typically, the body releases cortisol during periods of stress. Cortisol is a steroid hormone that is produced by the adrenal glands. When released into the bloodstream, cortisol can act on many different parts of the body. Cortisol controls blood pressure, pulse pressure, glucose, metabolism, and other functions in response to stress levels. Cortisol also creates a vasodilation response. Thus, vasodilation, including a frequency of vasodilation periods and duration of the periods of vasodilation, may be monitored as another factor to determine a stress level.

In another aspect, the pulse pressure (e.g. measured by the amplitude of the $I_{AC}$ component of PPG signals) is another factor that may be monitored to determine a stress level. In general, pulse pressure increases during periods of stress, e.g. due to increase in cortisol.

A further factor that may be considered are measurements of glucose levels. An increase in cortisol levels during periods of stress affects glucose levels. For example, $R_{395/940}$ values are indicators of glucose levels and are affected by fluctuations in glucose levels, e.g. due to increases in cortisol. The $R_{395/940}$ values may be monitored to determine fluctuations in response to stress levels. The R values may be obtained using a first wavelength in a range of approximately 350-450 nm and a second wavelength with a low absorption coefficient for NO. In general, it has been observed that R values obtained in these ranges increase as well as exhibit increased signal to noise ratios and greater fluctuations during periods of high stress levels. Thus, R values may be monitored as another factor to determine a stress level.

Cortisol levels may also be monitored from the R values obtained using a first wavelength in a range of approximately 350-450 nm and a second wavelength with a low absorption coefficient for NO. When a period of increased stress is detected from one or more of the described factors, the fluctuations or increase in the R value may be assumed to be due to cortisol levels in the blood stream. Using a calibration table, the increase in R value (or increase in glucose level) during stress may be correlated to a cortisol level.

Embodiment—Detection of Infection

In an embodiment, the biosensor 100 detects an infection or potential infection using measurements of vasodilation. An infection in tissue, such as around a wound site, creates increased blood flow in the tissue due to vasodilation. The inflamed, swollen tissue exhibits an increase in vasodilation.

Figure 28A:
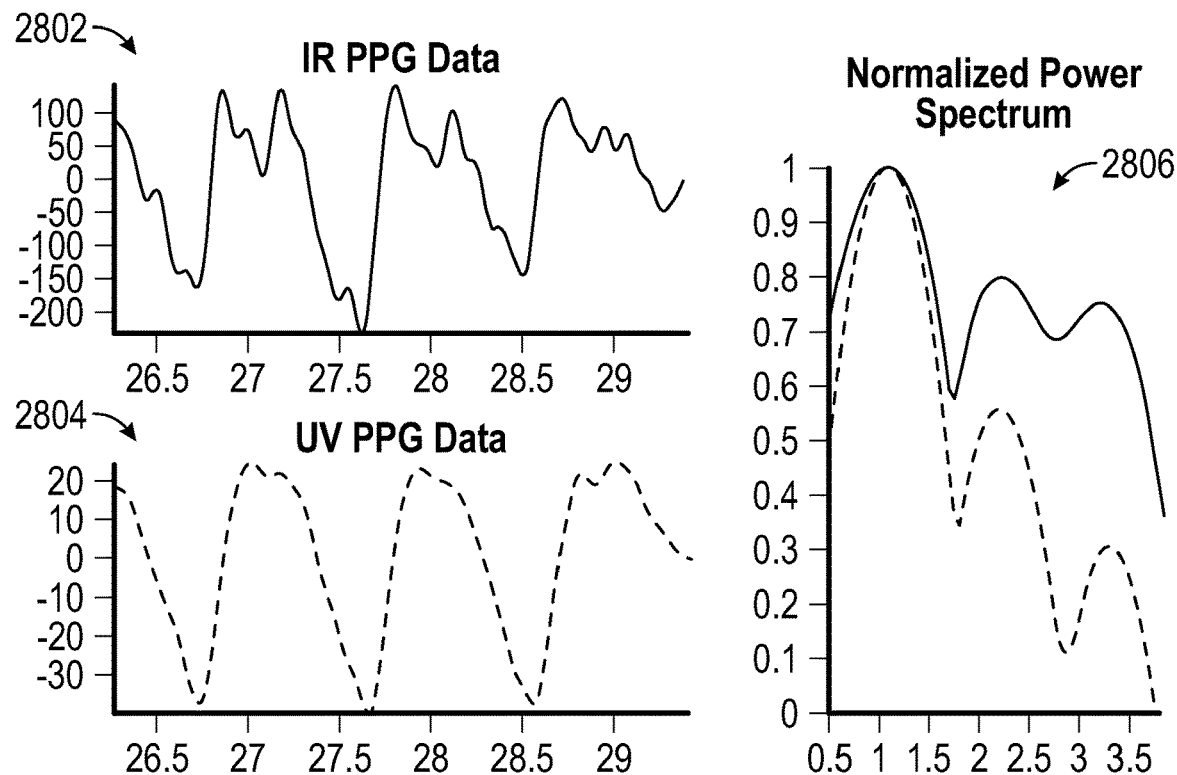
FIG. 28A illustrates a schematic diagram of graphs of PPG signals detected from normal tissue.

FIG. 28A illustrates a schematic diagram of graphs of PPG signals detected from normal tissue. In this embodiment, a biosensor 100 is positioned on a forearm over normal tissue. Graph 2802 illustrates a PPG signal at an IR wavelength, such as 880 nm or 940 nm. The Graph 2804 illustrates a PPG signal at a UV range, such as 395 nm or 405 nm. The PPG signals reflect the pulse pressure wave due to the cardiac cycle. Due to the increased penetration of the IR wavelength in the tissue, the PPG signal at the IR wavelength has a different pulse shape than the PPG signal at the UV wavelength. Graph 2806 illustrates a normalized power spectrum of the PPG signals at the UV and IR wavelengths. Due to the increased penetration and greater blood volume detected, the PPG signal at the IR wavelength has an increased normalized power spectrum.

Figure 28B:
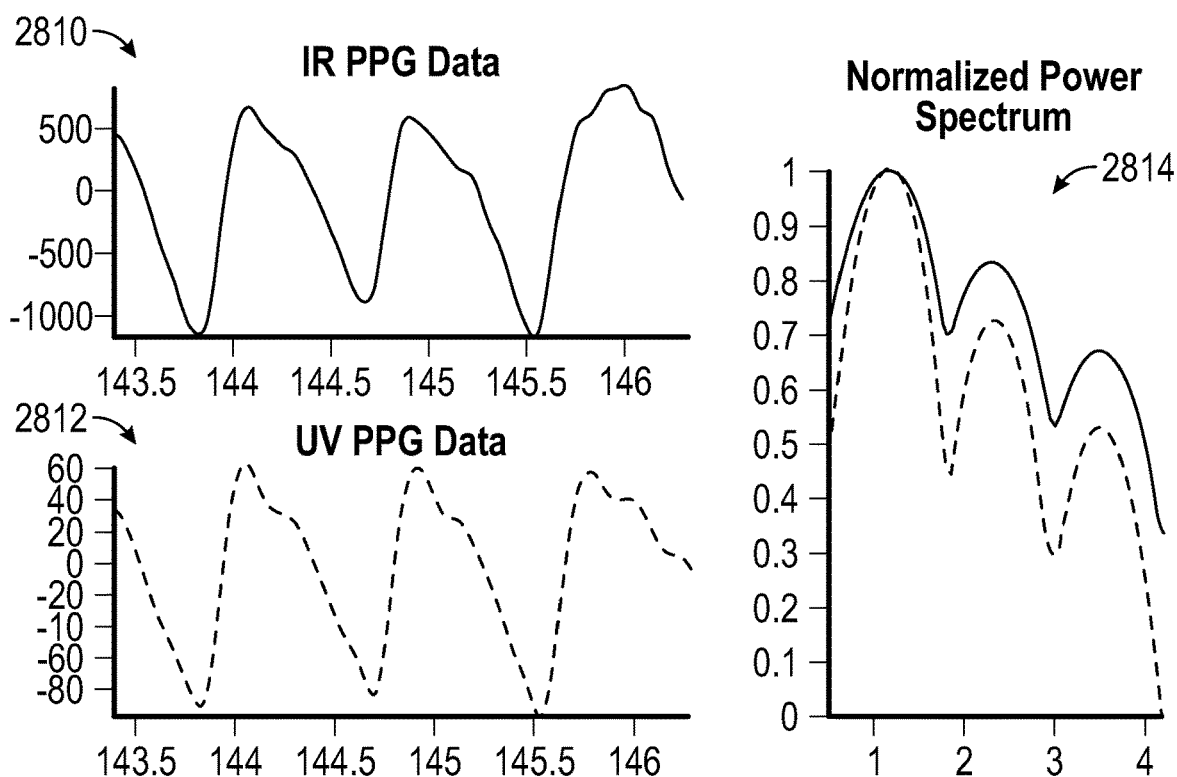
FIG. 28B illustrates a schematic diagram of graphs of PPG signals detected from tissue after an impact.

FIG. 28B illustrates a schematic diagram of graphs of PPG signals detected from tissue after an impact. Graph 2802 illustrates a PPG signal at an IR wavelength, such as 880 nm or 940 nm. The Graph 2804 illustrates a PPG signal at a UV range, such as 395 nm or 405 nm. In this embodiment, the biosensor 100 is positioned on the forearm over the same tissue after an impact to the forearm. The forearm has turned red and swollen due to increased blood flow to the tissue but incurs no abrasions or bruising. Due to the increased blood flow to the surface of the tissue, e.g. due to vasodilation of the vessels in the tissue, the PPG signals at the IR wavelength and UV wavelength have a more similar pulse shape and signal to noise ratio. In addition, the normalized power spectrum of the PPG signals in Graph 2814 are more similar as well due to the increase of blood flow at the surface of the tissue. When similar blood flow is detected at the different levels of tissue, the PPG signals at UV and IR wavelengths have a more similar pulse shape and power spectrum. This similarity in the PPG signals at the different wavelengths indicates an increase of blood flow in the surface tissue due to vasodilation from injury or infection.

The biosensor 100 may thus detect an infection at a wound site by comparing the pulse shape and normalized power spectrum of PPG signals in different spectrums. The infection creates increased blood flow, swelling and vasodilation in the tissue around the wound site. The biosensor 100 may detect this change in the optical absorption properties of the tissue and the presence of infection or possible infection.

Figure 29A:
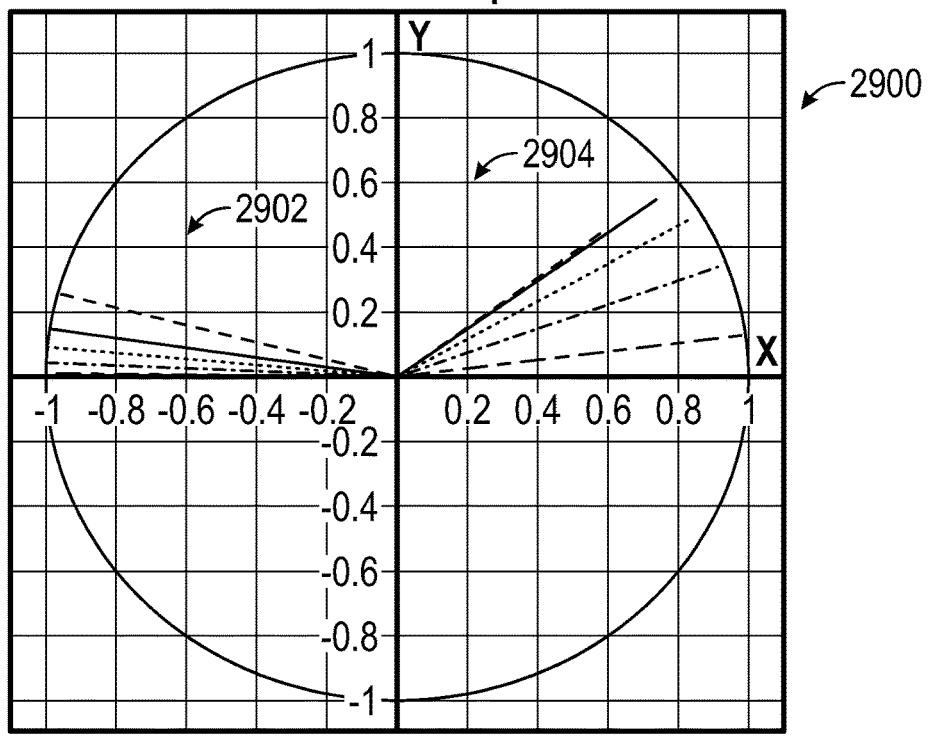
FIG. 29A illustrates a schematic diagram of a phasor relationship generated using PPG signals detected from normal tissue.

FIG. 29A illustrates a schematic diagram 2900 of a phasor relationship between PPG signals detected from normal tissue. The PPG signals were detected by the biosensor 100 positioned on a forearm over normal tissue as in FIG. 28A. In this embodiment, the biosensor 100 obtained the PPG signals at a plurality of wavelengths across UV, visible and IR spectrums. For example, the PPG signals may be at wavelengths of approximately Infrared: 940 nanometers, Red: 630 nanometers, Yellow: 590 nanometers, Green: 525 nanometers, Blue: 465 nanometers, UV 405 nanometers. These wavelengths are exemplary and other wavelengths may be implemented.

In Graph 2902, the PPG signals in the UV, visible and IR spectrums are processed using a linear fit model and transformed into vectors that represent a phase offset between the respective PPG signals. The angle or phase of the vectors in Graph 2902 are a representation of the phase offset or timing differences between the PPG signals in the different spectrums in normal tissue. In this example, the phase offset of the PPG signals is measured from the PPG signal at the UV wavelength. As such, the PPG signal at the UV wavelength is shown with no phase offset. The magnitude of the vectors is each scaled to a same value. As shown in Graph 2902, in the normal tissue, the PPG signals exhibit only a slight difference in phase or timing. This indicates that the tissue has normal circulation and nominal vasodilation is occurring in the tissue.

In Graph 2904, the PPG signals in the UV, visible and IR spectrums are processed using a Hilbert transformation into vectors, wherein a vector represents a difference in pulse shape and timing offset between the PPG signals. The Hilbert transformation is just one of many models that can be used to compare the pulse shape and temporal relationship between PPG signals and reduce the data to a vector or set of vectors. For example, the magnitude of the vectors represents a difference in the pulse shapes between the PPG signals. The phase of the vectors represents the temporal or timing differences between the PPG signals. These differences may be represented by similarity values, e.g. differences in pulse shape or temporal differences in the PPG signals. As shown in Graph 2904, in the normal tissue, the PPG signals exhibit differences in the magnitude of the vectors, and there is a greater difference in the phase offsets, e.g. the PPG signals have similar pulse shapes, but there are slight temporal differences between the signals. This indicates that the tissue has normal circulation and nominal vasodilation is occurring in the tissue.

Figure 29B:
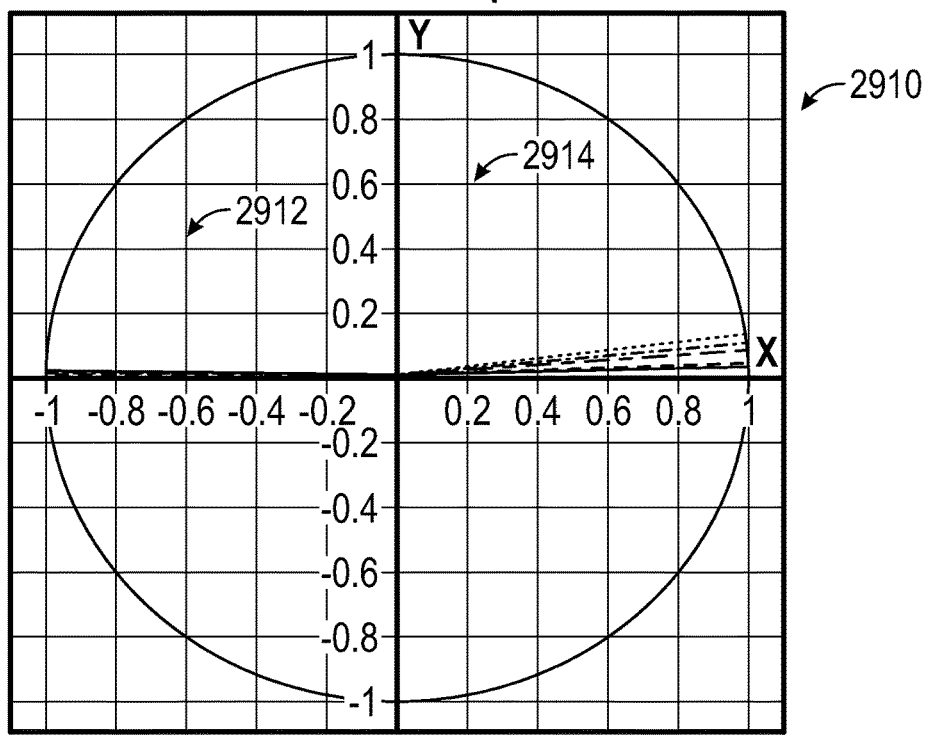
FIG. 29B illustrates a schematic diagram of graphs of PPG signals detected from tissue after an impact.

FIG. 29B illustrates a schematic diagram 2910 of graphs of PPG signals detected from tissue after an impact. In this embodiment, the biosensor 100 is positioned on the forearm over the same tissue after an impact to the forearm. The forearm has turned red and swollen due to increased blood flow to the tissue but incurs no abrasions or bruising. Due to the increased blood flow to the surface of the tissue, e.g. due to vasodilation of the vessels in the tissue, the PPG signals as represented in Graph 2912 have a decreased phase offset from normal tissue.

As such, the phase offset between two or more of the PPG signals in different spectrums, or having different depths of penetration of tissue, is measured. The phase offset may be used to determine presence of vasodilation/vasoconstriction or a problem with circulation in the tissue. The phase offset may be mapped to a level of vasodilation, e.g. using a calibration table or function. In addition, a phase offset may be used to determine a blood circulation level in the tissue, e.g. an abnormal circulation or a normal circulation. The abnormal circulation may include a high or low circulation level. A phase offset lower than a predetermined range (e.g. from a normal tissue measurement) may indicate a blood circulation problem in the tissue, e.g. that indicates increased blood flow due an infection or injury or that indicates a low circulation level. The predetermined range may be determined from testing healthy tissue of the patient or from testing healthy tissue of a general sample population.

The phase offset at one or more tissue sites may also be used to determine a systemic circulation level. For example, a low circulation level in several tissue sites of each leg of a patient may be used to determine a systemic circulation problem. In addition, NO levels, $SpO_2$, and/or skin temperature may also be used to determine a systemic circulation problem.

Graph 2914 illustrates the PPG signals as vectors, wherein the vectors represent a difference in pulse shape and phase offset of the PPG signals. For example, the magnitude of a vector represents a difference in the pulse shape of the PPG signal from a baseline heart rate PPG signal or between the PPG signals. The phase of a vector represents the temporal or timing differences between the PPG signal and a baseline heart rate PPG signal or between the PPG signals. These differences may be represented by a correlation or similarity value, e.g. differences in amplitude pulse shape and/or temporal differences in the PPG signal. When blood flow is increased to the tissue, the PPG signals at UV and IR wavelengths exhibit a lower variance in pulse shape and a higher correlation value. This decrease in the difference in the pulse shape of the PPG signals at the different wavelengths indicates an increase of blood flow in the surface tissue due to vasodilation from the injury.

As such, the extent or magnitude of the correlation in pulse shape between two or more of the PPG signals in different spectrums, or having different depths of penetration of tissue, may be used to determine presence of vasodilation/vasoconstriction or a circulation level in the tissue. The injury or infection creates increased blood flow, swelling and vasodilation in the tissue around the wound site. The biosensor 100 may detect this change in blood flow or vasodilation, and so detect a risk of infection or possible injury. A difference between pulse shapes or phase offset outside a normal range (e.g. from a normal tissue measurement) may indicate a blood circulation problem in the tissue, e.g. that indicates increased blood flow due to an infection or injury or that indicates high circulation. The correlation value may thus also be used to determine a blood circulation level in the tissue, e.g. a normal circulation or abnormal circulation (lower than normal or higher than normal). In addition, the correlation values of the PPG signals may be mapped to a level of vasodilation, e.g. using a calibration table or function.

Figure 29C:
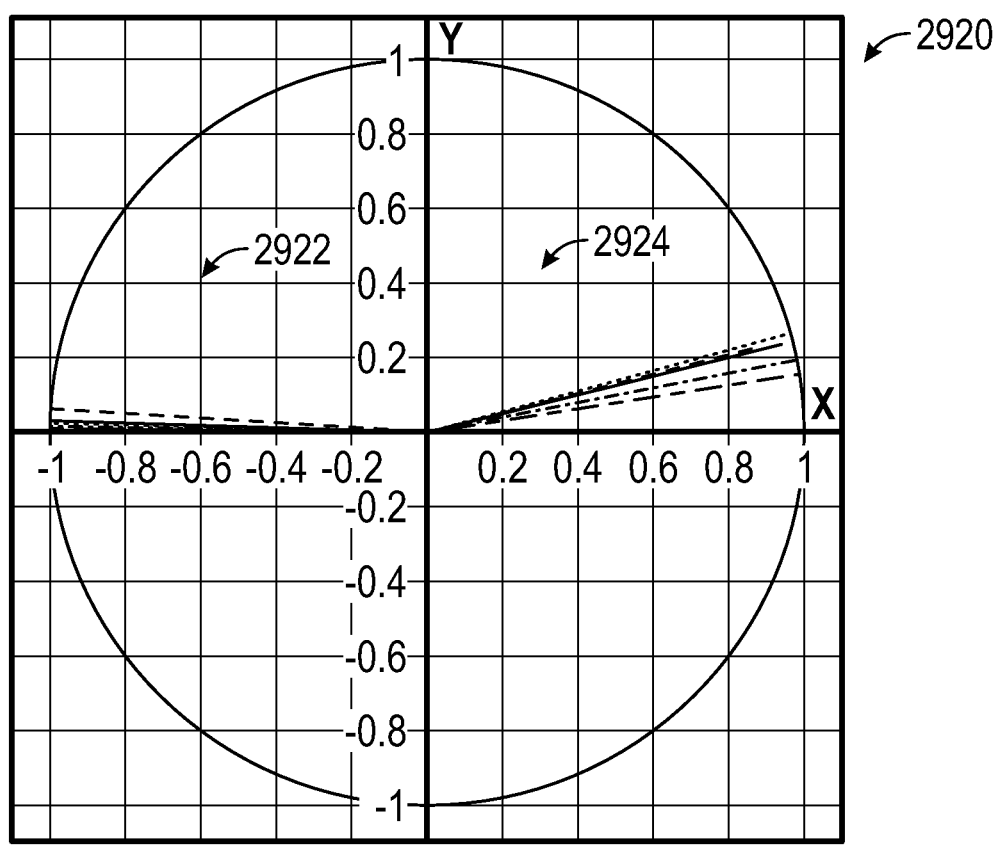
FIG. 29C illustrates a schematic diagram of graphs of PPG signals detected from tissue healing after an impact.

FIG. 29C illustrates a schematic diagram 2920 of graphs of PPG signals detected from tissue healing after an impact. In this embodiment, the biosensor 100 is positioned on the forearm as in FIG. 29B, and the PPG signals are obtained after the tissue has partially healed. The forearm has returned to a more normal skin tone and swelling has decreased. The vectors in Graph 2922 are a representation of the phase or timing offset between the PPG signals in the different spectrums in the healing tissue. In the healing tissue, the PPG signals have more phase offset than in the recently damaged tissue but still less than the normal tissue. This indicates that less vasodilation is occurring in the healing tissue than the injured tissue but more than in the normal tissue, and blood circulation is returning to normal as the tissue heals.

In Graph 2924, the PPG signals in the UV, visible and IR spectrums are processed using a Hilbert transformation into vectors that represent a pulse shape and phase offset between the PPG signals. The Hilbert transformation is just one of many models that can be used to compare the pulse shape and temporal relationship between PPG signals and reduce the data to a vector or set of vectors. The magnitude of the vectors represents a magnitude or extent of the difference in pulse shape and phase represents the phase offset of the PPG signal from other PPG signals. The differences in pulse shape and phase offset between the PPG signals have increased in the healing tissue as compared to the injured tissue. This indicates that less vasodilation is occurring in the healing tissue than in the injured tissue but more than in the normal tissue and blood circulation is returning to normal as the tissue heals.

The PPG signals may thus be used to determine a circulation level in skin tissue, detect an injury or infection in tissue and a level of vasodilation. The PPG signals obtained at one or more tissue sites may also be used to determine a systemic circulation level. For example, a low circulation level in several tissue sites of each leg of a patient may be used to determine a systemic circulation problem. In addition, NO levels, $SpO_2$, and/or skin temperature may also be used to determine a systemic circulation problem.

Figure 30A:
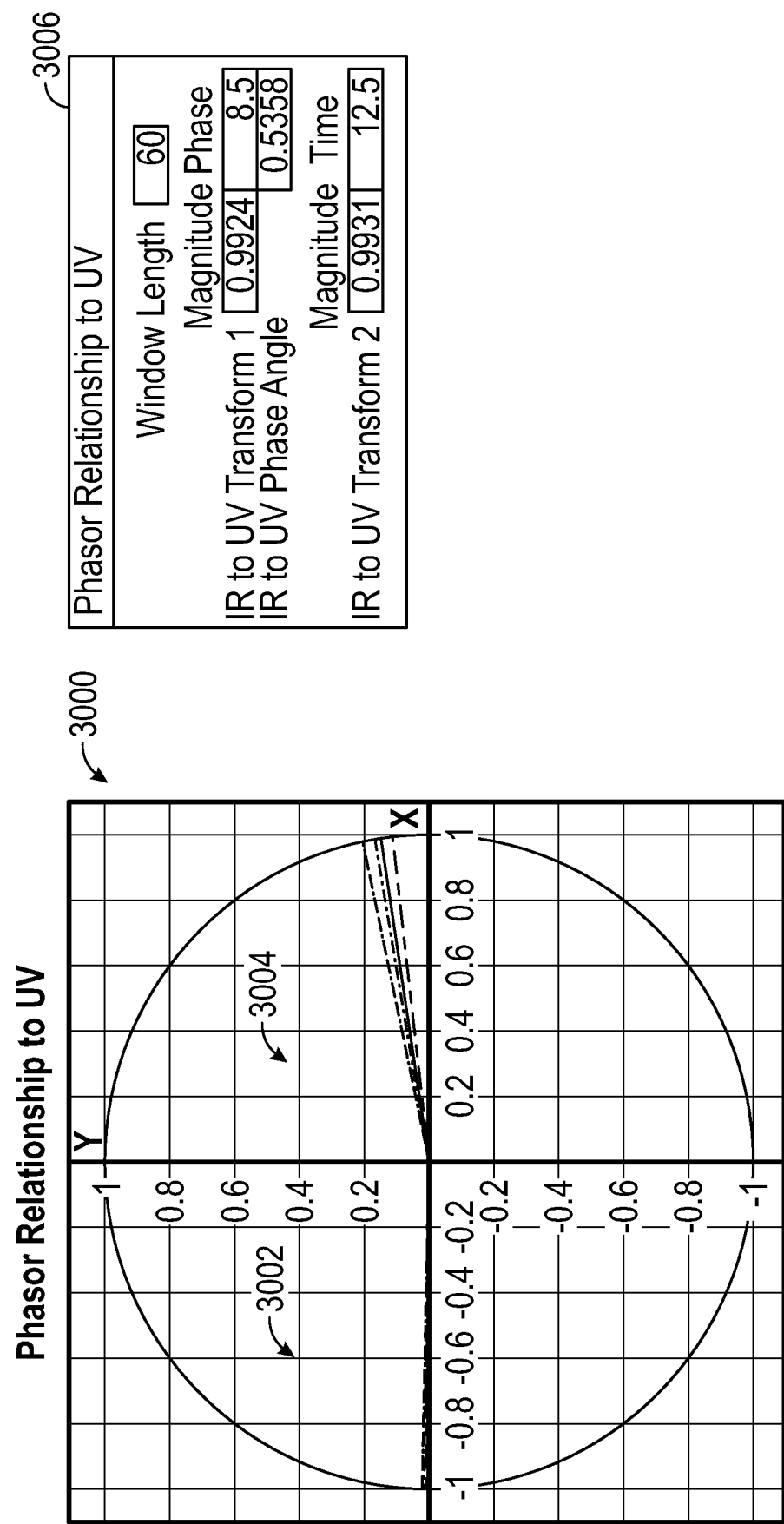
FIG. 30A illustrates a schematic diagram of a phasor relationship of PPG signals detected from normal tissue.

FIG. 30A illustrates a schematic diagram 3000 of a phasor relationship of PPG signals detected from normal tissue. In this embodiment, the biosensor 100 obtained PPG signals at a plurality of wavelengths across UV, visible and IR spectrums. For example, the PPG signals may be at wavelengths of approximately Infrared: 940 nanometers, Red: 630 nanometers, Yellow: 590 nanometers, Green: 525 nanometers, Blue: 465 nanometers, UV 405 nanometers. These wavelengths are exemplary and other wavelengths in the UV, visible or IR spectrums may be implemented. The PPG signals were detected by the biosensor 100 positioned on a fingertip having normal tissue and temperature.

In Graph 3002, the PPG signals in the UV, visible and IR spectrums are processed using a linear fit model and transformed into vectors with an angle that represent a phase offset of the respective PPG signal. The magnitude of the vectors is each scaled to a same value. The vectors in Graph 3002 are thus a representation of the phase or timing differences between the PPG signals. In the normal tissue, the PPG signals have little to no difference in phase or timing. This indicates that little to no vasodilation or vasoconstriction is occurring in the normal tissue at the fingertip and blood circulation is normal.

In Graph 3004, the PPG signals in the UV, visible and IR spectrums are processed using a Hilbert transformation into vectors that represent the similarity in pulse shape and phase offset between the PPG signals. The Hilbert transformation is just one of many models that can be used to compare the pulse shape and temporal relationship between PPG signals and reduce the data to a vector or set of vectors. For example, the magnitude of the vectors represents a difference in the pulse shapes between the PPG signals. The phase of the vectors represents the temporal or timing differences between the PPG signals. These differences may be represented by correlation values, e.g. differences in pulse shape or temporal differences in the PPG signals. A chart 3006 provides numerical values for the magnitude and phase of the Hilbert Data in Graph 3004 in a first line and a phase angle for the linear fit model of Graph 3002 in a second line. A cross correlation value of the PPG signals at an IR and UV wavelength is shown in a third line, this correlation value is another model for comparing the pulse shape and temporal relationship between PPG signals and reducing the data to a vector or set of vectors.

Figure 30B:
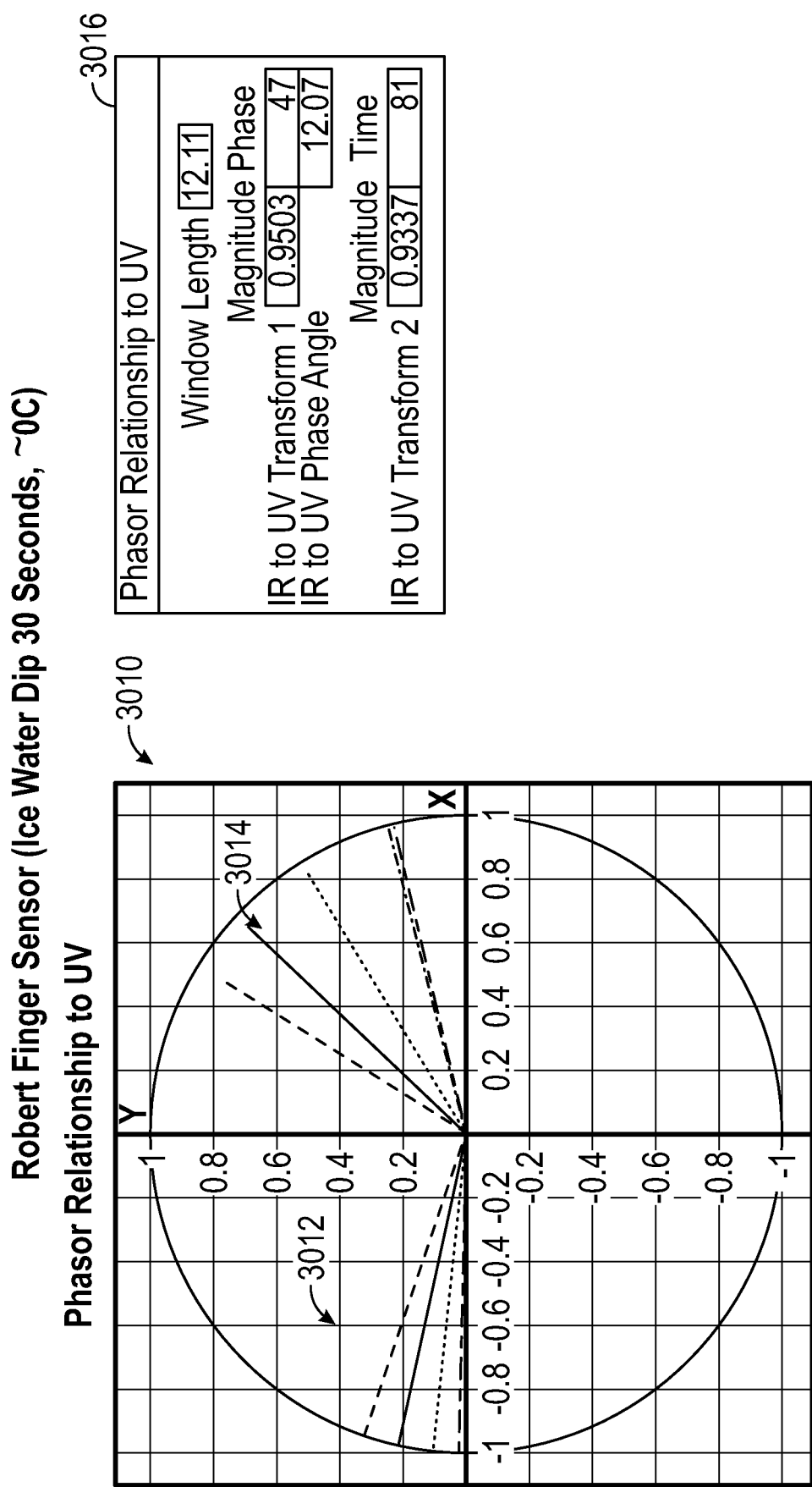
FIG. 30B illustrates a schematic diagram of a phasor relationship of PPG signals detected from tissue at subnormal temperature.

FIG. 30B illustrates a schematic diagram 3010 of a phasor relationship of PPG signals detected from tissue at subnormal temperature. In this embodiment, the biosensor 100 obtained the PPG signals at wavelengths of approximately Infrared: 940 nanometers, Red: 630 nanometers, Yellow: 590 nanometers, Green: 525 nanometers, Blue: 465 nanometers, UV 405 nanometers. These wavelengths are exemplary and other wavelengths in the UV, visible or IR spectrums may be implemented. The PPG signals were detected by the biosensor 100 positioned on the fingertip as in FIG. 30A after a temperature of the finger was lowered. The finger was submerged in ice water for a period of thirty seconds to lower the temperature of the surface tissue in the finger.

In Graph 3012, the PPG signals in the UV, visible and IR spectrums are processed using a linear fit model and transformed into vectors with an angle that represent a phase offset of the respective PPG signal. The magnitude of the vectors is each scaled to a same value. The vectors in Graph 3012 are thus a representation of the phase or timing offset between the PPG signals in the different spectrums in the tissue having a subnormal temperature. In this tissue, the PPG signals have a greater difference in phase or timing. This indicates that blood flow in the colder tissue near the surface is decreased, e.g. due to vasoconstriction, a low blood circulation level.

As such, the phase offset between two or more of the PPG signals in different spectrums, or having different depths of penetration of tissue, is measured. The phase offset may be used to determine presence of vasodilation/vasoconstriction or a circulation level in the tissue. The phase offset may be mapped or correlated to a level of vasodilation, e.g. using a calibration table or function. In addition, a phase offset exceeding a predetermined threshold (e.g. from a normal tissue measurement) may indicate a blood circulation problem in the tissue, e.g. that indicates increased blood flow due an infection or injury or that indicates low circulation.

In Graph 3014, the PPG signals in the UV, visible and IR spectrums are processed using a Hilbert transformation into vectors that represent the similarity in pulse shape and phase offset been the PPG signals. The Hilbert transformation is just one of many models that can be used to compare the pulse shape and temporal relationship between PPG signals and reduce the data to a vector or set of vectors. For example, the magnitude of the vectors represents a difference in the pulse shapes between the PPG signals. The phase of the vectors represents the temporal or timing differences between the PPG signals. These differences may be represented by correlation values, e.g. differences in pulse shape or temporal differences in the PPG signals. Again, in this tissue, the PPG signals have a greater difference or lower correlations in pulse shape. This indicates that blood flow in the colder surface tissue is decreased, e.g. due to vasoconstriction, and a low circulation level.

A chart 3016 provides numerical values for the magnitude and phase of the Hilbert Data in Graph 3014 in a first line and a phase angle for the linear fit model of Graph 3012 in a second line. A cross correlation value of the PPG signals at the IR and UV wavelength is shown in a third line, this correlation value is another model for comparing the pulse shape and temporal relationship between PPG signals and reducing the data to a vector or set of vectors.

The biosensor 100 may detect this change in blood flow or vasoconstriction, and so the presence of infection or possible injury. A correlation value that represents a difference between pulse shapes and/or temporal differences of different PPG signals exceeding or lower than predetermined thresholds (e.g. from a normal tissue measurement) may indicate an abnormal circulation in the tissue, e.g. an increased blood flow due an infection or injury or a low circulation level. In addition, the correlation value may be mapped to a level of vasodilation, e.g. using a calibration table or function.

The PPG signals may thus be used to detect a circulation level, infection, arterial stiffness, etc. One or more parameters derived using the PPG signals may be used to determine a period of vasodilation/vasoconstriction or a level of vasodilation/vasoconstriction. A phase offset between PPG signals or a correlation value between PPG signals may be used to determine a circulation level (such as high, normal or low) or possible injury or infection.

Figure 31:
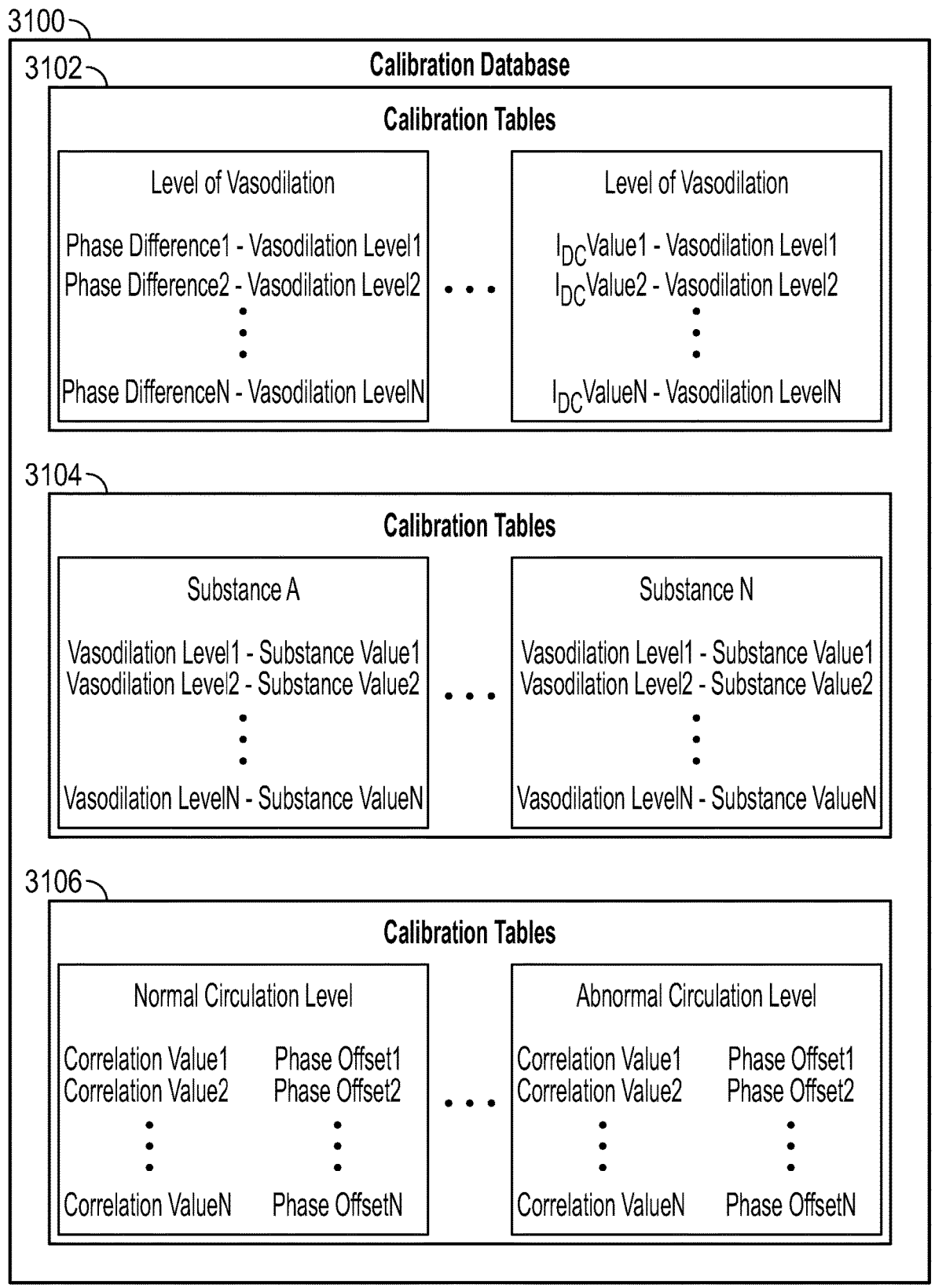
FIG. 31 illustrates a schematic block diagram of an embodiment of a calibration database stored in a memory device.

FIG. 31 illustrates a schematic block diagram of an embodiment of a calibration database 3100 stored in a memory device. The calibration database 3100 includes one or more calibration tables 3102 for mapping parameters obtained from PPG signals to a level of vasodilation. For example, values of phase offset between PPG signals may be mapped to corresponding levels of vasodilation. In another example, low frequency components $I_{DC}$ values may be mapped to corresponding levels of vasodilation. In another example, values of correlations between PPG signals may be mapped to corresponding levels of vasodilation.

The calibration database 3100 may also include one or more calibration tables 3104 to compensate or correct measurements for a level of a blood component during a period of vasodilation. For example, a calibration table 3104 includes an offset or correction to an R value measured during a period of vasodilation. The offset or correction may also depend on the level of vasodilation. In one aspect, the calibration database 3100 may include a correction to an L value or other measurement obtained using PPG signals during a period of vasodilation.

The calibration database 3100 may also include one or more calibration tables 3106 to map parameters obtained from the PPG signals to a circulation level. A range or list of correlation values or phase offsets may be mapped to a normal circulation level. A range or list of correlation values or phase offsets may be mapped to a low circulation level or a high circulation level (e.g. abnormal circulation levels).

The calibration database 3100 may alternatively or additionally include a set of calibration curves or functions to perform the mappings. The calibration database 3100 may be generated by testing a large general population using the biosensor 100 and using one or more alternate techniques. The calibration database 3100 may alternatively or additionally be adjusted for an individual by testing the individual patient using the biosensor 100 and then using an alternate technique.

Figure 32:
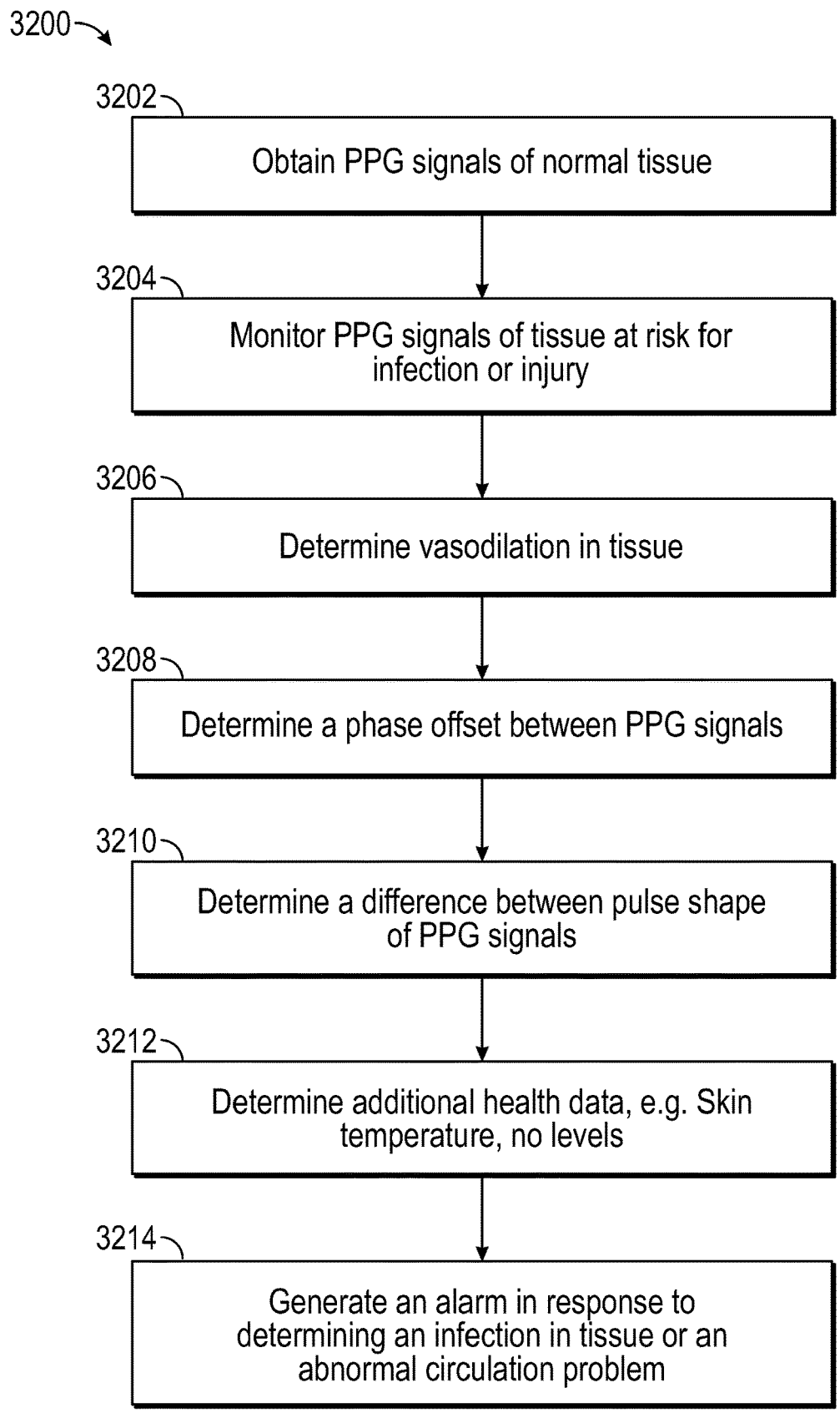
FIG. 32 illustrates a logical flow diagram of a method for detection of an infection in tissue.

FIG. 32 illustrates a logical flow diagram of a method 3200 for detection of an infection in tissue. The biosensor 100 obtains PPG signals from normal tissue at 3202. For example, a patch including the biosensor may be positioned over healthy tissue of a patient to obtain a baseline of $I_{DC}$ components of PPG signals or phase differences between the PPG signals or other parameters. The biosensor 100 may then be positioned over or around tissue at risk for infection or injury. For example, a patch including the biosensor 100 may be positioned over a wound or a surgery site. The biosensor 100 then monitors PPG signals detected from the tissue at 3204 and determines any periods of vasodilation or levels of vasodilation in the tissue at 3206.

The biosensor 100 may also determine a phase offset between PPG signals at 3208. The biosensor may also determine a correlation value between pulse shapes of the PPG signals at 3210. The phase offset and/or correlation value may be used to determine a blood circulation level in the tissue, e.g. a low circulation, normal circulation or a high circulation. Preferably, to determine the phase offset and/or correlation value, PPG signals in an infrared range (IR) range from 650 nm to 1350 nm and PPG signals in a UV range from 10 nm to 410 nm are compared.

The biosensor 100 may also monitor other health data, such as a skin temperature or NO levels in blood flow at 3212. Elevated NO levels are an indication of an infection or sepsis. The biosensor 100 may then generate a visible or audible alarm in response to determining abnormal circulation level or a possible infection in the tissue at 3214. The biosensor 100 may also transmit the alarm to another device, such as a smart phone or patient monitoring station. The biosensor 100 may also determine a systemic circulation level (low, normal, high) using one or more of PPG signals from multiple tissue sites, skin temperature, NO levels, or $SpO_2$ levels.

The biosensor 100 may be implemented in a patch or other form factor to monitor for infection in tissue or circulatory problems in tissue. The patch may be positioned near a wound, surgery site or other at risk tissue. A person with nerve damage may position the patch over tissue with little to no feeling to monitor for injury or low blood circulation. For example, a diabetic patient may place the biosensor 100 over tissue in a foot to monitor for low blood circulation. In another example, the biosensor 100 may be used to monitor for injury in a paralyzed limb of a patient. The biosensor 100 may thus be used as a vascular interrogator to monitor blood circulation or possibility of infection in tissue.

Embodiment—Detection of Vocalizations

In an embodiment, the PPG sensor may be used to detect vocalizations. For example, the biosensor 100 may implemented on an animal collar. When the animal includes a canine or dog, the biosensor 100 may detect barking by the animal. For example, when the animal is barking, an amplitude of the PPG signal increases or spikes in comparison to the PPG signal when the animal is at rest. For example, it may be determined that a patient (animal) has a resting heart rate with a normal PPG signal amplitude between 1000 and −1000 units. The measurements of the PPG signals are then obtained during vocalization of the patient. During barking, the PPG signal has an amplitude that is approximately 10 times the normal PPG signal at rest. The amplitude of the PPG signal may thus be monitored to determine a vocalization, such barking. The vocalization may trigger the biosensor 100 to perform a scan or measurement of vital signs. Additionally, the biosensor 100 may be implemented with an accelerometer to record activity levels. The biosensor 100 may thus be used to determine periods of vocalization, e.g. in animals, babies or comatose patients.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A device, comprising:
an optical circuit configured to:
detect photoplethysmography (PPG) signals over a monitoring period, wherein the PPG signals include a first spectral response obtained from light reflected around a first wavelength from skin tissue of a patient and a second spectral response obtained from light reflected around a second wavelength from the skin tissue of the patient, wherein the first wavelength penetrates the skin tissue of the patient at a different depth than the second wavelength;
a processing device configured to:
determine a correlation between a first pulse shape from the first spectral response and a second pulse shape from the second spectral response;
determine a ratio (R) value using the first spectral response and the second spectral response over a monitoring period, wherein the R value is determined using a ratio of an alternating current (AC) component of the first spectral response and an AC component of the second spectral response;
determine a change in the R value obtained using the first spectral response and the second spectral response during the monitoring period; and
determine one or more of: a vasodilation period or a level of vasodilation using the correlation between the first pulse shape and the second pulse shape and the change in the R value.

2. The device of claim 1, wherein the first wavelength penetrates the skin tissue of the patient at a greater depth than the second wavelength.

3. The device of claim 2, wherein the processing device is further configured to determine the vasodilation period and the level of vasodilation using the correlation between the first pulse shape and the second pulse shape and a phase offset between the first spectral response and the second spectral response.

4. The device of claim 3, wherein the processing device is further configured to:
determine an increase in the level of vasodilation in response to an increase in a correlation value between the first pulse shape and the second pulse shape.

5. The device of claim 3, wherein the processing device is further configured to:
determine a measurement of arterial stiffness using at least one of: a relative level of vasodilation compared to an average range of vasodilation or a rate of change of the level of vasodilation.

6. The device of claim 1, wherein the processing device is further configured to:
determine a change in amplitude of a low frequency component in the first spectral response or the second spectral response, wherein the low frequency component is not affected by pulsatile blood flow due to a cardiac cycle; and
determine the level of vasodilation or period of vasodilation using the change in amplitude of the low frequency component.

7. The device of claim 1, wherein the processing device is further configured to:
determine the level of vasodilation and the period of vasodilation using the change in the R value.

8. The device of claim 1, wherein the processing device is further configured to:
determine a change in optical absorption properties of the tissue using the first spectral response and the second spectral response; and
determine a level of vasodilation or period of vasodilation using the change in the optical absorption properties.

9. The device of claim 8, wherein the change in optical absorption properties is due to one or more of: an increase in blood flow in the tissue, movement of tissue due to widening of vessels or a change in tissue hue.

10. The device of claim 1, wherein the processing device is further configured to:
determine an infection in the tissue of the patient using the level of vasodilation or the period of vasodilation.

11. The device of claim 10, wherein the processing device is further configured to determine the infection in the tissue using the level of vasodilation in the tissue, the period of vasodilation and a tissue temperature.

12. The device of claim 1, wherein the level of vasodilation includes a measurement of one or more of: a percentage of change in arterial width, diameter or planar area.

13. A biosensor, comprising:
an optical circuit configured to:
detect a first photoplethysmography (PPG) signal reflected around a first wavelength from skin tissue of a patient and a second PPG signal reflected around a second wavelength from the skin tissue of the patient;
a processing circuit configured to:
determine a correlation value between the first and second PPG signals, wherein the correlation value depends on a difference in pulse shape between the first and second PPG signals;
compare the correlation value in pulse shape to a predetermined normal range of correlation values;
determine a ratio (R) value using the first spectral response and the second spectral response over a monitoring period, wherein the R value is determined using a ratio of an alternating current (AC) component of the first spectral response and an AC component of the second spectral; and
determine an abnormal circulation level when the correlation value and the R value is outside the predetermined normal range, wherein the abnormal circulation level indicates a blood circulation problem in the tissue.

14. The biosensor of claim 13, wherein the processing circuit is configured to determine that the circulation level is a normal circulation level or an abnormal circulation level.

15. The biosensor of claim 13, wherein the processing circuit is configured to determine a systemic circulation level and a circulation level at a tissue site.

16. The biosensor of claim 13, wherein the processing circuit is configured to determine the correlation value by determining a difference in pulse shape between the PPG signals and a temporal difference between the PPG signals.

17. The biosensor of claim 1, wherein the processing circuit is further configured to:
determine an infection in the skin tissue of the patient using the correlation value and the R value.

18. The biosensor of claim 13, wherein the first wavelength is in a range from 650 nm to 1350 nm and the second wavelength is outside the range from 650 nm to 1350 nm.

19. A device, comprising:
a photoplethysmography (PPG) circuit configured to:
obtain a first PPG signal around a first wavelength reflected from skin tissue of a patient and a second PPG signal around a second wavelength reflected from the skin tissue of the patient;
a processing device configured to:
obtain a measure of similarity in pulse shape between the first and second PPG signals;
compare the measure of similarity in pulse shape to a predetermined normal range;
determine a ratio (R) value using the first spectral response and the second spectral response over a monitoring period, wherein the R value is determined using a ratio of an alternating current (AC) component of the first spectral response and an AC component of the second spectral response;
determine a concentration level of nitric oxide (NO) using the R value; and
determine an abnormal circulation level using the comparison of the measure of similarity in pulse shape and the concentration level of NO, wherein the abnormal circulation level indicates a blood circulation problem in the tissue.

20. The device of claim 19, wherein the processing device is further configured to:
determine a risk of an infection in the skin tissue using the measure of similarity in pulse shape.

21. The device of claim 19, wherein the processing device is further configured to:
determine a difference in a normalized power spectrum between the first and second PPG signals; and
determine the abnormal circulation level using the difference in a normalized power spectrum, the R value and the correlation value.

22. The device of claim 19, wherein the predetermined normal range is determined using PPG signals from healthy tissue of a general sample population.

* * * * *